United States Patent
Mathews et al.

(10) Patent No.: US 8,735,322 B2
(45) Date of Patent: May 27, 2014

(54) HERBICIDES

(75) Inventors: Christopher John Mathews, Bracknell (GB); John Martin Clough, Bracknell (GB); Kevin Beautement, Bracknell (GB); Melloney Tyte, Bracknell (GB); Louisa Robinson, Bracknell (GB); Stephane AndréMarie Jeanmart, Stein (CH)

(73) Assignee: Syngenta Limited, Guildford, Surrey (GB)

( * ) Notice: Subject to any disclaimer, the term of this patent is extended or adjusted under 35 U.S.C. 154(b) by 236 days.

(21) Appl. No.: 13/125,224

(22) PCT Filed: Sep. 23, 2009

(86) PCT No.: PCT/EP2009/062327
§ 371 (c)(1),
(2), (4) Date: Oct. 24, 2011

(87) PCT Pub. No.: WO2010/046194
PCT Pub. Date: Apr. 29, 2010

(65) Prior Publication Data
US 2012/0035053 A1   Feb. 9, 2012

(30) Foreign Application Priority Data
Oct. 20, 2008 (GB) .................................. 0819205.6

(51) Int. Cl.
| A01N 43/08 | (2006.01) |
| A01N 43/16 | (2006.01) |
| A01N 43/28 | (2006.01) |
| A01N 43/32 | (2006.01) |
| C07D 307/12 | (2006.01) |
| C07D 309/06 | (2006.01) |
| C07D 313/04 | (2006.01) |
| C07D 317/26 | (2006.01) |
| C07D 319/06 | (2006.01) |
| C07D 335/02 | (2006.01) |
| C07D 493/04 | (2006.01) |
| C07D 493/10 | (2006.01) |

(52) U.S. Cl.
USPC ........... 504/103; 504/130; 504/140; 504/251; 504/288; 504/292; 504/293; 504/294; 504/295; 504/296; 546/282.1; 549/13; 549/28; 549/375; 549/427; 549/498

(58) Field of Classification Search
None
See application file for complete search history.

(56) References Cited

U.S. PATENT DOCUMENTS

| 4,175,135 A | 11/1979 | Haines et al. |
| 4,209,532 A | 6/1980 | Wheeler et al. |
| 4,409,153 A | 10/1983 | Hodakowski et al. |
| 4,526,723 A | 7/1985 | Wheeler et al. |
| 4,659,372 A | 4/1987 | Wheeler et al. |
| 6,458,965 B1 | 10/2002 | Lieb et al. |
| 6,894,005 B1 | 5/2005 | Maetzke et al. |
| 8,058,210 B2 | 11/2011 | Lieb et al. |
| 8,084,649 B2 | 12/2011 | Muehlebach et al. |
| 2003/0216260 A1 | 11/2003 | Ruther et al. |
| 2007/0135630 A1 | 6/2007 | Fischer et al. |
| 2010/0113270 A1 | 5/2010 | Mathews et al. |
| 2010/0216638 A1 | 8/2010 | Mathews et al. |

FOREIGN PATENT DOCUMENTS

| CA | 2456776 A1 | 2/2004 |
| DE | 2813341 A1 | 10/1978 |
| DE | 2813341 C2 | 4/1983 |
| WO | W099/43649 A1 | 9/1999 |
| WO | W099/48869 A1 | 9/1999 |
| WO | WO01/17972 A2 | 3/2001 |
| WO | WO01/74770 A1 | 10/2001 |
| WO | WO0288098 A1 | 11/2002 |
| WO | WO03/013249 A1 | 2/2003 |
| WO | WO2007121868 A1 | 11/2007 |
| WO | WO2007140881 A1 | 12/2007 |
| WO | WO2008/071405 A1 | 6/2008 |
| WO | 2008110307 | 9/2008 |
| WO | WO2008/110307 A1 | 9/2008 |
| WO | WO2008/110308 A2 | 9/2008 |

OTHER PUBLICATIONS

Olson et al., caplus an 1995:665400.*
Wenger, J. and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

* cited by examiner

Primary Examiner — Sun Jae Loewe
(74) Attorney, Agent, or Firm — R. Kody Jones

(57) ABSTRACT

Cyclohexanedione compounds, which are suitable for use as herbicides.

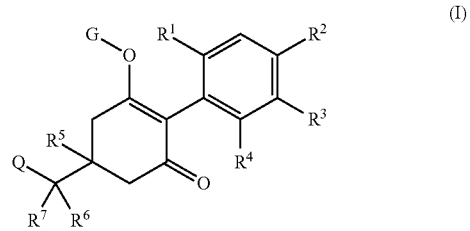

18 Claims, No Drawings

HERBICIDES

This application is a 371 of International Application No. PCT/EP2009/062327 filed Sep. 23, 2009, which claims priority to GB 0819205.6 filed Oct. 20, 2008, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 08/110,308.

Novel cyclohexanedione compounds having herbicidal and growth-inhibiting properties have now been found.

The present invention accordingly relates to compounds of formula I

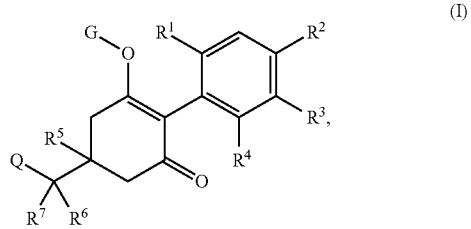

wherein $R^1$ is methyl, ethyl, n-propyl, isopropyl, cyclopropyl, halomethyl, haloethyl, halogen, vinyl, ethynyl, methoxy, ethoxy, halomethoxy or haloethoxy, $R^2$ and $R^3$ are, independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$ alkyl, $C_1$-$C_3$haloalkyl, $C_1$-$C_3$alkoxy, $C_1$-$C_3$alkoxy-$C_1$-$C_3$alkoxy, $C_1$-$C_3$haloalkoxy, aminocarbonyl, cyano, nitro, halogen, $C_1$-$C_3$alkylthio, $C_1$-$C_3$alkylsulfinyl or $C_1$-$C_3$alkylsulfonyl, or phenyl wherein 2 adjacent carbon atoms are bridged by a —O—CH$_2$—O— or —O—CH$_2$—CH$_2$—O— group, or heteroaryl or heteroaryl substituted by $C_1$-$C_4$ alkyl, $C_1$-$C_3$haloalkyl, $C_1$-$C_3$alkoxy, cyclopropyl-$C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, methyl, ethyl, n-propyl, isopropyl, halomethyl, haloethyl, halogen, vinyl, ethynyl, methoxy, ethoxy, halomethoxy or haloethoxy, $R^5$ is hydrogen or methyl, $R^6$ and $R^7$ are independently hydrogen, methyl, ethyl, $C_3$-$C_6$cycloalkyl, halogen, halomethyl, haloethyl, halogen, methoxy, halomethoxy, haloethoxy, or together $R^6$ and $R^7$ are joined to form together with the carbon atom to which they are attached a 3-7 membered ring or a 3-7 membered ring substituted by one or two methyl groups, Q is a 3- to 8-membered saturated or mono-unsaturated heterocycle containing at least one heteroatom selected from O, N and S(O)$_p$, or Q is a 3- to 8-membered saturated or mono-unsaturated heterocycle containing at least one heteroatom selected from O, N and S(O)$_p$, which is substituted by =O, $C_1$-$C_4$ alkyl, $C_1$-$C_4$ haloalkyl, $C_1$-$C_4$ alkoxy-$C_1$-$C_2$ alkyl, $C_3$-$C_6$cycloalkyl or $C_3$-$C_6$cycloalkyl-$C_1$-$C_3$alkyl, or is substituted by a 3- to 6-member heterocycyl containing at least one heteroatom selected from O and N, or is substituted by a 3- to 6-membered heterocyclyl-$C_1$-$C_3$alkyl containing at least one heteroatom selected from O and N, or is substituted by a spiro-$C_3$-$C_6$cycloalkyl or a spiro-3- to 8-membered saturated heterocycle containing at least one heteroatom selected from O, N and S(O)$_p$, or is bridged by a —O—CH$_2$— group, or Q is a 6- to 10-membered bicyclic heterocycle containing at least one heteroatom selected from O, N and S(O)$_p$, p is 0, 1 or 2, and G is hydrogen, $C_1$-$C_6$alkyl, $C_3$-$C_6$alkenyl, $C_3$-$C_6$alkynyl, an alkali metal, alkaline earth metal, a sulfonium, ammonium or latentiating group.

In the substituent definitions of the compounds of the formula I, the alkyl substituents and alkyl moieties of alkoxy, alkylsulfonyl etc. having 1 to 6 carbon atoms are preferably methyl, ethyl as well as propyl, butyl, pentyl and hexyl, in form of their straight and branched isomers. The alkenyl and alkynyl radicals having 2 to 6 carbon atoms as well as up to 10 carbon atoms can be straight or branched and can contain more than 1 double or triple bond. Examples are vinyl, allyl, propargyl, butenyl, butynyl, pentenyl and pentynyl. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred halogens are chlorine and bromine. Preferred examples of heteroaryls are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl and thiadiazolyl, and, where appropriate, N-oxides and salts thereof. These aryls and heteroaryls can be substituted by one or more substituents, where preferred substituents are $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl and $C_1$-$C_3$alkylsulfonyl. The 3-7 membered rings formed by $R^6$ and $R^7$ together with the carbon atom to which they are attached are preferably saturated and preferably carbocyclic rings which can be substituted by one or two methyl groups. Examples of the preferred saturated or mono-unsaturated rings Q can be found below as groups $Q_1$ to $Q_{85}$. The group G denotes hydrogen, an alkali metal cation such as sodium or potassium, alkaline earth metal cation such as calcium, sulfonium cation (preferably —S(C$_1$-C$_6$alkyl$_3$)$^+$) or ammonium cation (preferably —NH$_4^+$ or —N(C$_1$-C$_6$alkyl)$_4^+$), or C$_1$-C$_6$alkyl, C$_3$-C$_6$alkenyl or C$_3$-C$_6$alkynyl or a latentiating group. The latentiating group G is preferably selected from the groups —C(X$^1$)—R$^6$, C(X$^2$)—X$^3$—R$^7$, —C(X$^4$)—NR$^8$R$^9$, —SO$_2$R$^{10}$, P(X$^5$)R$^{11}$R$^{12}$ or CH$_2$—X$^6$—R$^{13}$, wherein X$^1$, X$^2$, X$^3$, X$^4$, X$^5$ and X$^6$ are independently of each other oxygen or sulfur;

$R^6$, $R^7$, $R^8$ and $R^9$ are each independently of each other hydrogen, $C_1$-$C_{10}$ alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$-aminoalkyl$C_1$-$C_5$alkyl, $C_2$-$C_8$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl, heteroaryl$C_1$-$C_5$alkyl, $C_2$-$C_5$alkenyl, $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy, $R^{10}$, $R^{11}$, $R^{12}$ are hydrogen, $C_1$-$C_{10}$ alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$ aminoalkyl$C_1$-$C_5$alkyl, $C_2$-$C_5$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxoy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$aminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl, heteroaryl$C_1$-$C_5$alkyl, $C_2$-$C_5$alkenyl, $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino, $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^{13}$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$aminoalkyl$C_1$-$C_5$alkyl, $C_2$-$C_8$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$ alkylideneaminoxoy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$aminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$ trialkylsilyl$C_1$-$C_5$alkyl, phenyl$C_1$-$C_5$alkyl, heteroaryl$C_1$-$C_5$alkyl, phenoxy$C_1$-$C_5$alkyl, heteroaryloxy$C_1$-$C_5$alkyl, $C_2$-$C_5$alkenyl, $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino, or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di$C_3$-$C_7$cycloalkylamino or $C_3$-$C_7$cycloalkoxy or $C_1$-$C_{10}$alkylcarbonyl.

In particular, the latentiating group G is a group —C($X^1$)—$R^6$ or —C($X^2$)—$X^3$—$R^7$, and the meanings of $X^1$, $R^6$, $X^2$, $X^3$ and $R^7$ are as defined above.

These latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

In a preferred group of compounds of the formula I, $R^1$ is methyl, ethyl, cyclopropyl or methoxy.

Preferably, $R^2$ and $R^3$ in the compounds of formula I are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or thienyl, thienyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, furyl, furyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrazolyl, pyrazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, thiazolyl, thiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, oxazolyl, oxazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, isothiazolyl, isothiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, isoxazolyl, isoxazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, triazolyl, triazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, oxadiazolyl, oxadiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, thiadiazolyl, thiadiazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, tetrazolyl, tetrazolyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyridyl, pyridyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrimidinyl, pyrimidinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyridazinyl, pyridazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, pyrazinyl or pyrazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, triazinyl or triazinyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, More preferably, $R^2$ and $R^3$ are independently hydrogen, halogen, $C_1$-$C_6$alkyl, $C_1$-$C_6$alkoxy, $C_2$-$C_6$alkenyl, $C_2$-$C_6$alkynyl, phenyl or phenyl substituted by $C_1$-$C_4$alkyl, $C_1$-$C_3$haloalkyl, cyano, nitro, halogen or $C_1$-$C_3$alkylsulfonyl.

In even more preferred compounds of the formula I, $R^2$ and $R^3$ are independently hydrogen, chlorine, bromine, methyl, methoxy, ethyl, ethoxy, ethenyl, ethynyl, phenyl or phenyl substituted by methyl, trifluoromethyl, cyano, nitro, fluorine, chlorine or methylsulfonyl.

Preferably, $R^4$ is hydrogen, methyl, ethyl, chlorine, bromine, vinyl, ethynyl or methoxy.

Preferred are those compounds of the formula I, wherein $R^5$ is hydrogen.

In another preferred group of the compounds of the formula I one of $R^6$ and $R^7$ are hydrogen.

It is also preferred that $R^6$ and $R^7$ are both hydrogen.

Preferably, G denotes hydrogen, an alkali metal or alkaline earth metal, where hydrogen is particularly preferred.

Preferred groups Q are those of the formula

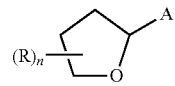 Q1

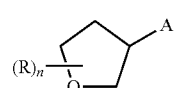 Q2

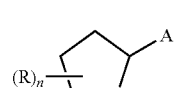 Q3

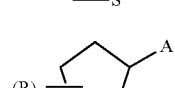 Q4

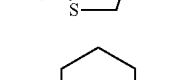 Q5

-continued

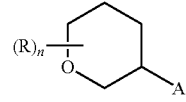 Q6

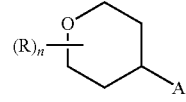 Q7

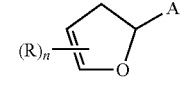 Q8

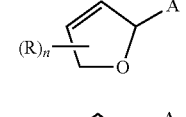 Q9

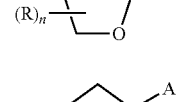 Q10

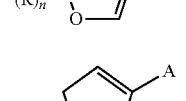 Q11

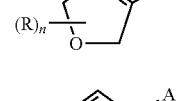 Q12

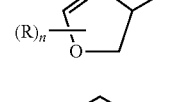 Q13

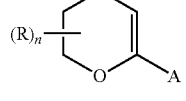 Q14

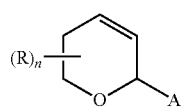 Q15

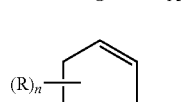 Q16

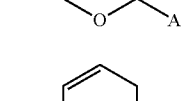 Q17

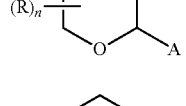 Q18

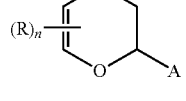 Q19

| | |
|---|---|
| 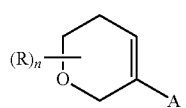 | Q20 |
| 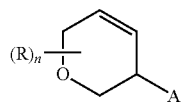 | Q21 |
| 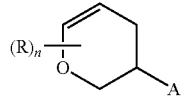 | Q22 |
| 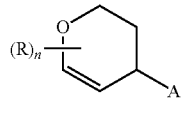 | Q23 |
| 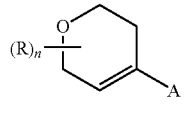 | Q24 |
| 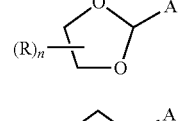 | Q25 |
| 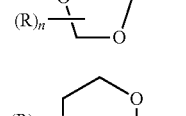 | Q26 |
| 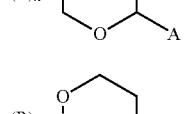 | Q27 |
| 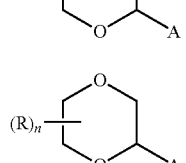 | Q28 |
| 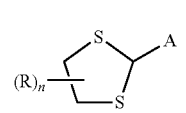 | Q29 |
| 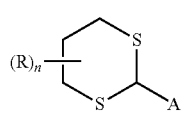 | Q30 |
| 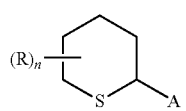 | Q31 |
| 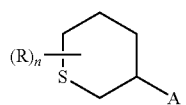 | Q32 |
| 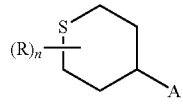 | Q34 |
| 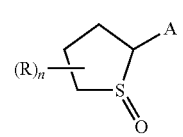 | Q35 |
| 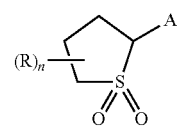 | Q36 |
| 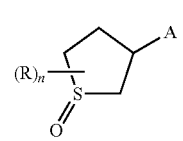 | Q37 |
| 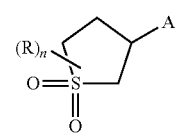 | Q38 |
| 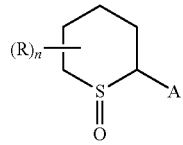 | Q39 |
| 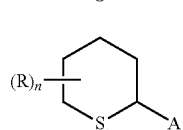 | Q40 |
| 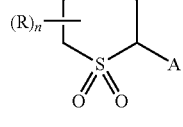 | Q41 |
| 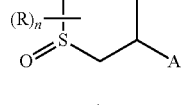 | Q42 |
| 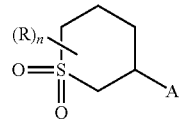 | Q43 |
| 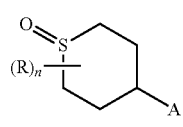 | Q44 |
| 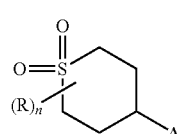 | |
| 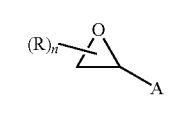 | Q45 |

-continued
| | |
|---|---|
| 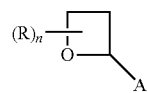 | Q46 |
| 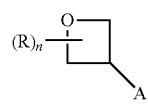 | Q47 |
| 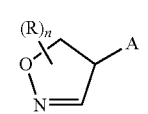 | Q48 |
| 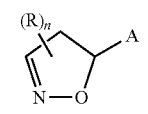 | Q49 |
| 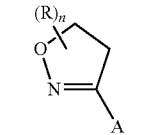 | Q50 |
| 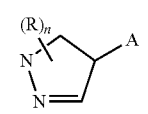 | Q51 |
| 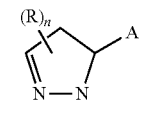 | Q52 |
| 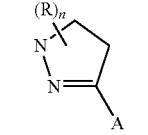 | Q53 |
| 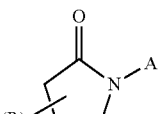 | Q54 |
| 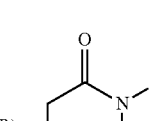 | Q55 |
| 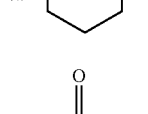 | Q56 |
| 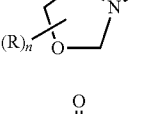 | Q57 |
-continued
| | |
|---|---|
| 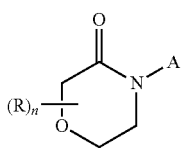 | Q58 |
| 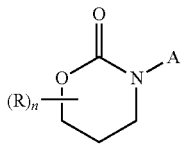 | Q59 |
| 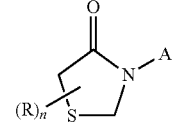 | Q60 |
| 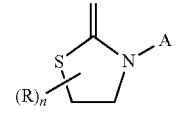 | Q61 |
| 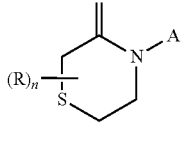 | Q62 |
| 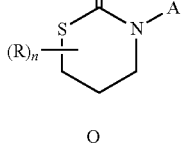 | Q63 |
| 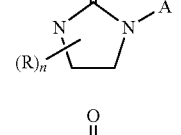 | Q64 |
| 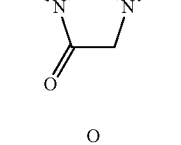 | Q65 |
| 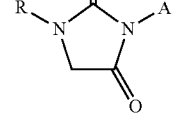 | Q66 |
| 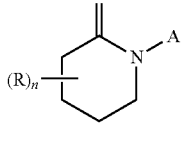 | Q67 |

-continued

Q68 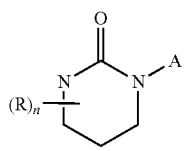

Q69 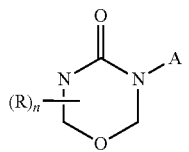

Q70 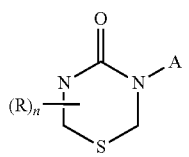

Q71 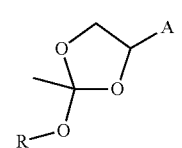

Q72 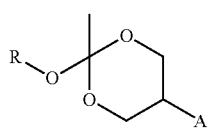

Q73 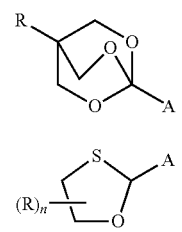

Q74 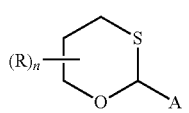

Q75 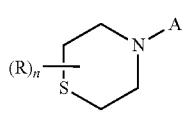

Q76 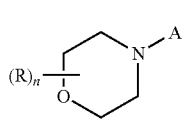

Q77 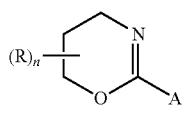

Q78 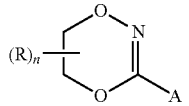

Q79

-continued

Q80 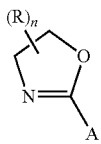

Q81 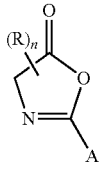

Q82 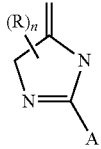

Q83 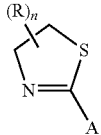

Q84 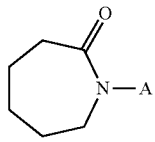

Q85 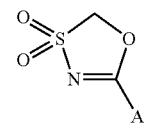

Q86 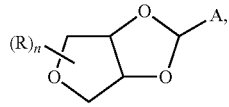

wherein R is $C_{1-4}$ alkyl, $C_{1-4}$ haloalkyl, $C_{1-4}$ alkoxy $C_{1-2}$ alkyl or $C_{3-6}$ cycloalkyl, n is 0 to 4 and -A denotes the position of attachment to the methylene moiety $-CR^5R^6-$.

Groups $Q_1$, $Q_2$, $Q_5$, $Q_6$, $Q_7$, $Q_{25}$, $Q_{26}$, $Q_{27}$, $Q_{28}$, $Q_{29}$, $Q_{34}$, $Q_{42}$ and $Q_{43}$ are even more preferred, where Groups, $Q_2$, $Q_7$, $Q_{25}$, $Q_{27}$, $Q_{34}$, $Q_{42}$ and $Q_{43}$ are especially preferred.

Preferably, R is methyl or ethyl.

0, 1 and 2 are the preferred meanings of n.

In another group of preferred compounds of the formula I, Q is a 6- to 10-membered bicyclic heterocycle such as $Q_{73}$ and $Q_{86}$, especially $Q_{86}$.

In a particularly preferred group of compounds of the formula I, $R^1$ is methyl, ethyl or methoxy, $R^2$ and $R^3$ are independently hydrogen, halogen, $C_1$-$C_6$alkyl, phenyl, phenyl substituted by $C_1$-$C_4$alkyl, $C_1$-$C_3$haloalkyl, $C_1$-$C_3$alkoxy, $C_1$-$C_3$alkoxy-$C_1$-$C_3$alkoxy, $C_1$-$C_3$haloalkoxy, aminocarbonyl, cyano or halogen, or phenyl wherein 2 adjacent carbon atoms are bridged by a $-O-CH_2-O-$ or $-O-CH_2-CH_2-O-$ group, or heteroaryl or heteroaryl substituted by $C_1$-$C_3$alkoxy or cyclopropyl-$C_1$-$C_3$alkoxy, $R^4$ is hydrogen, methyl or ethyl, $R^5$ is hydrogen, $R^6$ and $R^7$ are independently hydrogen or methyl, Q is a 5- to 7-membered saturated heterocycle containing at least one heteroatom selected from O and $S(O)_p$, or Q is a 5- to 7-membered saturated or mono-unsaturated heterocycle containing at least one heteroatom selected from O and $S(O)_p$, which is substituted by $C_1$-$C_4$alkyl or $C_1$-$C_4$alkoxy-$C_1$-$C_2$alkyl, or is substituted by a 5- to 6-membered heterocycyl containing at least one O atom, or is substituted by a 5- to 6-membered heterocyclyl-$C_1$-$C_3$alkyl containing at least one O atom, or is substituted by a spiro-$C_3$-$C_6$cycloalkyl or a spiro-5- to 6-membered saturated heterocycle containing at least one O atom, or Q is a 8- to 10-membered bicyclic heterocycle containing at least one O atom, p is 0, 1 or 2, and G is hydrogen.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$ alkyl. Further suitable tetraalkylammonium bases with other anions can be obtained, for example, by anion exchange reactions.

Depending on the nature of the substituents, compounds of formula I may exist in different isomeric forms. When G is hydrogen, for example, compounds of formula I may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the formula I.

A compound of formula I wherein G is $C_1$-$C_8$ alkyl, $C_3$-$C_8$ alkenyl, $C_3$-$C_8$ alkynyl, $C(X^1)$—$R^{20}$, $C(X^2)$—$X^3$—$R^{21}$, $C(X^4)$—$N(R^{22})$—$R^{23}$, —$SO_2$—$R^{24}$, —$P(X^5)(R^{25})$—$R^{26}$ or $CH_2$—$X$—$R^{27}$ where $X^1$, $X^2$, $X^3$, $X^4$, $X^5$, $X$, $R^{20}$, $R^{21}$, $R^{22}$, $R^{23}$, $R^{24}$, $R^{25}$, $R^{26}$ and $R^{27}$ are as defined above may be prepared by treating a compound of Formula (A), which is a compound of formula I wherein G is H, with an alkylating agent such as an alkyl halide (the definition of alkyl halides includes simple alkyl halides such as methyl iodide and ethyl iodide and substituted alkyl halides such as chloromethyl alkyl ethers, Cl—$CH_2$—$X$—$R^{27}$, wherein X is oxygen, and chloromethyl alkyl sulfides Cl—S—$CH_2$—$X$—$R^{27}$, wherein X is sulfur), an alkyl sulfonate, or a dialkyl sulfate, or with an alkenyl halide, or with an alkynyl halide, or with an acylating agent such as a carboxylic acid, HO—$C(X^1)R^{20}$, wherein $X^1$ is oxygen, an acid chloride, Cl—$C(X^1)R^{20}$, wherein $X^1$ is oxygen, or acid anhydride, $[R^{20}C(X^1)]_2O$, wherein $X^1$ is oxygen, or an isocyanate, $R^{22}N$=C=O, or a carbamoyl chloride, Cl—$C(X^4)$—$N(R^{22})$—$R^{23}$ (wherein $X^4$ is oxygen and with the proviso that neither $R^{22}$ or $R^{23}$ is hydrogen), or a thiocarbamoyl chloride, Cl—$C(X^4)$—$N(R^{22})$—$R^{23}$ (wherein $X^4$ is sulfur and with the proviso that neither $R^{22}$ or $R^{23}$ is hydrogen) or a chloroformate, Cl—$C(X^2)$—$X^3$—$R^{21}$, (wherein $X^2$ and $X^3$ are oxygen), or a chlorothioformate Cl—$C(X^2)$—$X^3$—$R^{21}$ (wherein $X^2$ is oxygen and $X^3$ is sulfur), or an isothiocyanate, $R^{22}N$=C=S, or by sequential treatment with carbon disulfide and an alkylating agent, or with a phosphorylating agent such as a phosphoryl chloride, Cl—$P(X^5)(R^{25})$—$R^{26}$ or with a sulfonylating agent such as a sulfonyl chloride $C_1$—$SO_2$—$R^{24}$, preferably in the presence of at least one equivalent of base.

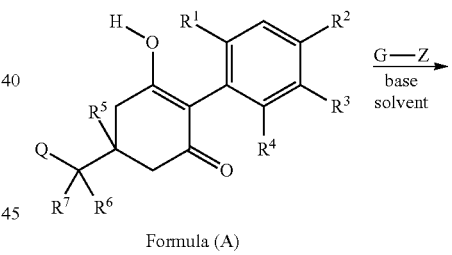

Formula (A)

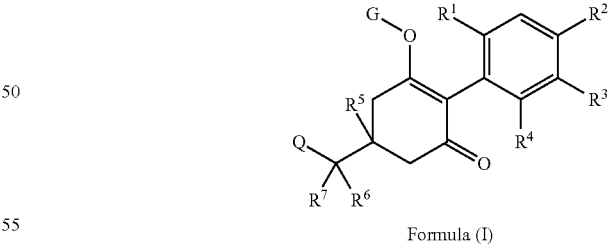

Formula (I)

The O-alkylation of cyclic 1,3-diones is known; suitable methods are described, for example, in U.S. Pat. No. 4,436,666. Alternative procedures have been reported by M. T. Pizzorno and S. M. Albonico, Chem. Ind. (London), 1972, 425; H. Born et al., J. Chem. Soc., 1953, 1779; M. G. Constantion et al., Synth. Commun., 1992, 22 (19), 2859; Y. Tian et al., Synth. Commun., 1997, 27 (9), 1577 and by S. Chandra Roy et al., Chem. Letters, 2006, 35, (No 1) 16.

The acylation of 2-arylcycloxane-3,5-diones may be effected by procedures similar to those described, for example, in U.S. Pat. No. 4,175,135, U.S. Pat. No. 4,422,870, U.S. Pat. No. 4,659,372 and U.S. Pat. No. 4,436,666. Typically diones of Formula (A) are treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane or acetonitrile. Suitable procedures are described, for example, by W. Zhang and G. Pugh, Tetrahedron Lett., 1999, 40 (43), 7595-7598 and T. Isobe and T. Ishikawa, J. Org. Chem., 1999, 64 (19) 6984.

Phosphorylation of 2-arylcyclohexane-3,5-diones may be effected using procedures analogous to those described in U.S. Pat. No. 4,409,153.

Sulfonylation of a compound of Formula (A) may be achieved using an alkyl or aryl sulfonyl halide, preferably in the presence of at least one equivalent of base, for example by the procedure of C. J. Kowalski and K. W. Fields, J. Org. Chem., 1981, 46, 197.

A compound of Formula (A) may be prepared via the cyclisation of a compound of Formula (B), wherein R is hydrogen or an alkyl group, preferably in the presence of an acid or base, and optionally in the presence of a suitable solvent, by analogous methods to those described in U.S. Pat. No. 4,209,532. The compounds of Formula (B) have been particularly designed as intermediates in the synthesis of the compounds of the Formula I. A compound of Formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

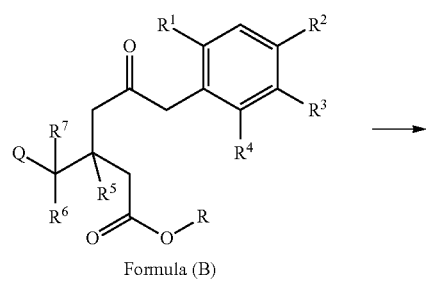

Formula (B)

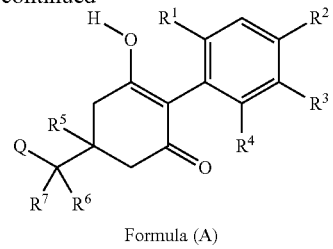

Formula (A)

A compound of Formula (B) wherein R is alkyl (preferably methyl or ethyl), may be cyclised under basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

A compound of Formula (B), wherein R is H, may be prepared by saponification of a compound of Formula (C) wherein R' is alkyl (preferably methyl or ethyl), under standard conditions, followed by acidification of the reaction mixture to effect decarboxylation, by similar processes to those described, for example, in U.S. Pat. No. 4,209,532.

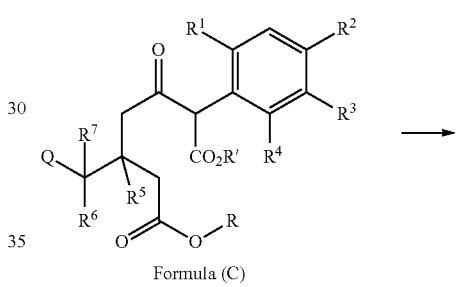

Formula (C)

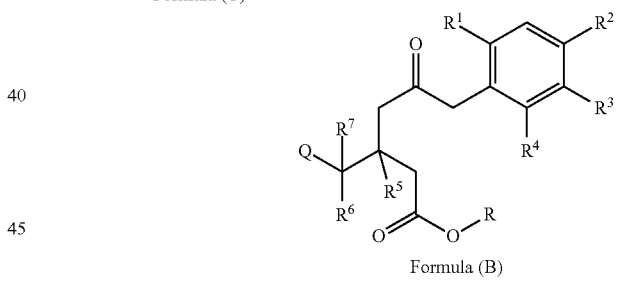

Formula (B)

A compound of Formula (B), wherein R is H, may be esterified to a compound of Formula (B), wherein R is alkyl, under known conditions, for example by heating with an alkyl alcohol, ROH, in the presence of an acid catalyst.

A compound of Formula (C), wherein R is alkyl, may be prepared by treating a compound of Formula (D) with a suitable carboxylic acid chloride of Formula (E) wherein under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, a compound of Formula (C), wherein R is H, may be prepared by treating a compound of Formula (D) with a suitable base (such as potassium tert-butoxide, sodium bis(trimethylsilyl) amide and lithium diisopropylamide) in a suitable solvent (such as tetrahydrofuran or toluene) at a suitable temperature (between −80° C. and 0° C.) and reacting the resulting anion with a suitable anhydride of Formula (F):

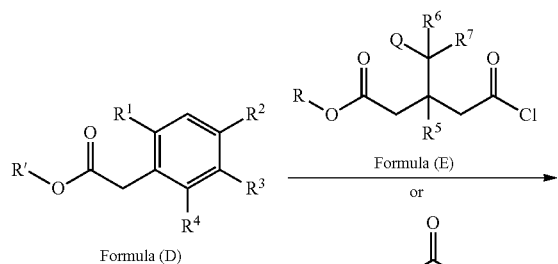

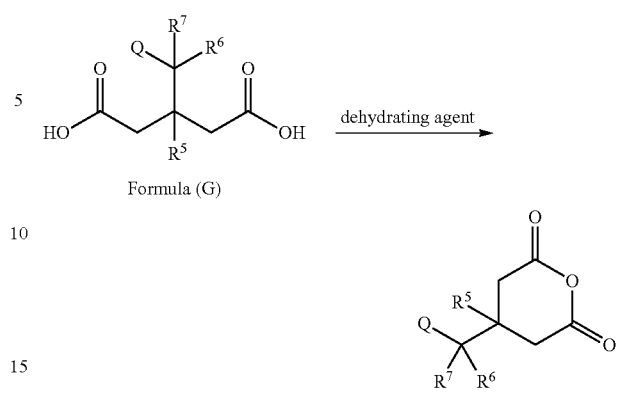

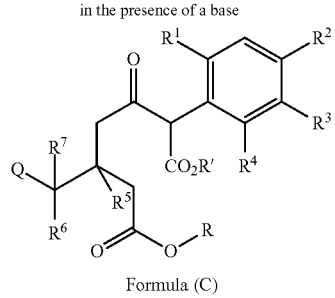

Compounds of Formula (D) are known compounds, or may be prepared from known compounds by known methods.

A compound of Formula (E) may be prepared from a compound of Formula (F) by treatment with an alcohol, R—OH, followed by treatment of the resulting acid with a chlorinating reagent such as oxalyl chloride or thionyl chloride under known conditions (see, for example, C. S. Rouvier. Tetrahedron Lett., 1984, 25, (39), 4371; D. M. Walba and M. D. Wand, *Tetrahedron Lett.*, 1982, 23, 4995; J. Cason, Org. Synth. Coll. Vol. III, 169, 1955).

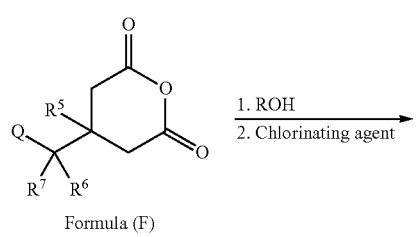

A compound of Formula (F) may be prepared by treating a compound of Formula (G) with a dehydrating agent such as an acid anhydride (as described, for example by J. Cason, Org. Synth. Coll. Vol. IV, 630, 1963). A preferred acid anhydride is acetic anhydride.

A compound of Formula (G) may be prepared by hydrolysis of a ester of Formula (H), wherein R" and R'" are suitable alkyl groups followed by decarboxylation of resulting acid. Suitable alkyl groups are $C_1$-$C_6$alkyl, especially methyl or ethyl. Suitable methods for effecting hydrolysis are known, and include, for example, treating an ester of Formula (H) with an aqueous solution of a suitable base such as sodium hydroxide or lithium hydroxide, and acidifying the reaction mixture with an acid such as hydrochloric acid to promote decarboxylation.

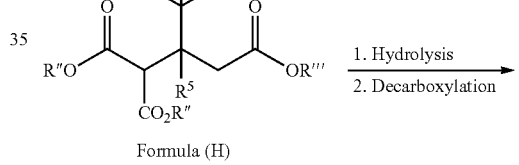

A compound of Formula (H) may be prepared by reacting a compound of Formula (J) with a dialkyl malonate, such as dimethyl malonate or diethyl malonate, under basic conditions. Preferred bases include sodium alkoxide bases such as sodium methoxide and sodium ethoxide, and the reaction is preferably carried out in a solvent such as methanol, ethanol or toluene.

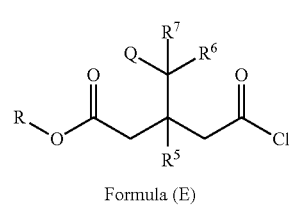

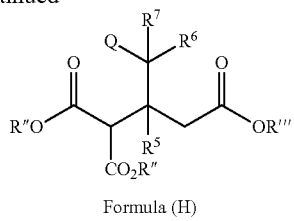

Formula (H)

Compounds of Formula J are known compounds, or may be prepared from known compounds by known methods.

A compound of Formula (B) wherein R and $R^5$ are both H may also be prepared via the hydrolysis and decarboxylation of a compound of Formula (K), which in turn is prepared by addition of a dialkyl malonate (preferably dimethyl malonate or diethyl malonate) to a compound of Formula (L) in the presence of a suitable base, such as sodium methoxide or sodium ethoxide in a suitable solvent such as methanol, ethanol or toluene. A compound of Formula (L) may be prepared by the Knoevenagel condensation of an aldehyde of Formula (M) with a 3-ketoester of Formula (N) according to known procedures. A compound of Formula N may be prepared from a compound of Formula (D), wherein R is H, through conversion to the corresponding acid chloride and subsequent reaction to give the β-ketoester of Formula (N) according to procedures described in the literature (see, for example, J. Wemple et al., Synthesis, 1993, 290-292; J. Bowman, J. Chem. Soc., 1950, 322).

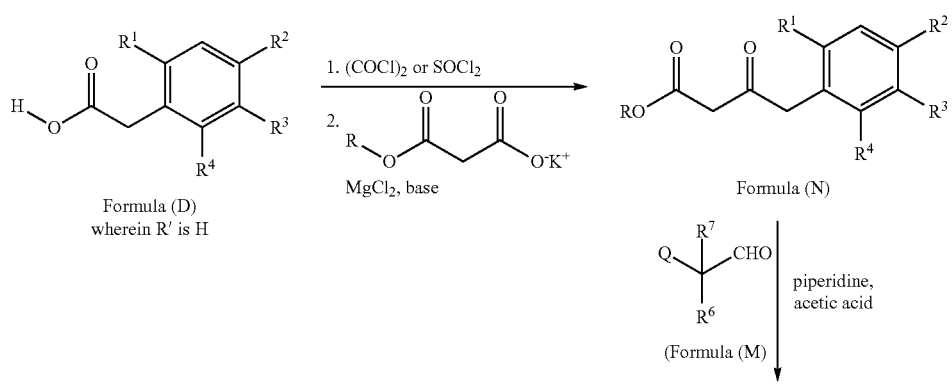

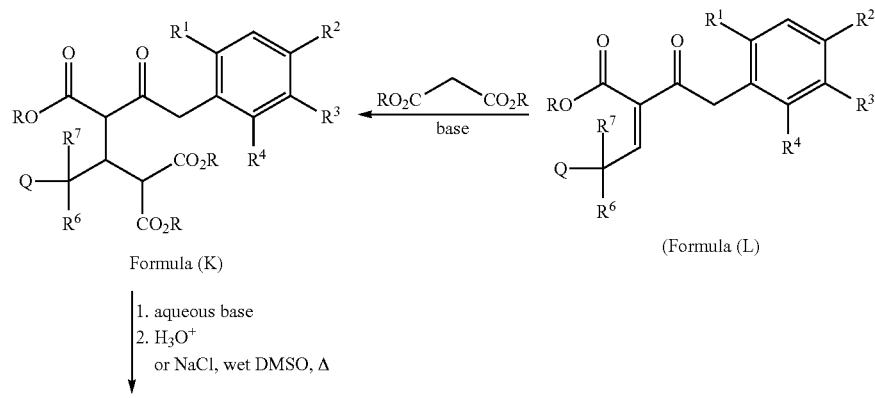

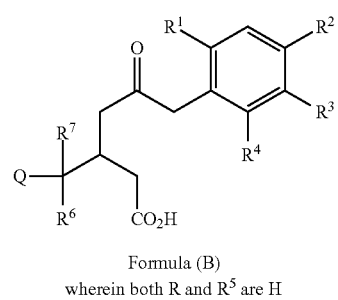

Formula (B)
wherein both R and $R^5$ are H

Compounds of Formula (M) are known compounds, or may be prepared from known compounds by known methods.

Additional compounds of Formula (A) may be prepared by reacting a 2-diazocyclo-hexane-1,3-dione of Formula (O) with a compound of Formula (P) under known conditions. Suitable procedures include the photosensitised decomposition of diazoketones (see, for example, T. N. Wheeler, J. Org. Chem., 44, 4906, 1979), or by using a suitable metal catalyst such as rhodium acetate, copper chloride or copper triflate in a suitable solvent under known conditions (see, for example, M. Oda et al., Chem. Lett. 1263, 1987). Where compounds of Formula (P) are liquids at room temperature, these reactions may be effected in the absence of any solvent. Compounds of Formula P are known, or may be prepared from known compounds by known methods.

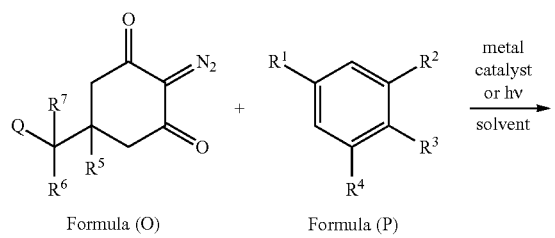

Formula (O)   Formula (P)

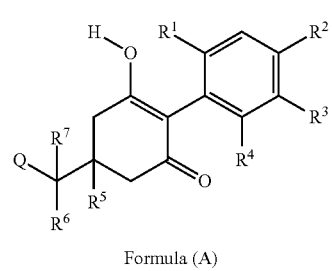

Formula (A)

A compound of Formula (O) may be prepared through treatment of a compound of Formula (Q) with a diazo transfer reagent such as tosyl azide or mesyl azide and a base, as described, for example, by T. Ye and M. A. McKervey (Chem. Rev., 1994, 94, 1091-1160), by H. Stetter and K. Kiehs (Chem. Ber., 98, 1181, 1965) and by D. F. Taber et al. (J. Org. Chem., 1986, 51, 4077).

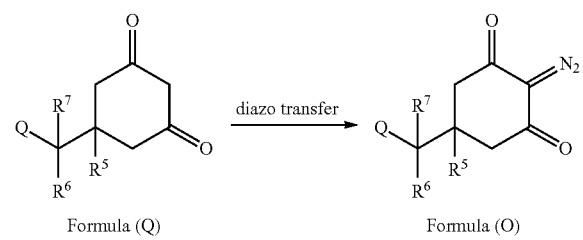

Formula (Q)   Formula (O)

The compounds of the formula (Q) have been specifically designed as intermediates for the synthesis of the compounds of the formula (I).

A compound of Formula (Q) may be prepared via the hydrolysis and decarboxylation of a compound of Formula (R), wherein R is alkyl, under known conditions. Preferably R'''' is methyl or ethyl.

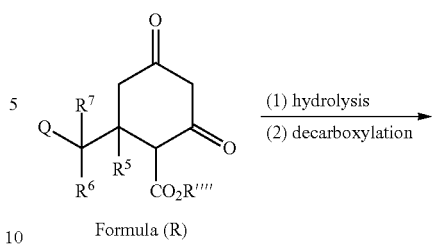

Formula (R)

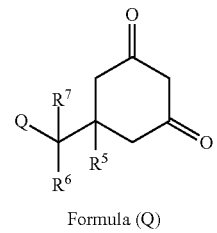

Formula (Q)

A compound of Formula (R) may be prepared by reacting a compound of Formula (S) with a dialkyl malonate under basic conditions. Preferably the dialkyl malonate is dimethyl malonate or diethyl malonate, the base is a metal alkoxide such as sodium methoxide or sodium ethoxide and the reaction is carried out in a suitable solvent such as methanol, ethanol or toluene.

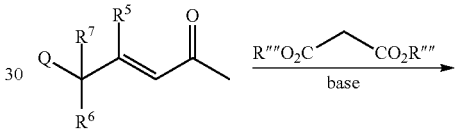

Formula (S)

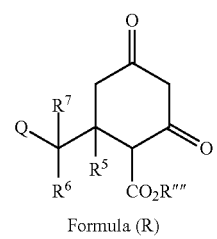

Formula (R)

Compounds of Formula (S) are known, or may be prepared by known methods from known compounds.

Additional compounds of Formula (Q), wherein $R^5$ is H, may be prepared via the reduction of compounds of Formula (T), followed by acid catalysed hydrolysis of the resulting enol ethers of Formula (U). A preferred method for effecting the reduction of a compound of Formula (T) is through the use of an alkali metal (such as lithium or sodium) in a suitable amine solvent (such as ammonia), and in the presence of an alcohol, (such as methanol, ethanol or tert-butanol) according to procedures described by, for example, E. M. Kaiser (Synthesis, 1972, 391, and references therein) and by C. F. Masauger and E Ravina (Tetrahedron Lett., 1996, 37 (No 29), 5171.

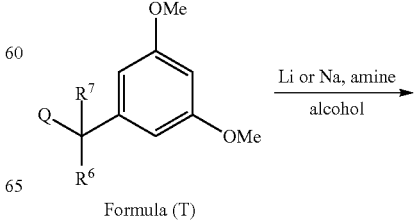

Formula (T)

-continued

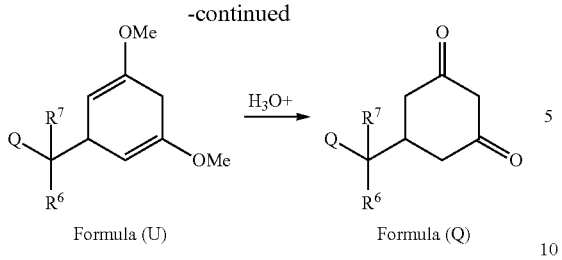

A compound of Formula (T), wherein $R^7$ is hydrogen, may be prepared by the reduction of a compound of Formula (V) under known conditions, for example by catalytic hydrogenation. A compound of Formula (V) may be also be converted to a compound of Formula (U), wherein $R^7$ is hydrogen, using an alkali metal (such as lithium or sodium) in a suitable amine solvent (such as ammonia), and in the presence of an alcohol (such as methanol or ethanol).

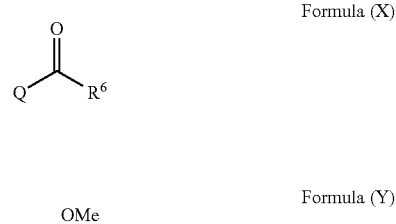

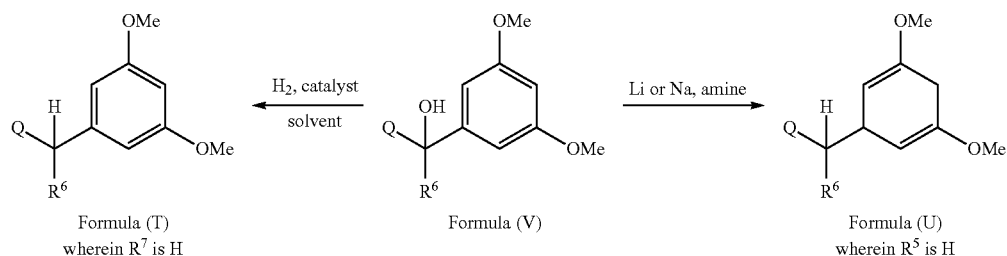

A compound of Formula (V) may be prepared by the addition of a Grignard reagent of Formula (W) wherein Hal is chlorine, bromine or iodine to a compound of Formula (X) in a suitable solvent. Preferably the Grignard reagent is 3,5-dimethoxyphenylmagnesium chloride and the solvent is tetrahydrofuran or diethyl ether.

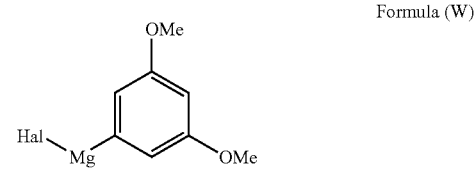

A compound of Formula (V) may also be prepared by reacting an organo-lithium compound, Q-Li, or an organomagnesium reagent, Q-Mg-Hal (where Hal is chlorine, bromine or iodine), with a compound of Formula (Y) in a suitable solvent such as tetrahydrofuran or diethyl ether.

Compounds of Formula (X) and compounds of Formula (Y) are known compounds, or may be prepared from known compounds by known method A compound of Formula (T), wherein $R^7$ is hydrogen, may also be prepared by the reduction of a styrene of Formula (Z) wherein $A^1$ and $A^2$ together form a suitable heterocyclic ring. A preferred method for reducing the styrene is by hydrogenation over a suitable palladium catalyst under known conditions.

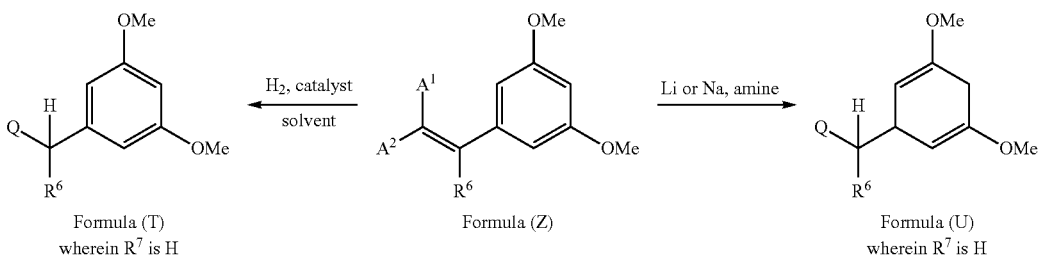

A compound of Formula (U), wherein $R^7$ is H, may also be prepared from a compound of Formula (Z) by reduction by an alkali metal (preferably lithium or sodium) in a suitable amine solvent, preferably ammonia, in the presence of an alcohol such as methanol, ethanol or tert-butanol.

A compound of Formula (Z) may be prepared by the dehydration of a compound of Formula (AA), preferably under acidic conditions. A compound of Formula (AA) may be prepared by reacting a compound of Formula (AB) with a Grignard reagent of Formula (W) wherein Hal is chlorine, bromine or iodine (and is preferably chlorine) in a suitable solvent such as diethyl ether or tetrahydrofuran.

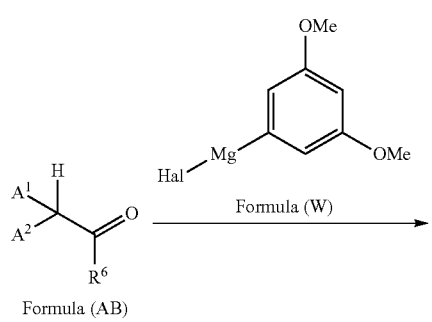

Formula (AB)

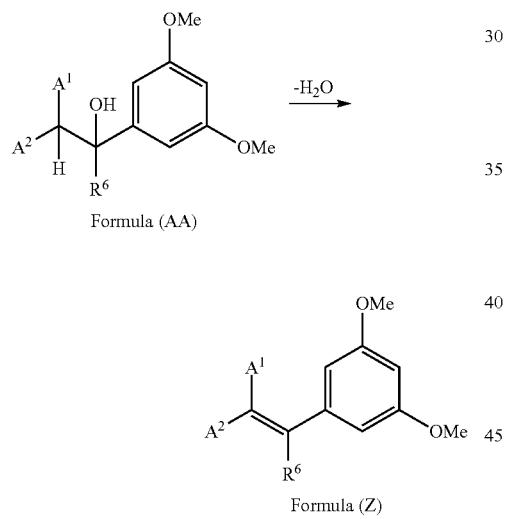

Formula (AA)

Formula (Z)

Compounds of Formula (AB) are known compounds, or may be prepared from known compounds by known methods.

A compound of Formula (Z) wherein $R^6$ is hydrogen, may also be prepared by the reaction between a compound of Formula (AC), and a phosphonate of Formula (AD) wherein R''''' is alkyl (preferably methyl or ethyl) in the presence of a suitable base such as sodium hydride, lithium hexamethylsilazide, or n-butyl lithium and a suitable solvent such as tetrahydrofuran or toluene.

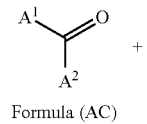

Formula (AC)

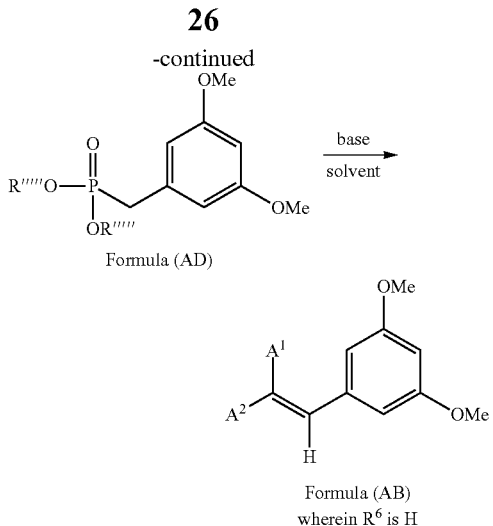

Formula (AD)

Formula (AB) wherein $R^6$ is H

Further compounds of Formula (AB) may be prepared by reacting a Grignard reagent of Formula (AE) wherein Hal is chlorine, bromine or iodine, with a compound of Formula AC, in a suitable solvent such as tetrahydrofuran or diethyl ether, followed by dehydration of the resulting alcohol of Formula (AF).

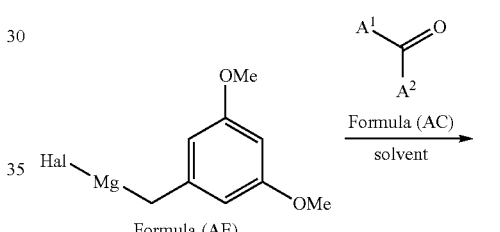

Formula (AE)  Formula (AC)

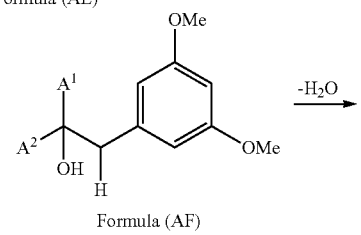

Formula (AF)

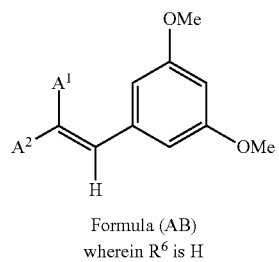

Formula (AB) wherein $R^6$ is H

Compounds of Formula (AC), compounds of Formula (AD) and compounds of Formula (AE) are known compounds, or may be prepared from known compounds by known methods.

Additional compounds of Formula (A) may be prepared by reacting an iodonium ylide of Formula (AG), wherein Ar is an optionally substituted phenyl group, and an aryl boronic acid of Formula (AH) in the presence of a suitable palladium catalyst, a base and in a suitable solvent.

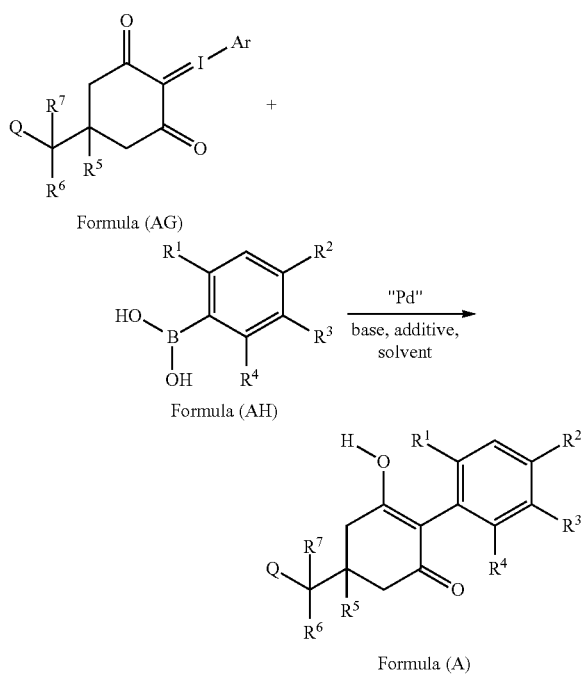

Formula (AG)

Formula (AH)

Formula (A)

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis (dibenzylideneacetone)palladium(0) or tetrakis (triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected solvent, with a compound of Formula (AG), the arylboronic acid of Formula (AH), and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C-C coupling reaction is thus formed "in situ", and then initiates the C-C coupling reaction.

The palladium catalysts are used in an amount of from 0.001 to 50 mol %, preferably in an amount of from 0.1 to 15 mol %, based on the compound of Formula (AG). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of Formula (AG) may be prepared from a compound of Formula (Q) by treatment with (diacetoxy) iodobenzene and a base such as aqueous sodium carbonate, lithium hydroxide or sodium hydroxide in a solvent such as water or an aqueous alcohol such as aqueous ethanol according to the procedures of K Schank and C Lick, Synthesis, 392 (1983), or of Z Yang et al., Org. Lett., 2002, 4 (no 19), 3333:

An aryl boronic acid of Formula (AH) may be prepared from an aryl halide of Formula (AJ), wherein Hal is bromine or iodine, by known methods (see, for example, W. J. Thompson and J. Gaudino, J. Org. Chem., 1984, 49, 5237 and R. T. Hawkins et al., J. Am. Chem. Soc., 1960, 82, 3053). For example, an aryl halide of Formula (AJ) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained is then reacted with a trialkyl borate (preferably trimethylborate) to give an aryl dialkylboronate which may be hydrolysed to the desired boronic acid of Formula (AH) under acidic conditions.

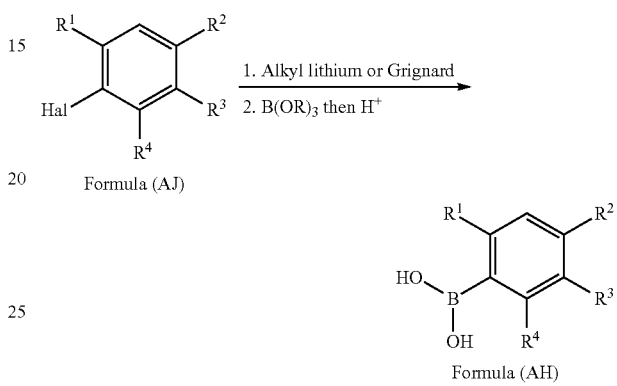

Formula (AJ)

Formula (AH)

Aryl halides of Formula (AJ) may be prepared from anilines of Formula (AK) by known methods, for example the Sandmeyer reaction, via the corresponding diazonium salts.

Anilines of Formula (AK) are known compounds, or may be made from known compounds, by known methods.

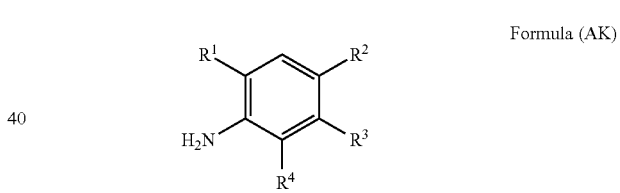

Formula (AK)

Additional compounds of Formula (A) wherein $R^2$ is optionally substituted aryl or heteroaryl may be prepared from compounds of Formula (AL) wherein $X^1$ is an atom or group suitable for cross-coupling with an aryl- or heteroarylboronic acid in the presence of a suitable palladium catalyst and a base under known conditions (see, for example F. Bellina, A. Carpita and R. Rossi, Synthesis 2004, 15, 2419-2440 and A. Suzuki, Journal of Organometallic Chemistry, 2002, 653, 83). Suitable atoms and groups $X^1$ include triflates, especially trifluoromethanesulfonyloxy- and halogens, especially chlorine, bromine and iodine.

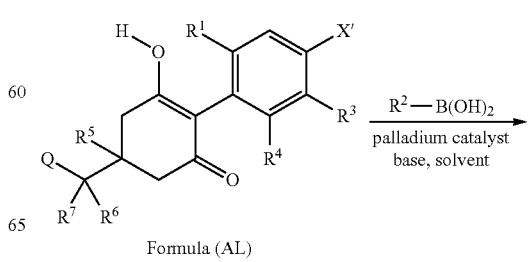

Formula (AL)

-continued

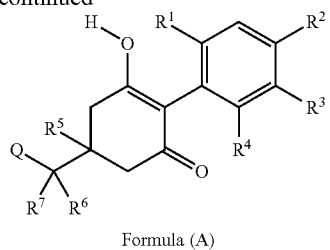

Formula (A)

In the same way, a compound of Formula (A) wherein $R^3$ is optionally substituted aryl or heteroaryl may be prepared from a compound of Formula (AM) wherein $X^1$ is as defined previously and a suitable aryl- or heteroaryl boronic acid under palladium catalysed conditions.

Compounds of Formula (AL) and Formula (AM) may be prepared from Compounds of Formula (AN) and Formula (AO) respectively, by one or more of the procedures described previously.

Compounds of Formula (AN) and Formula (AO) may be prepared from known compounds by known methods.

A compound of Formula (AL) may also be prepared by reacting a compound of Formula (O) with a compound of Formula (AP) under similar conditions to those described above for the conversion of a compound of Formula (O) to a compound of Formula (A).

In the same way, a compound of Formula (AM) may be prepared from a compound of Formula (O) and a Compound of Formula (AQ) under identical conditions.

In a further approach, a compound of formula (A), may be prepared from a compound (Q) by treatment with an aryllead tricarboxylate, in the presence of a suitable ligand and in a suitable solvent. Similar reactions are described in the literature (for example see, J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (AR).

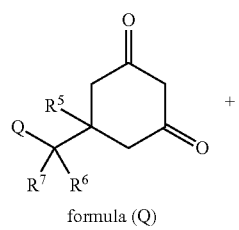

formula (Q)

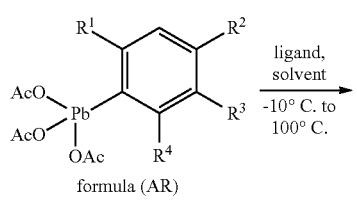

formula (AR)

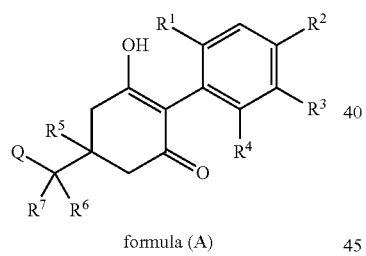

formula (A)

Preferably the ligand is a nitrogen containing heterocycle such as N,N-dimethylamino-pyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

A compound of formula (AR) may be prepared from a compound of formula (AH) by treatment with lead tetraacetate in a suitable solvent (for example chloroform) at 25° C. to 10° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

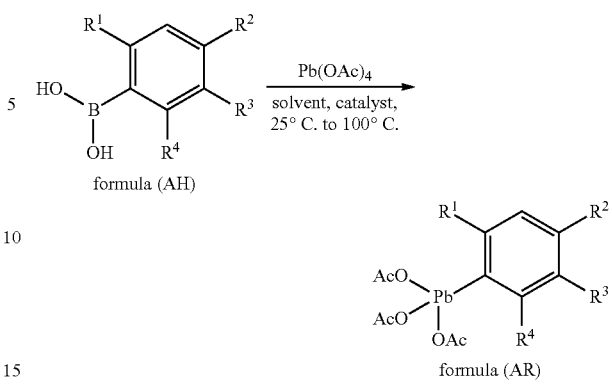

formula (AH)

formula (AR)

In the same way, a compound of formula (AL) may be prepared by treating a compound of formula (O) with an aryllead triacetate of formula (AS)—itself derived from an arylboronic acid of formula (AT).

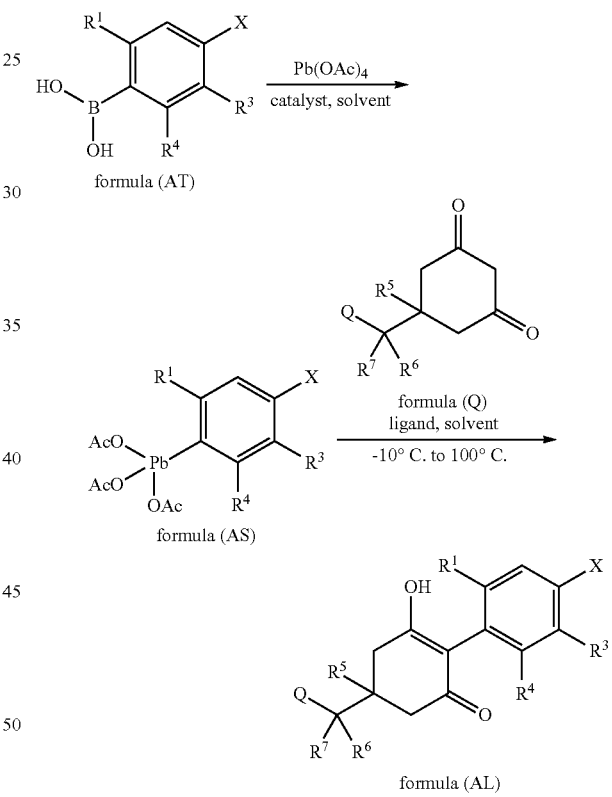

formula (AT)

formula (AS)

formula (AL)

A compound of formula (AM) may be similarly prepared from an arylboronic acid of formula (AU) via an aryllead triacetate of formula (AV).

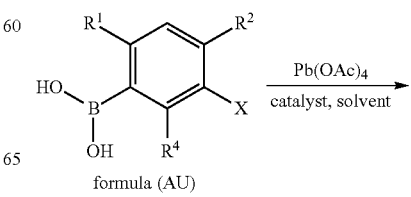

formula (AU)

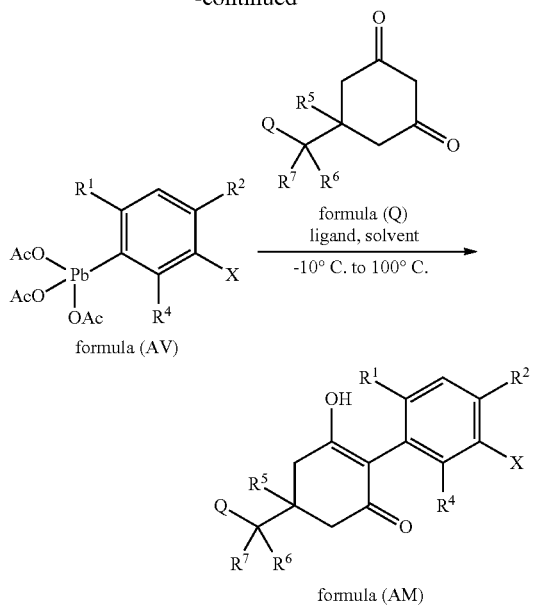

Arylboronic acids of formula (AT), and of formula (AU), are known compounds, or may be made by known methods from known compounds.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:

(%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |

| Dusts: | |
|---|---|
| active ingredient: | 0.1 to 10%, preferably 0.1 to 5% |
| solid carrier: | 99.9 to 90%, preferably 99.9 to 99% |

| Suspension concentrates: | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

-continued

| Wettable powders: | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

| Granules: | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include especially cereals, cotton, soybeans, sugar beet, sugar cane, plantation crops, rape, maize and rice, and for non-selective weed control. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imid-azolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important.

Preferably, in these mixtures, the compound of the formula I is one of those compounds listed in Tables 1 to 81 below: compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners of the compound of formula I may also be in the form of esters or salts, as mentioned e.g. in The Pesticide Manual, Twelfth Edition, British Crop Protection Council, 2000.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

The compounds of formula I according to the invention can also be used in combination with safeners. Preferably, in these mixtures, the compound of the formula I is one of those compounds listed in Tables 1 to 81 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein and PPG-1292 is known from WO09211761.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The mixtures can advantageously be used in the above-mentioned formulations (in which case "active ingredient" relates to the respective mixture of compound of formula I with the mixing partner).

The following Examples illustrate the invention further but do not limit the invention.

PREPARATION EXAMPLES

Example 1

Preparation of 2-(2,4,6-trimethylphenyl)-5-(tetrahydrofuran-3-ylmethyl)cyclohexane-1,3-dione

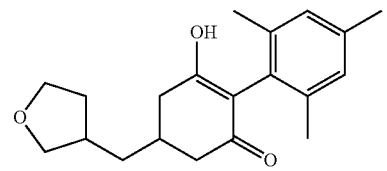 [SMILES: Cc1cc(C)c(C2=C(O)CC(CC3CCOC3)CC2=O)c(C)c1]

Step 1

Preparation of (3,5-dimethoxyphenyl)(tetrahydrofuran-3-yl)methanol

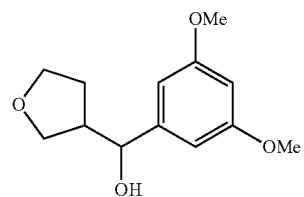 [SMILES: COc1cc(OC)cc(C(O)C2CCOC2)c1]

Magnesium turnings (8.5 g, 0.35 mol) are activated by stirring at room temperature overnight under argon and suspended in anhydrous tetrahydrofuran (60 ml). 10 ml of a solution of 3,5-dimethoxychlorobenzene (60.4 g, 0.35 mol) in anhydrous tetrahydrofuran (75 mL) is added, followed by a crystal of iodine, and the mixture is placed in an ultrasonic bath for 10 minutes. A further 10 mL of the solution of 3,5-dimethoxychlorobenzene in tetrahydrofuran is added and reaction is heated at 80° C. for 1 h. The remainder of the starting material is added dropwise to the reaction mixture at 80° C. over 50 minutes, then heating is continued at 80° C. for a further 30 minutes. The reaction mixture is cooled to below room temperature in an ice/water bath and a solution of tetrahydrofuran-3-carbaldehyde (35 g, 0.35 mol) in anhydrous tetrahydrofuran (35 mL) is added dropwise over 30 minutes. Once the addition is complete, the reaction mixture is stirred at room temperature overnight. The reaction mixture is decanted and 2M aqueous hydrochloric acid is carefully added to the decanted solution, until the pH of the reaction mixture reaches pH 1. The reaction mixture is extracted with ethyl acetate (4×100 mL) and the organic extracts are combined, washed with brine, dried over anhydrous magnesium sulfate, filtered and the filtrate concentrated in vacuo. The residue is purified by column chromatography on silica gel to give (3,5-dimethoxyphenyl)(tetrahydrofuran-3-yl)methanol as a yellow oil.

$^1$H NMR (CDCl$_3$, ppm) δ 6.51 (dd, 2H), 6.39 (q, 1H), 4.46 (dd, 1H), 3.98-3.84 (m, 2H), 3.80 (s, 3H), 3.79 (s, 3H), 3.77-3.47 (m, 2H), 2.65-2.55 (m, 1H), 2.12-1.96 (m, 2H)

Step 2

Preparation of 5-(tetrahydrofuran-3-ylmethyl)cyclohexane-1,3-dione

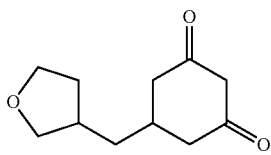 [SMILES: O=C1CC(=O)CC(CC2CCOC2)C1]

Liquid ammonia (~300 mL) is added to a cold (−78° C.) 500 mL three-necked round bottomed flask fitted with a cold finger, under a blanket of nitrogen. A solution of (3,5-dimethoxyphenyl)(tetrahydrofuran-3-yl)methanol (10.0 g, 42 mmol) in ethanol (10 mL) is added. Lithium wire is added in ~100 mg pieces until a blue colour persists for several minutes. When the blue colour fades, more ethanol (5 mL) is added, together with further portions of lithium wire (~100 mg portions) and this process is repeated until the reaction is judged to be complete (conveniently by mass spectrometric analysis). The reaction mixture is allowed to warm to room temperature, and once the ammonia is evaporated, a saturated solution of aqueous ammonium chloride (150 mL) is added, followed by ethyl acetate (150 mL) and the mixture is stirred until the off-white solid dissolves. The reaction mixture is poured into a separating funnel, the layers are separated and the aqueous layer is extracted with ethyl acetate. The organic extracts are combined, dried over anhydrous magnesium sulfate, filtered and the filtrate concentrated in vacuo.

The residue is stirred overnight at room temperature in a mixture of tetrahydrofuran (100 ml) and 2M aqueous hydrochloric acid (100 mL), then extracted into ethyl acetate. The organic extracts are washed with brine, dried over anhydrous magnesium sulfate, filtered and the filtrate concentrated in vacuo to give 5-(tetrahydrofuran-3-ylmethyl)cyclohexane-1,3-dione as an off-white solid, used without further purification in the next step.

Step 3

Preparation of 2-(2,4,6-trimethylphenyl)-5-(tetrahydrofuran-3-ylmethyl)cyclohexane-1,3-dione

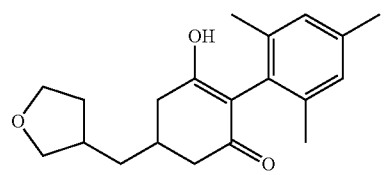 [SMILES: Cc1cc(C)c(C2=C(O)CC(CC3CCOC3)CC2=O)c(C)c1]

Step 3a

Iodobenzene diacetate (11.5 g, 35.6 mmol) and sodium carbonate (3.8 g, 35.6 mmol) are suspended in water (70 mL) and stirred at room temperature for 30 minutes. Meanwhile, a solution of sodium carbonate (3.8 g, 35.6 mmol) in water (70 mL) is added to 5-(tetrahydro-furan-3-ylmethyl)cyclohexane-1,3-dione (7.0 g, 35.6 mmol) and this mixture is stirred for 20 minutes to produce a sparingly soluble orange suspension. The two reaction mixtures are then combined and the mixture stirred at room temperature for 3 hours. The solid precipitate is removed by filtration, and the filtrate is extracted with dichloromethane. The organic extracts are dried over anhydrous magnesium sulfate, filtered and the filtrate concentrated in vacuo to give a yellow oil. The oil is triturated with ether and filtered to give the desired iodonium ylide as a yellow solid.

$^1$H NMR (CDCl$_3$, ppm) δ 7.84 (dd, 2H), 7.53 (m, 1H), 7.36 (t, 2H), 3.89 (t, 1H), 3.83 (m, 1H), 3.73 (q, 1H), 3.29 (t, 1H), 2.76-2.71 (m, 2H), 2.37-2.24 (m, 3H), 2.12-2.00 (m, 2H), 1.51-1.42 (m, 3H).

Step 3b

The iodonium ylide (1.5 g, 3.77 mmol) prepared in Step 3a is suspended in a mixture of 1,2-dimethoxyethane (40 ml) and water (10 mL). 2,4,6-Trimethylphenylboronic acid (0.54 g, 4.14 mmol) is added, followed by lithium hydroxide monohydrate (0.48 g, 11.3 mmol), tetrabutylammonium bromide (1.25 g, 3.77 mmol) and palladium (II) acetate (0.042 g, 0.21 mmol) and the mixture is heated at 50-52° C. for 6 h 30 and then allowed to cool to room temperature. The reaction mixture is acidified with 2N aqueous hydrochloric acid, and then extracted into ethyl acetate. The organic extracts are combined and partitioned with 0.5M aqueous potassium carbonate solution. The organic phase is discarded. The aqueous phase is acidified to pH 1 with concentrated hydrochloric acid and extracted with ethyl acetate. The organic extracts are combined, dried over anhydrous magnesium sulfate, filtered and the filtrate concentrated in vacuo. The residue is purified by column chromatography on silica gel to give 2-(2,4,6-trimethylphenyl)-5-(tetrahydrofuran-3-ylmethyl)cyclohexane-1,3-dione as a pale yellow solid, m.p. 62-64° C.

$^1$H NMR (CDCl$_3$, ppm) δ 6.94 (s, 2H), 5.50 (br s, 1H), 3.96 (br t, 1H), 3.89 (m, 1H), 3.78 (q, 1H), 3.36 (t, 1H), 2.71-2.66 (br m, 2H), 2.44-2.22 (m, 7H), 2.09-2.03 (m, 7H), 1.60-1.50 (br m, 3H).

Example 2

Preparation of 2-(2,6-diethyl-4-methylphenyl)-5-(tetrahydropyran-4-ylmethyl)cyclohexane-1,3-dione

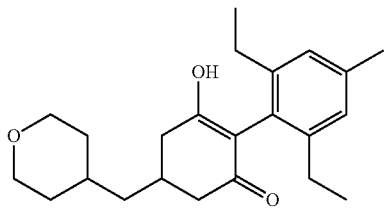 [SMILES: CCc1cc(C)cc(CC)c1C1=C(O)CC(CC2CCOCC2)CC1=O]

Step 1

Preparation of 4-(methoxymethylene)tetrahydropyran

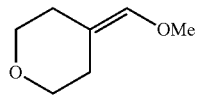

Methoxymethyltriphenylphosphonium chloride (81.8 g) is suspended in dry THF (200 ml) and stirred under nitrogen at 0° C. A 1 molar solution of lithium bis(trimethylsilyl)amide in THF (239 ml) is transferred to a dropping funnel by cannular under nitrogen and added over 20 minutes.

The resulting red-brown solution is stirred at 0-20° C. for 1 hour. The mixture is then cooled to −25° C. and tetrahydro-4H-pyran-4-one (20 ml) is added over 10 minutes. The cooling bath is removed and the mixture is allowed to reach room temperature, then stirred for 22 hours. The reaction mixture is poured into water (400 ml) and extracted into ether (2×400 ml). The organic extracts are combined, washed with water (2×400 ml) and brine (400 ml), dried over anhydrous magnesium sulfate, filtered and the filtrate is concentrated in vacuo. The residue is treated with 800 ml ether:hexane (1:1), stirred for 15 mins, then cooled in an ice bath for 10 mins and filtered under vacuum to remove the precipitated triphenylphosphine oxide. The filtrate is concentrated, treated again with 400 ml ether:hexane (1:1), stirred for 15 minutes, then cooled in an ice bath and additional precipitate removed by filtration. The filtrate is concentrated giving 25.371 g of a brown oil, which is further purified by vacuum distillation to afford 4-(methoxymethylene)-tetrahydropyran (b.p. 66° C./20 mmHg)

$^1$H NMR (CDCl$_3$, ppm) δ 5.82 (s, 1H), 3.61 (m, 4H), 3.53 (s, 3H), 2.28 (t, 2H), 2.04 (t, 2H)

Step 2

Preparation of tetrahydropyran-4-carboxaldehyde

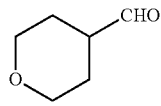

A mixture of 4-(methoxymethylene)tetrahydropyran (17.18 g, 134 mmol) and toluene-4-sulphonic acid hydrate (35.76 g, 188 mmol) in a mixture of water (90 ml) and THF (90 ml) is stirred at room temperature for 4½ hours. The mixture is treated with a saturated aqueous solution of NaHCO$_3$ (300 ml) and stirred until effervescence ceased. The mixture is transferred to a separating funnel, brine (100 ml) is added, and the mixture is partitioned with dichloromethane (4×150 ml). The organic extracts are combined, dried over anhydrous magnesium sulfate, filtered and the filtrate concentrated in vacuo to afford tetrahydropyran-4-carboxaldehyde.

$^1$H NMR (CDCl$_3$, ppm) δ$_H$ 9.61 (s, 1H), 3.92 (m, 2H), 3.45 (m, 2H), 2.50-2.43 (m, 1H), 1.85-1.79 (m, 2H), 1.70-1.61 (m, 2H).

Step 3

Preparation of (3,5-dimethoxyphenyl)(tetrahydropyran-4-yl)methanol

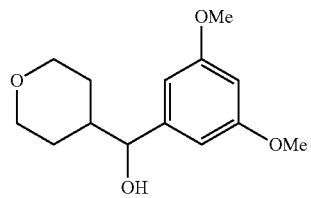 [SMILES: COc1cc(OC)cc(C(O)C2CCOCC2)c1]

A solution of tetrahydropyran-4-carboxaldehyde (16.0 g, 0.14 mol) in tetrahydrofuran (60 ml) is added dropwise over 1 hour to a 1 M solution of 3,5-dimethoxyphenylmagnesium chloride in tetrahydrofuran (140 ml), maintaining the reaction at or below reflux by external cooling. Once the addition is complete, and the exotherm has subsided, the reaction mixture is allowed to stir at room temperature overnight. A solution of dilute aqueous hydrochloric acid (300 ml) is added carefully and the reaction mixture is extracted with ethyl acetate. The organic extract is dried over anhydrous magnesium sulfate, filtered, and the filtrate evaporated in vacuo. Purification by column chromatography on silica gel gives (3,5-dimethoxyphenyl) (tetrahydropyran-4-yl)methanol as a cream solid.

$^1$H NMR (CDCl$_3$, ppm) δ 6.47 (d, 2H), 6.38 (t, 1H), 4.29 (d, 1H), 4.01 (dd, 1H), 3.90 (dd, 1H), 3.36 (m, 1H), 3.29 (m, 1H), 1.96 (br s, 1H), 1.92-1.87 (m, 1H), 1.83-1.77 (m, 1H), 1.51-1.18 (m, 3H).

Step 4

Preparation of 5-(tetrahydropyran-4-ylmethyl)cyclohexane-1,3-dione

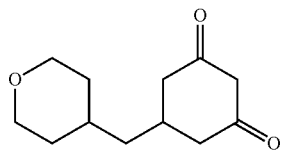 [SMILES: O=C1CC(=O)CC(CC2CCOCC2)C1]

Ammonia (pre-dried using sodium and iron (III) chloride) (approx 200 mL) is allowed to distil into a flask containing (3,5-dimethoxyphenyl) (tetrahydropyran-4-yl)methanol (308 mg, 1.3 mmol) in ethanol (2 mL), and lithium wire is added portionwise to the reaction mixture until the reaction mixture retains a blue colour. A further quantity of ethanol (~2 mL) is then added, followed by the addition of a further small quantity of lithium, and the reaction mixture stirred until the blue colour persists for a few minutes. The ammonia is evaporated, and the resultant white solution is taken up into saturated aqueous ammonium chloride solution, and extracted with ethyl acetate. The organic extracts are washed with brine, dried over anhydrous magnesium sulfate, filtered and the filtrate concentrated in vacuo.

The residue is dissolved in a 1:1 mixture of tetrahydrofuran and dilute aqueous hydrochloric acid (50 mL) and the reaction mixture is stirred at room temperature overnight. The reaction is extracted into ethyl acetate and the organic extracts are combined, washed with brine, dried over anhydrous magnesium sulfate, filtered and the filtrate is concentrated in vacuo to give a white solid. Recrystallisation from ethyl acetate/hexane gives 5-(tetrahydropyran-4-ylmethyl)cyclohexane-1,3-dione as a white solid, m.p. 129-130° C.

Step 5

Preparation of

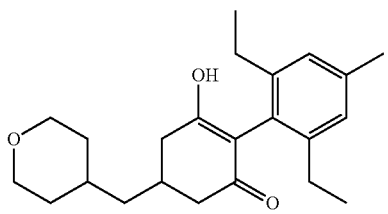 [SMILES: CCc1cc(C)cc(CC)c1C1=C(O)CC(CC2CCOCC2)CC1=O]

Step 5a

Iodobenzene diacetate (184 mg, 0.57 mmol) and sodium carbonate (60 mg, 0.57 mmol) are suspended in water (20 mL) and the mixture is stirred at room temperature for 30 minutes to give a pale yellow suspension. Meanwhile, a solution of sodium carbonate (60 mg, 0.57 mmol) in water (10 mL) and ethanol (10 mL) is added to 5-(tetrahydropyran-4-ylmethyl)cyclohexane-1,3-dione (120 mg, 0.57 mmol) and the reaction is stirred at room temperature for 20 minutes. The two mixtures are then combined and the reaction mixture is stirred at room temperature for 1 hour. The reaction mixture is then partitioned between brine and dichloromethane, and the organic extracts are combined, dried over anhydrous magnesium sulfate, filtered and the filtrate evaporated in vacuo to give the desired iodonium ylide, used without further purification in the next step.

$^1$H NMR (CDCl$_3$, ppm) $\delta_H$ 7.79-7.76 (m, 2H), 7.46 (m, 1H), 7.33-7.24 (m, 2H), 3.86 (dd, 2H), 3.28 (m, 2H), 2.63 (dd, 2H), 2.26-2.11 (m, 3H), 1.56-1.47 (m, 3H), 1.23 (t, 2H), 1.21-1.11 (m, 2H).

Step 5b

The iodonium ylide (193 mg, 0.47 mmol) prepared in Step 5a is added to a mixture of 2,6-diethyl-4-methylphenylboronic acid (90 mg, 0.47 mmol), tetrabutylammonium bromide (151 mg, 0.47 mmol), lithium hydroxide monohydrate (60 mg, 1.4 mmol) and palladium (II) acetate (catalytic amount) in aqueous 1,2-dimethoxyethane and the reaction mixture is heated at 50° C. for 3 hours. The reaction is then cooled, dilute aqueous hydrochloric acid is added, and the mixture is extracted with ethyl acetate. The organic extracts are combined, dried over anhydrous magnesium sulfate, filtered and the filtrate is concentrated in vacuo. The residue is purified by column chromatography on silica gel to give 2-(2,6-diethyl-4-methylphenyl)-5-(tetrahydropyran-4-ylmethyl)cyclohexane-1,3-dione $^1$H NMR (CDCl$_3$, ppm) $\delta$ 7.0 (s, 2H), 5.50 (br s, 1H), 3.98 (br dd, 2H), 3.40 (br t, 2H), 2.68-2.63 (m, 2H), 2.45-2.25 (m, 10H), 1.69-1.55 (m, 3H), 1.44 (br t, 2H), 1.35-1.20 (m, 2H), 1.08 (q, 6H).

Example 3

Preparation of 2-(2,6-diethyl-4-methylphenyl)-5-([1,3]dioxolan-2-ylmethyl)cyclohexane-1,3-dione (Compound A-6)

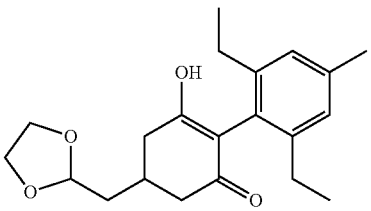 [SMILES: CCc1cc(C)cc(CC)c1C1=C(O)CC(CC2OCCO2)CC1=O]

Step 1

Preparation of 2-(3,5-dimethoxy-cyclohexa-2,5-dienylmethyl)-[1,3]-dioxolane

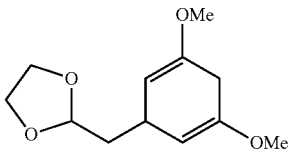 [SMILES: COC1=CC(CC2OCCO2)C=C(OC)C1]

Ammonia (pre-dried using sodium and iron (III) chloride) (approx 60 mL) is allowed to distil into a flask containing 2-(3,5-dimethoxybenzyl)-[1,3]-dioxolane (1.0 g, 4.46 mmol) in ethanol (3 mL), and lithium wire is added portionwise to the reaction mixture until the reaction mixture retains a blue colour for ten minutes. Ethanol (1 mL) is then added, and the mixture stirred for 20-25 minutes at –33° C. The ammonia is evaporated, and the resultant mixture is taken up into saturated aqueous ammonium chloride solution (20 ml), and extracted with ethyl acetate (3×25 ml). The organic extracts are washed with brine, dried over anhydrous magnesium sulfate, filtered and the filtrate concentrated in vacuo to give 2-(3,5-dimethoxy-cyclohexa-2,5-dienylmethyl)-[1,3]-dioxolane.

$^1$H NMR (CDCl$_3$, ppm) $\delta$ 5.00 (t, 1H), 4.70 (m, 2H), 4.01 and 3.89 (2×m, 4H), 3.58 (s, 6H), 3.20 (m, 1H), 2.79 (m, 2H), 1.79 (m, 2H)

Step 2

Preparation of 5-([1,3]-dioxolan-2-ylmethyl)-cyclohexane-1,3-dione

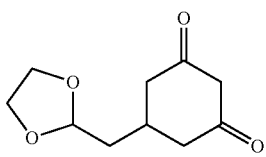 [SMILES: O=C1CC(=O)CC(CC2OCCO2)C1]

A solution of 2-(3,5-dimethoxycyclohexa-2,5-dienylmethyl)-[1,3]-dioxolane (730 mgs, 3.2 mmol) in a mixture of 10% aqueous hydrochloric acid (2.9 ml) and tetrahydrofuran (29 ml) is stirred at room temperature for ¾ hour. The reaction mixture is poured into an aqueous solution of saturated potassium carbonate and extracted with ethyl acetate. The organic extract is discarded. The aqueous extract is acidified with dilute aqueous hydrochloric acid and extracted with ethyl acetate. The organic extract is dried over anhydrous magnesium sulfate, filtered and then filtrate evaporated in vacuo to give 5-([1,3]-dioxolan-2-ylmethyl)-cyclohexane-1,3-dione as a white solid, used without further purification in the next step.

Step 3

Preparation of 2-(2,6-diethyl-4-methylphenyl)-5-([1,3]dioxolan-2-ylmethyl)cyclohexane-1,3-dione

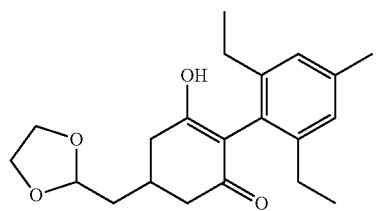 [SMILES: CCc1cc(C)cc(CC)c1C1=C(O)CC(CC2OCCO2)CC1=O]

Step 3a

Iodobenzene diacetate (454 mg, 1.4 mmol) and sodium carbonate (148 mg, 1.4 mmol) are suspended in water (6.5 mL) and the mixture is stirred at room temperature for 30 minutes. Meanwhile, a solution of sodium carbonate (148 mg, 1.4 mmol) in water (6.5 ml) and is added to 5-([1,3]-dioxolan-2-ylmethyl)cyclohexane-1,3-dione (280 mgs, 1.4 mmol) and this mixture is stirred at room temperature for 20 minutes. The two mixtures are then combined and the reaction mixture is stirred at room temperature for 2 hours. The reaction mixture is extracted with dichloromethane, and the organic extracts are combined, washed with brine, dried over anhydrous magnesium sulfate, filtered and the filtrate evaporated in vacuo to give the desired iodonium ylide, used without further purification in the next step.

Step 3b

The iodonium ylide (477 mg, 1.19 mmol) prepared in Step 3a is added to a mixture of 2,6-diethyl-4-methylphenylboronic acid (343 mg, 1.79 mmol), tetrabutylammonium bromide (385 mg, 1.19 mmol), lithium hydroxide monohydrate (151 mg, 3.57 mmol) and palladium (II) acetate (13 mgs) in a mixture of 1,2-dimethoxyethane (10.8 ml) and water (2.7 ml) and the reaction mixture is heated at 55° C. for 5 hours. The reaction is then cooled, dilute aqueous hydrochloric acid is added, and the mixture is extracted with ethyl acetate. The organic extracts are combined, washed with water, dried over anhydrous magnesium sulfate, filtered and the filtrate is concentrated in vacuo. The residue is purified by column chromatography on silica gel to give 2-(2,6-diethyl-4-methylphenyl)-5-([1,3]dioxolan-2-ylmethyl)cyclohexane-1,3-dione $^1$H NMR (CDCl$_3$, ppm) $\delta_H$ 6.98 (br s, 2H), 4.98 (t, 1H), 4.01-3.88 (2×m, 4H), 2.75 (m, 2H), 2.60-2.25 (m, 10H), 1.85 (m, 2H), 1.05 (m, 6H)

Example 4

Preparation of 2-(4'-Chloro-4-methylbiphenyl-3-yl)-5-[1,3]dioxolan-2-ylmethylcyclohexane-1,3-dione

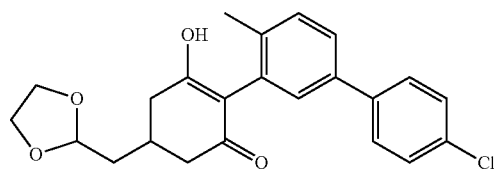 [SMILES: Cc1ccc(-c2ccc(Cl)cc2)cc1C1=C(O)CC(CC2OCCO2)CC1=O]

Step 1

Preparation of 2-(4'-Chloro-4-methylbiphenyl-3-yl)-5-[1,3]dioxolan-2-ylmethylcyclohexane-1,3-dione

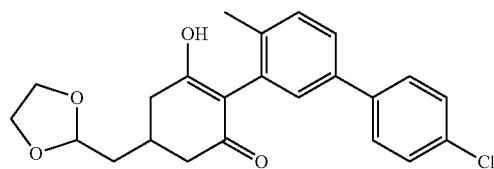 [SMILES: Cc1ccc(-c2ccc(Cl)cc2)cc1C1=C(O)CC(CC2OCCO2)CC1=O]

To a solution of 5-[1,3]dioxolan-2-ylmethylcyclohexane-1,3-dione (1.43 g, 7.22 mmol) in a mixed solvent system of chloroform (72 ml) and toluene (18 ml) is added N,N-dimethylaminopyridine (4.40 g, 36.08 mmol) and the solution is stirred at room temperature for 10 minutes. To this mixture is then added 4'-chloro-4-methylbiphenyl-3-yllead triacetate (described in WO 2008/071405) (4.95 g, 7.91 mmol) in one portion, followed by heating at 80° C. for 2 hours. After cooling to room temperature the solution is diluted with dichloromethane (90 ml) and quenched with 1M hydrochloric acid (90 ml). The resulting precipitate is filtered through celite and the residue washed with additional dichloromethane (20 ml). The biphasic solution is separated and the organic layer further washed with 1M hydrochloric acid (45 ml). Organics are finally passed through a phase separator then concentrated in vacuo to afford the crude product as a yellow oil. After flash column chromatography on silica (7:1 ethyl acetate/hexane eluant) 2-(4'-chloro-4-methylbiphenyl-3-yl)-5-[1,3]dioxolan-2-ylmethylcyclohexane-1,3-dione is afforded as a cream solid.

Example 5

Preparation of 2-(4'-Chloro-4-methylbiphenyl-3-yl)-5-[1,3]dioxan-2-ylmethylcyclohexane-1,3-dione

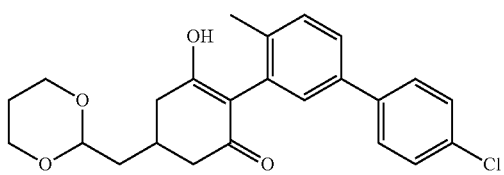 [SMILES: Cc1ccc(-c2ccc(Cl)cc2)cc1C1=C(O)CC(CC2OCCCO2)CC1=O]

Step 1

Preparation of [4-(4'-Chloro-4-methylbiphenyl-3-yl)-3,5-dioxocyclohexyl]-acetaldehyde

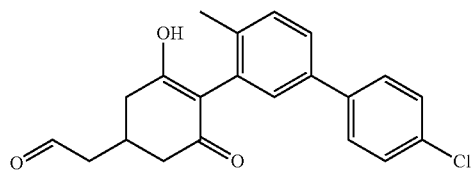 [SMILES: Cc1ccc(-c2ccc(Cl)cc2)cc1C1=C(O)CC(CC=O)CC1=O]

To a solution of 2-(4'-chloro-4-methylbiphenyl-3-yl)-5-[1,3]dioxolan-2-ylmethylcyclohexane-1,3-dione (0.275 g, 0.69 mmol) in tetrahydrofuran (5 ml) is added 6M hydrochloric acid (2 ml), and the reaction mixture is stirred at room temperature for 1.5 hours. Additional 6M hydrochloric acid (1 ml) is added and the solution is heated at 50° C. for an additional 2 hours. After cooling to room temperature the reaction mixture is concentrated and the residue partitioned between distilled water (20 ml) and dichloromethane (20 ml). After extraction of the aqueous phase with dichloromethane (3×10 ml) all organic fractions are combined then passed through a phase separator. The fitrate is concentrated in vacuo to afford [4-(4'-Chloro-4-methylbiphenyl-3-yl)-3,5-dioxocyclohexyl]-acetaldehyde as a white foam.

$^1$H NMR (CDCl$_3$): δ9.84 (m, 1H), 7.49 (m, 3H), 7.38 (m 3H), 7.24 (m 1H), 5.60-5.65 (m, 1H), 2.33-2.90 (m, 5H), 1.88 (m, 1H), 1.71 (m, 1H), 1.27 (s, 3H).

Step 2

Preparation of 2-(4'-Chloro-4-methylbiphenyl-3-yl)-5-[1,3]dioxan-2-ylmethylcyclohexane-1,3-dione

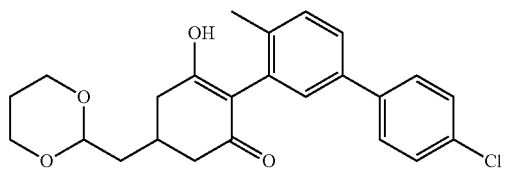 [SMILES: Cc1ccc(-c2ccc(Cl)cc2)cc1C1=C(O)CC(CC2OCCCO2)CC1=O]

To a solution of [4-(4'-chloro-4-methylbiphenyl-3-yl)-3,5-dioxocyclohexyl]-acetaldehyde (0.080 g, 0.23 mmol) and propane-1,3-diol (0.021 g, 0.27 mmol) in anhydrous toluene (4 ml) is added a single crystal of para-toluenesulfonic acid and the mixture is stirred at 80° C. for 45 minutes. After cooling to room temperature the solution is concentrated in vacuo to afford a crude product which is purified by flash column chromatography on silica (ethyl acetate eluant) to afford 2-(4'-chloro-4-methylbiphenyl-3-yl)-5-[1,3]dioxan-2-ylmethylcyclohexane-1,3-dione as a white foam.

Compounds in Table 100 below were prepared by similar methods using appropriate starting materials.

TABLE 100

| Compound Number | Structure | $^1$H NMR (CDCl$_3$ unless stated), or other physical data |
|---|---|---|
| A-1 | 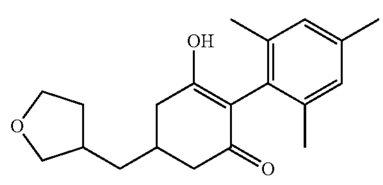 [SMILES: Cc1cc(C)c(C2=C(O)CC(CC3CCOC3)CC2=O)c(C)c1] | δ$_H$ 6.94 (s, 2H), 5.50 (br s, 1H), 3.96 (br t, 1H), 3.89 (m, 1H), 3.78 (q, 1H), 3.36 (t, 1H), 2.71-2.66 (br m, 2H), 2.44-2.22 (m, 7H), 2.09-2.03 (m, 7H), 1.60-1.50 (br m, 3H). |
| A-2 | 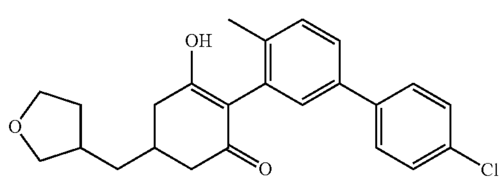 [SMILES: Cc1ccc(-c2ccc(Cl)cc2)cc1C1=C(O)CC(CC2CCOC2)CC1=O] | δ$_H$ 7.50-7.45 (m, 3H), 7.40-7.38 (m, 3H), 7.26-7.24 (m, 1H), 3.97 (br t, 1H), 3.90 (m, 1H), 3.78 (q, 1H), 3.37 (td, 1H), 2.70 (br d, 2H), 2.39-2.26 (m, 4H), 2.18-2.10 (m, 4H), 1.60-1.53 (br m, 3H). |

TABLE 100-continued

| Compound Number | Structure | ¹H NMR (CDCl₃ unless stated), or other physical data |
|---|---|---|
| A-3 | 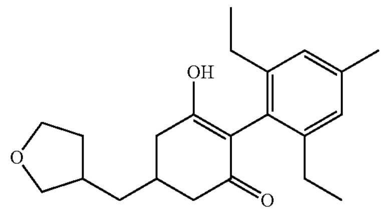 [SMILES: CCc1cc(C)cc(CC)c1C1=C(O)CC(CC2CCOC2)CC1=O] | δ_H 6.98 (2H, s), 3.95 (t, 1H), 3.91-3.86 (br m, 1H), 3.77 (q, 1H), 3.36 (t, 1H), 2.68 (br d, 2H), 2.39-2.29 (m, 11H), 2.15-2.04 (m, 1H), 1.60-1.52 (br m, 3H), 1.07 (q, 6H). |
| A-4 | 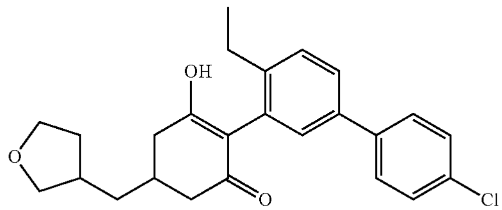 [SMILES: CCc1ccc(-c2ccc(Cl)cc2)cc1C1=C(O)CC(CC2CCOC2)CC1=O] | δ_H 7.53-7.46 (m, 3H), 7.40-7.36 (m, 3H), 7.21 (dd, 1H), 5.14 (br s, 1H), 3.93 (m, 1H), 3.89-3.84 (br m, 1H), 3.75 (q, 1H), 3.34 (m, 1H), 2.67 (br d, 2H), 2.49-2.39 (m, 2H), 2.36-2.23 (br m, 4H), 2.14-2.05 (m, 1H), 1.57-1.49 (m, 3H), 1.16-1.10 (m, 3H). |
| A-5 | 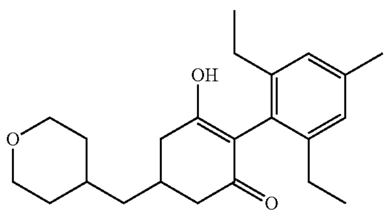 | δ_H 7.0 (s, 2H), 5.50 (br s, 1H), 3.98 (br dd, 2H), 3.40 (br t, 2H), 2.68-2.63 (m, 2H), 2.45-2.25 (m, 10H), 1.69-1.55 (m, 3H), 1.44 (br t, 2H), 1.35-1.20 (m, 2H), 1.08 (q, 6H). |
| A-6 | 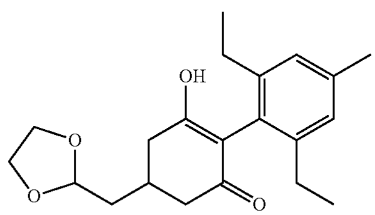 [SMILES: CCc1cc(C)cc(CC)c1C1=C(O)CC(CC2OCCO2)CC1=O] | δ_H 6.98 (br s, 2H), 4.98 (t, 1H), 4.01-3.88 (2 X m, 4H), 2.75 (m, 2H), 2.60-2.25 (m, 10H), 1.85 (m, 2H), 1.05 (m, 6H). |
| A-7 | 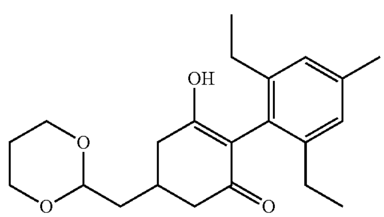 [SMILES: CCc1cc(C)cc(CC)c1C1=C(O)CC(CC2OCCCO2)CC1=O] | δ_H 6.98 (br s, 2H), 5.42 (s, 1H), 4.68 (t, 1H), 4.14 (m, 2H), 3.78 (m, 2H), 2.20-2.75 (m, 9H), 2.32 (s, 3H), 2.10(m, 1H), 1.78 (m, 2H), 1.3 (m, 1H), 1.08 (m, 6H). |
| A-8 | 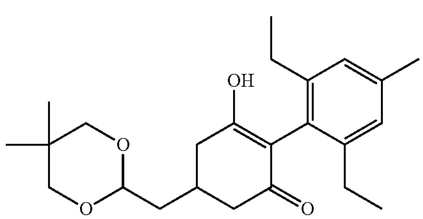 | δ_H 6.98 (br s, 2H), 5.42 (s, 1H), 4.56 (t, 1H), 3.63 (m, 2H), 3.45 (m, 2H), 2.34 (s, 3H), 2.22-2.77 (m, 9H), 1.81 (m, 2H), 1.20 (m, 3H), 1.05 (m, 6H), 0.74 (m, 3H). |
| A-9 | 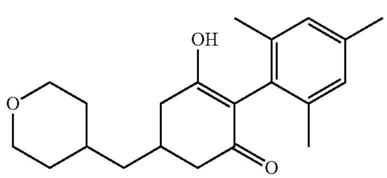 [SMILES: Cc1cc(C)c(C2=C(O)CC(CC3CCOCC3)CC2=O)c(C)c1] | δ_H 6.93 (2H, s), 5.70 (1H, br. s), 3.96 (2H, dd, J = 11.2, 3.6 Hz), 3.42-3.35 (2H, m), 2.65-2.60 (2H, m), 2.39-2.34 (2H, m), 2.28 (3H, s), 2.24-2.17 (1H, m), 2.06 (3H, s), 2.03 (3H, s), 1.69-1.60 (3H, m), 1.33-1.24 (4H, m). |

TABLE 100-continued

| Compound Number | Structure | $^1$H NMR (CDCl$_3$ unless stated), or other physical data |
|---|---|---|
| A-10 | 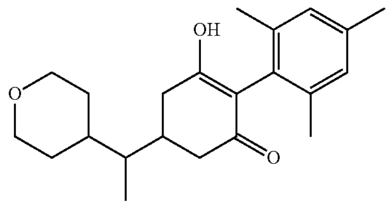 [SMILES: Cc1cc(C)c(C2=C(O)CC(C(C)C3CCOCC3)CC2=O)c(C)c1] | $\delta_H$ 6.92-6.91 (2H, m), 5.97 (1H, br. s), 4.00-3.97 (2H, m), 3.41-3.33 (2H, m), 2.59-2.49 (2H, m), 2.35-2.30 (2H, m), 2.27 (3H, s), 2.06 (3H, s), 2.02 (3H, s), 1.59-1.33 (7H, m), 0.93 (3H, dd). |
| A-11 | 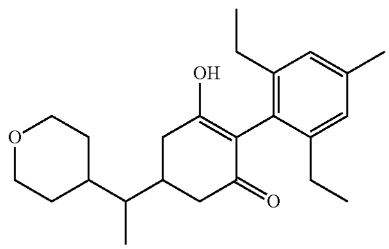 [SMILES: CCc1cc(C)cc(CC)c1C1=C(O)CC(C(C)C2CCOCC2)CC1=O] | $\delta_H$ 7.00 (2H, s), 5.50 (1H, br. s), 3.98 (2H, dd), 3.40 (2H, t, J = 11.3 Hz), 2.68-2.64 (2H, m), 2.39-2.31 (9H, m), 1.67-1.60 (4H, m), 1.45-1.42 (2H, m), 1.34-1.25 (2H, m), 1.08 (6H). |
| A-12 | 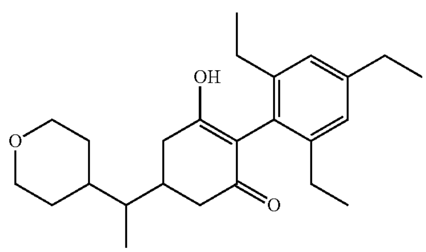 [SMILES: CCc1cc(CC)c(C2=C(O)CC(C(C)C3CCOCC3)CC2=O)c(CC)c1] | $\delta_H$ 7.00 (2H, s), 5.59 (1H, br. s), 4.02-3.99 (2H, m), 3.42-3.35 (2H, m), 2.66-2.53 (4H, m), 2.44-2.28 (6H, m), 1.68-1.50 (4H, m), 1.44-1.37 (3H, m), 1.27-1.23 (3H, m), 1.09 (6H, q), 0.95 (3H, dd). |
| A-13 | 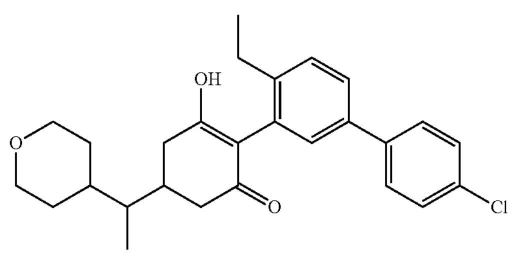 [SMILES: CCc1ccc(-c2ccc(Cl)cc2)cc1C1=C(O)CC(C(C)C2CCOCC2)CC1=O] | $\delta_H$ 7.55-7.52 (1H, m), 7.49-7.47 (2H, m), 7.42 (1H, dd), 7.39-7.36 (2H, m), 7.23 (1H, dd), 4.02-4.00 (2H, m), 3.43-3.35 (2H, m), 2.60-2.24 (6H, m), 1.65-1.37 (5H, m), 1.15 (3H, q), 0.95 (3H, dd). |
| A-14 | 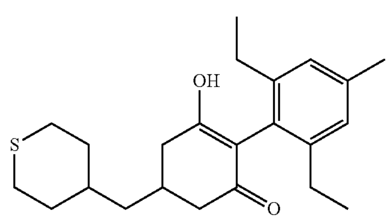 [SMILES: CCc1cc(C)cc(CC)c1C1=C(O)CC(CC2CCSCC2)CC1=O] | $\delta_H$ 6.75 (s, 2H), 2.59 (m, 6H), 2.20 (m, 10H), 1.93 (m, 2H), 1.36 (m, 1H), 1.27 (m, 2H), 1.21 (m, 2H), 0.92 (2t, 6H). |
| A-15 | 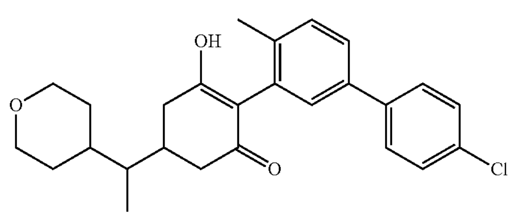 [SMILES: Cc1ccc(-c2ccc(Cl)cc2)cc1C1=C(O)CC(C(C)C2CCOCC2)CC1=O] | $\delta_H$ 7.49-4.47 (2H, m), 7.45-7.42 (1H, m), 7.39-7.36 (2H, m), 7.26-7.18 (2H, m), 4.02-3.99 (2H, m), 3.40-3.35 (2H, m), 2.26-2.53 (2H, m), 2.41-2.34 (2H, m), 2.14 (3H, s), 1.66-1.50 (5H, m), 1.41-1.35 (2H, m), 0.95-0.91 (3H, m). |

TABLE 100-continued

| Compound Number | Structure | ¹H NMR (CDCl₃ unless stated), or other physical data |
|---|---|---|
| A-16 | 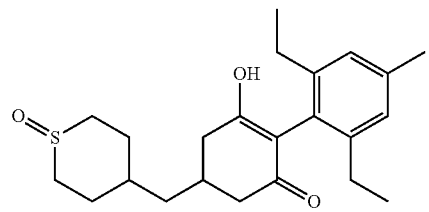 [SMILES: CCc1cc(C)cc(CC)c1C1=C(O)CC(CC2CCS(=O)CC2)CC1=O] | $\delta_H$ 6.99 (s, 2H), 5.64 (br s, 1H), 3.36 (m, 1H), 3.03 (m, 1H), 2.66 (m, 2H), 2.33 (m, 10H), 2.15 (m, 2H), 1.62, (m, 4H), 1.43 (m, 3H), 1.09 (2t, 6H). |
| A-17 | 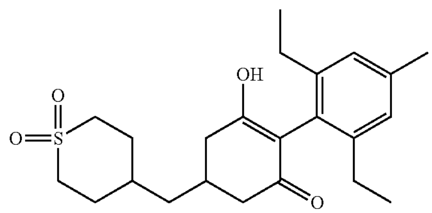 [SMILES: CCc1cc(C)cc(CC)c1C1=C(O)CC(CC2CCS(=O)(=O)CC2)CC1=O] | $\delta_H$ 6.99 (s, 2H), 5.56 (br s, 1H), 3.06 (m, 4H), 2.66 (m, 2H), 2.33 (m, 10H), 2.12 (m, 2H), 1.90 (m, 2H), 1.68 (m, 1H), 1.51 (m, 2H), 1.06 (m, 6H). |
| A-18 | 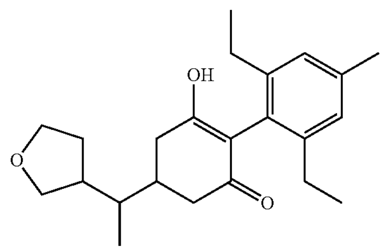 [SMILES: CCc1cc(C)cc(CC)c1C1=C(O)CC(C(C)C2CCOC2)CC1=O] | $\delta_H$ 6.98 (s, 2H), 5.74 (s, 1H), 3.99-3.94 (m, 2H), 3.93-3.87 (m, 1H), 3.80-3.71 (m, 1H), 2.67-2.16 (m, 15H), 1.66-1.53 (m, 2H), 1.10-1.05 (m, 6H), 1.01 (dd, 1H), 0.94 (d, 1H). |
| A-19 | 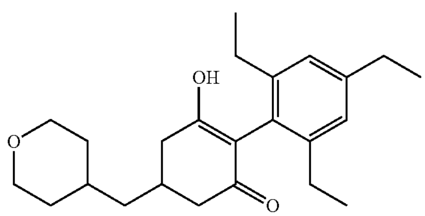 [SMILES: CCc1cc(CC)c(C2=C(O)CC(CC3CCOCC3)CC2=O)c(CC)c1] | $\delta_H$ 7.00 (s, 2H), 5.50 (brs, 1H), 3.98 (dd, 2H), 3.40 (t, 2H), 2.46-2.18 (m, 6H), 2.63 (q, 4H), 1.74-1.50 (m, 6H), 1.45 (t, 1H), 1.40-1.30 (m, 1H), 1.25 (t, 3H), 1.09 (t, 3H), 1.07 (t, 3H). |
| A-20 | 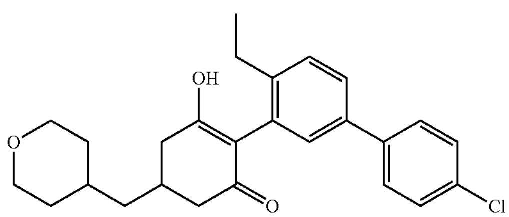 [SMILES: CCc1ccc(-c2ccc(Cl)cc2)cc1C1=C(O)CC(CC2CCOCC2)CC1=O] | $\delta_H$ 7.54 (d, 1H), 7.48 (d, 2H), 7.42 (dd, 1H), 7.38 (d, 2H), 7.23 (dd, 1H), 5.75-5.57 (m, 1H), 3.98 (d, 2H), 3.40 (t, 2H), 2.75-2.59 (m, 2H), 2.47 (q, 2H), 2.54-2.32 (m, 2H), 2.32-2.16 (m, 1H), 1.78-1.51 (m, 4H), 1.51-1.40 (m, 1H), 1.40-1.24 (m, 2H), 1.15 (q, 3H). |
| A-21 | 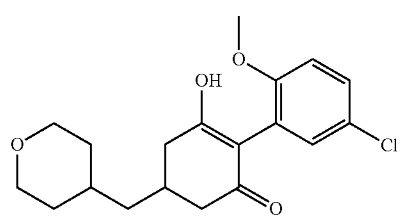 [SMILES: COc1ccc(Cl)cc1C1=C(O)CC(CC2CCOCC2)CC1=O] | $\delta_H$ 7.30 (dd, 1H), 7.12 (s, 1H), 6.91 (d, 1H), 6.21 (brs, 1H), 3.97 (dd, 2H), 3.79 (s, 3H), 3.39 (t, 2H), 2.63 (t, 2H), 2.42-2.26 (m, 2H), 2.26-2.15 (m, 1H), 1.73-1.52 (m, 6H), 1.37-1.27 (m, 1H). |
| A-22 | 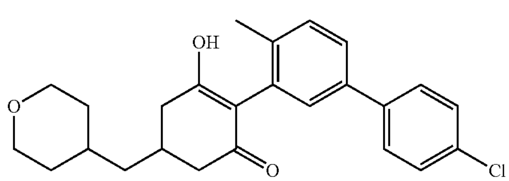 [SMILES: Cc1ccc(-c2ccc(Cl)cc2)cc1C1=C(O)CC(CC2CCOCC2)CC1=O] | $\delta_H$ 7.47 (d, 2H), 7.51-7.43 (m, 1H), (7.36 (d, 2H), 7.40-7.28 (m, 1H), 7.23 (dd, 1H), 6.33 (brs, 1H), 3.94 (dd, 2H), 3.36 (t, 2H), 2.62 (d, 2H), 2.44-2.14 (m, 3H), 2.15 (s, 1.5H), 2.11 (s, 1.5H), 1.70-1.56 (m, 3H), 1.44-1.35 (m, 2H), 1.35-1.21 (m, 2H). |

| Compound Number | Structure | ¹H NMR (CDCl₃ unless stated), or other physical data |
|---|---|---|
| A-23 | 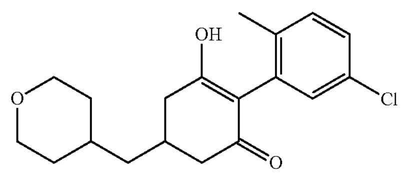 [SMILES: Cc1ccc(Cl)cc1C1=C(O)CC(CC2CCOCC2)CC1=O] | δ_H 7.30-7.20 (m, 2H), 7.06 (s, 1H), 5.62 (s, 0.5H), 5.57 (s, 0.5H), 3.96 (dd, 2H), 3.39 (t, 2H), 2.63 (dt, 2H), 2.44-2.30 (m, 2H), 2.26-2.14 (m, 1H), 2.10 (s, 1.5H), 2.07 (s, 1.5H), 1.72-1.49 (m, 3H), 1.41 (t, 2H), 1.37-1.24 (m, 2H). |
| A-24 | 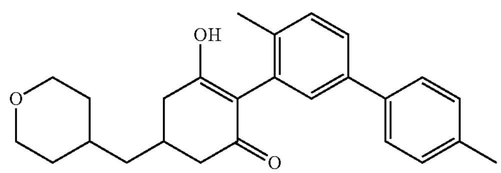 [SMILES: Cc1ccc(-c2ccc(C)c(C3=C(O)CC(CC4CCOCC4)CC3=O)c2)cc1] | δ_H 7.49 (dt, 1H), 7.45 (d, 2H), 7.34 (dd, 1H), 7.23-7.27 (m, 1H), 7.21 (d, 2H), 6.07 (brs, 1H), 3.95 (dd, 2H), 3.37 (t, 2H), 2.57-2.68 (m, 2H), 2.38 (s, 3H), 2.29-2.42 (m, 2H), 2.15-2.27 (m, 1H), 1.56-1.71 (m, 3H), 2.11 (s, 1.5H), 2.15 (s, 1.5H), 1.36-1.44 (m, 2H), 1.21-1.36 (m, 2H). |
| A-25 | 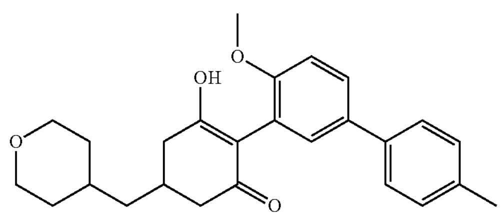 [SMILES: COc1ccc(-c2ccc(C)cc2)cc1C1=C(O)CC(CC2CCOCC2)CC1=O] | δ_H 7.55 (dd, 1H), 7.43 (d, 2H), 7.33 (d, 1H), 7.21 (d, 2H), 7.03 (d, 1H), 3.96 (dd, 2H), 3.82 (s, 3H), 3.38 (t, 2H), 2.70-2.58 (m, 2H), 2.42-2.32 (m, 2H), 2.37 (s, 3H), 2.43-2.32 (m, 1H), 1.71-1.57 (m, 3H), 1.40 (t, 2H), 1.36-1.23 (m, 2H). |
| A-26 | 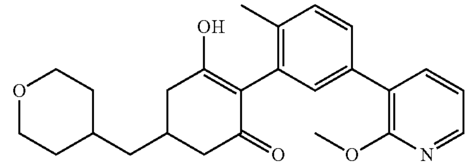 [SMILES: COc1ncccc1-c1ccc(C)c(C2=C(O)CC(CC3CCOCC3)CC2=O)c1] | δ_H 8.13 (dd, 1H), 7.60 (dt, 1H), 7.49 (dt, 1H), 7.39 (dd, 1H), 7.06 (t, 1H), 6.95 (td, 1H), 4.02-3.92 (m, 2H), 3.95 (s, 3H), 3.39 (t, 2H), 2.72-2.56 (m, 2H), 2.46-2.31 (m, 2H), 2.29-2.19 (m, 1H), 2.17 (d, 3H), 1.73-1.58 (m, 3H), 1.47-1.38 (m, 2H), 1.38-1.24 (m, 2H). |
| A-27 | 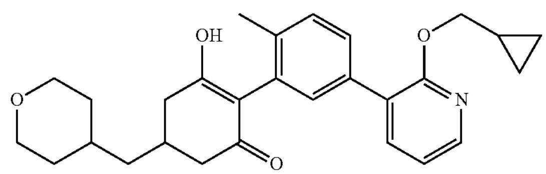 [SMILES: Cc1ccc(-c2cccnc2OCC2CC2)cc1C1=C(O)CC(CC2CCOCC2)CC1=O] | δ_H 8.09 (dd, 1H), 7.61 (d, 1H), 7.56-7.45 (m, 1H), 7.41-7.34 (m, 1H), 7.07 (t, 1H), 6.93 (td, 1H), 4.25-4.10 (m, 2H), 3.98 (dd, 2H), 3.39 (t, 2H), 2.72-2.57 (m, 2H), 2.46-2.32 (m, 2H), 2.29-2.19 (m, 1H), 2.17 (d, 3H), 1.85-1.52 (m, 6H), 1.48-1.38 (m, 4H), 1.38-1.19 (m, 2H). |
| A-28 | 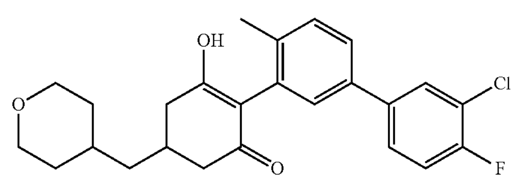 [SMILES: Cc1ccc(-c2ccc(F)c(Cl)c2)cc1C1=C(O)CC(CC2CCOCC2)CC1=O] | δ_H 7.57 (d, 1H), 7.49-7.36 (m, 1H), 7.24-7.14 (m, 1H), 7.02 (t, 1H), 6.84 (dd, 1H), 6.78 (td, 1H), 5.65 (s, 0.5H, CH), 5.60 (s, 0.5H, CH), 3.99 (dd, 2H), 3.41 (t, 2H), 2.74-2.61 (m, 2H), 2.47-2.33 (m, 2H), 2.30-2.20 (m, 1H), 2.17 (d, 3.0H), 1.73-1.24 (m, 7H). |
| A-29 | 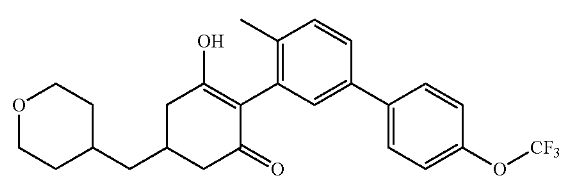 [SMILES: Cc1ccc(-c2ccc(OC(F)(F)F)cc2)cc1C1=C(O)CC(CC2CCOCC2)CC1=O] | δ_H 7.56 (d, 2H), 7.49 (td, 1H), 7.39 (d, 1H), 7.26-7.22 (m, 3H), 5.73 (brs, 0.5H), 5.67 (brs, 0.5H), 3.98 (dd, 2H), 3.40 (t, 2H), 2.73-2.59 (m, 2H), 2.47-2.33 (m, 2H), 2.29-2.20 (m, 1H), 2.17 (d, 3H,), 1.64 (d, 3H), 1.43 (t, 2H), 1.39-1.24 (m, 2H). |
| A-30 | 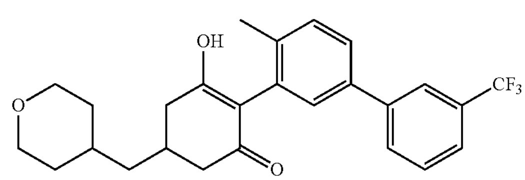 [SMILES: Cc1ccc(-c2cccc(C(F)(F)F)c2)cc1C1=C(O)CC(CC2CCOCC2)CC1=O] | δ_H 7.79 (s, 1H), 7.73 (d, 1H), 7.61-7.50 (m, 3H), 7.41 (d, 1H), 7.30 (t, 1H), 5.68 (brs, 0.5H), 5.63 (brs, 0.5H), 3.98 (dd, 2H), 3.40 (t, 2H), 2.74-2.57 (m, 2H), 2.48-2.32 (m, 2H), 2.30-2.20 (m, 1H), 2.18 (d, 3H), 1.65 (d, 3H), 1.44 (t, 2H), 1.39-1.23 (m, 2H). |

TABLE 100-continued

| Compound Number | Structure | $^1$H NMR (CDCl$_3$ unless stated), or other physical data |
|---|---|---|
| A-31 | 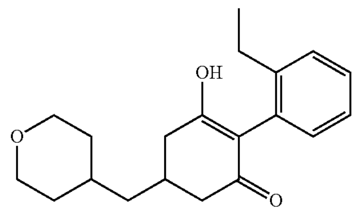 [SMILES: CCc1ccccc1C1=C(O)CC(CC2CCOCC2)CC1=O] | $\delta_H$ 7.34 (s, 2H), 7.29-7.23 (m, 1H), 7.05-7.01 (m, 1H), 5.63 (brs, 0.5H), 5.57 (brs, 0.5H), 3.97 (dd, 2H), 3.40 (td, 2H), 2.71-2.58 (m, 2H), 2.51-2.31 (m, 4H), 2.28-2.15 (m, 1H), 1.73-1.58 (m, 3H), 1.46-1.39 (m, 2H), 1.38-1.26 (m, 2H), 1.11 (q, 3H). |
| A-32 | 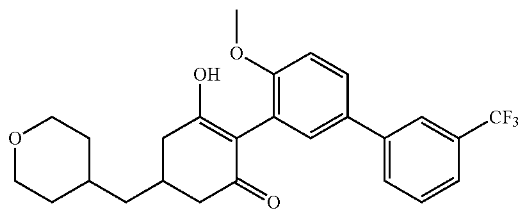 [SMILES: COc1ccc(-c2cccc(C(F)(F)F)c2)cc1C1=C(O)CC(CC2CCOCC2)CC1=O] | $\delta_H$ 7.77 (s, 1H), 7.71 (d, 1H), 7.60-7.45 (m, 3H), 7.36 (d, 1H), 6.97 (d, 1H), 5.95 (brs, 1H), 3.98-3.90 (m, 2H), 3.85 (s, 3H), 3.35 (td, 2H), 2.62-2.55 (m, 2H), 2.55-2.45 (m, 1H), 2.36 (d, 2H), 1.70-1.39 (m, 3H), 1.33-1.19 (m, 4H). |
| A-33 | 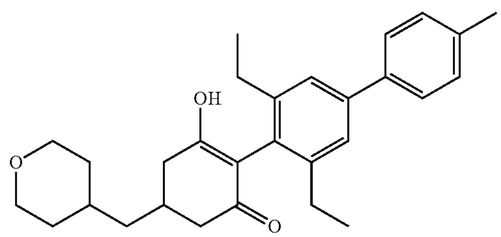 [SMILES: CCc1cc(-c2ccc(C)cc2)cc(CC)c1C1=C(O)CC(CC2CCOCC2)CC1=O] | $\delta_H$ 7.49 (d, 2H), 7.35 (s, 2H), 7.26 (d, 2H), 5.58 (s, 1H), 3.98 (m, dd, 2H), 3.4 (m, 2H), 2.68 (m, 2H), 2.45 (m, 9H), 2.27 (m, 1H), 1.65 (m, 3H), 1.43 (t, 2H), 1.3 (m, 2H), 1.12 (m, 6H). |
| A-34 | 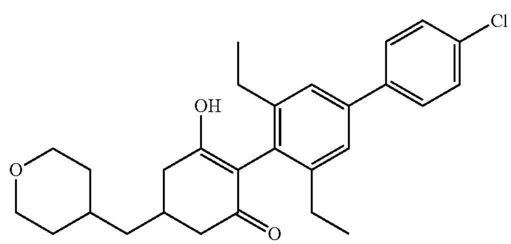 [SMILES: CCc1cc(-c2ccc(Cl)cc2)cc(CC)c1C1=C(O)CC(CC2CCOCC2)CC1=O] | $\delta_H$ 7.52 (dd, 2H), 7.4 (dd, 2H), 7.33 (s, 2H), 5.52 (s, 1H), 3.98 (m, 2H), 3.4 (m, 2H), 2.69 (m, 2H), 2.45 (m, 6H), 2.27 (m, 1H), 1.65 (m, 3H), 1.45 (t, 2H), 1.33 (m, 2H), 1.13 (m, 6H). |
| A-35 | 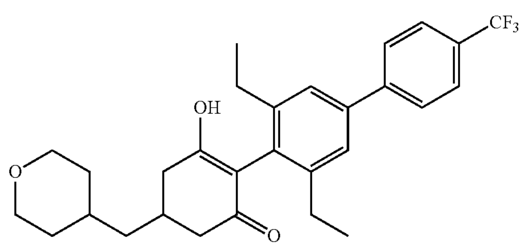 [SMILES: CCc1cc(-c2ccc(C(F)(F)F)cc2)cc(CC)c1C1=C(O)CC(CC2CCOCC2)CC1=O] | $\delta_H$ 7.69 (dd, 4H), 7.38 (s, 2H), 5.52 (s, 1H), 3.98 (m, 2H), 3.41 (m, 2H), 2.7 (m, 2H), 2.45 (m, 6H), 2.28 (m,1H), 1.65 (m, 3H), 1.46 (m, 2H), 1.33 (m, 2H), 1.15 (m, 6H). |
| A-36 | 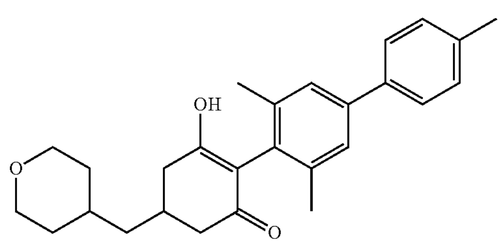 [SMILES: Cc1ccc(-c2cc(C)c(C3=C(O)CC(CC4CCOCC4)CC3=O)c(C)c2)cc1] | $\delta_H$ 7.5 (dd, 2H), 7.36 (s, 2H), 7.28 (d, 2H), 5.62 (s, 1H), 4.03 (m, 2H), 3.42 (m, 2H), 2.72 (m, 2H), 2.45 (m, 2H), 2.43 (s, 3H), 2.3 (m, 1H), 2.22 (s, 3H), 2.19 (s, 3H), 1.69 (m, 3H), 1.49 (m, 2H), 1.37 (m, 2H). |

TABLE 100-continued

| Compound Number | Structure | ¹H NMR (CDCl₃ unless stated), or other physical data |
|---|---|---|
| A-37 | 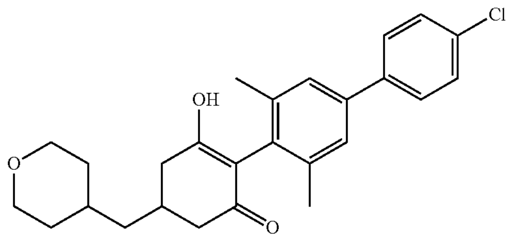 [SMILES: Cc1cc(-c2ccc(Cl)cc2)cc(C)c1C1=C(O)CC(CC2CCOCC2)CC1=O] | δ$_H$ 7.54 (d, 2H), 7.44 (d, 2H) 7.32 (s, 2H), 5.6 (s, 1H), 4.02 (m, 2H), 3.43 (m, 2H), 2.72 (m, 2H), 2.45 (m, 2H), 2.3 (m, 1H), 2.22 (s, 3H), 2.19 (s, 3H), 1.69 (m, 3H), 1.5 (m, 2H), 1.37 (m, 2H). |
| A-38 | 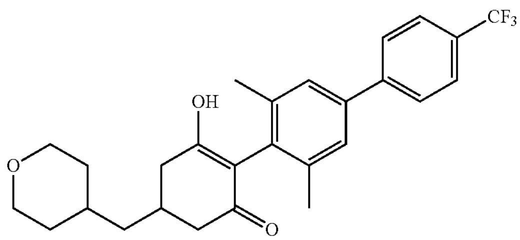 [SMILES: Cc1cc(-c2ccc(C(F)(F)F)cc2)cc(C)c1C1=C(O)CC(CC2CCOCC2)CC1=O] | δ$_H$ 7.67 (dd, 4H), 7.33 (s, 2H), 5.5 (s, 1H), 3.98 (m, 2H), 3.4 (m, 2H), 2.68 (m, 2H), 2.42 (m, 2H), 2.25 (m, 1H), 2.17 (s, 3H), 2.15 (s, 3H), 1.65 (m, 3H), 1.45 (m, 2H), 1.33 (m, 2H). |
| A-39 | 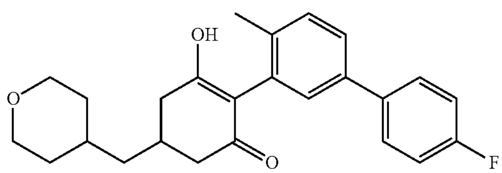 [SMILES: Cc1ccc(-c2ccc(F)cc2)cc1C1=C(O)CC(CC2CCOCC2)CC1=O] | δ$_H$ 7.49 (q, 2H), 7.44 (d, 1H), 7.32 (d, 1H), 7.17 (d, 1H), 7.08 (t, 2H), 6.36 (brs, 1H), 3.93 (dd, 2H), 3.35 (t, 2H), 2.61 (d, 2H), 2.41-2.27 (m, 2H), 2.24-2.15 (m, 1H), 2.13 (d, 3H), 1.69-1.55 (m, 3H), 1.42-1.35 (m, 2H), 1.35-1.20 (m, 2H). |
| A-40 | 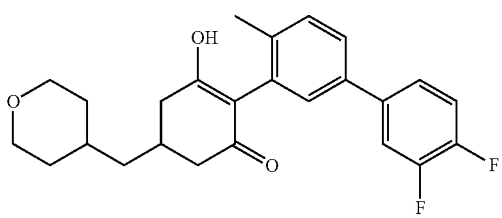 [SMILES: Cc1ccc(-c2ccc(F)c(F)c2)cc1C1=C(O)CC(CC2CCOCC2)CC1=O] | δ$_H$ 7.42 (d, 1H), 7.34 (d, 2H), 7.29-7.22 (m, 1H), 7.22-7.12 (m, 2H), 6.15 (brd, 1H), 3.94 (dd, 2H), 3.37 (t, 2H), 2.63 (td, 2H), 2.42-2.30 (m, 2H), 2.26-2.15 (m, 1H), 2.14 (d, 3H), 1.72-1.57 (m, 3H), 1.44-1.37 (m, 2H), 1.37-1.22 (m, 2H). |
| A-41 | 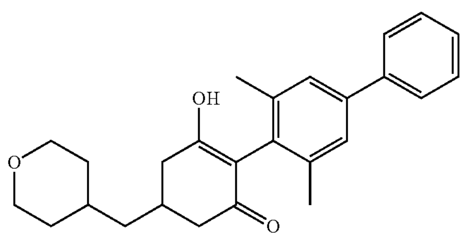 [SMILES: Cc1cc(-c2ccccc2)cc(C)c1C1=C(O)CC(CC2CCOCC2)CC1=O] | δ$_H$ 7.57 (d, 2H), 7.53 (t, 2H), 7.36-7.32 (m, 3H), 5.74 (s, 1H), 3.96 (dd, 2H), 3.39 (ddt, 2H), 2.70-2.65 (m, 2H), 2.45-2.20 (m, 3H), 2.17 (s, 3H), 2.14 (s, 3H), 1.75-1.50 (m, 3H), 1.45-1.20 (m, 4H). |
| A-42 | 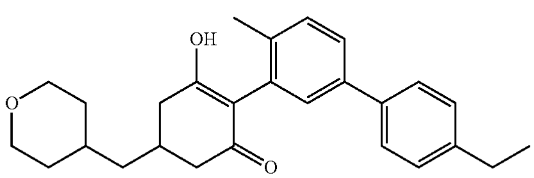 [SMILES: CCc1ccc(-c2ccc(C)c(C3=C(O)CC(CC4CCOCC4)CC3=O)c2)cc1] | δ$_H$ 7.52 (dt, 1H), 7.48 (d, 2H), 7.36 (dd, 1H), 7.30-7.22 (m, 3H), 5.77 (brs, 0.5H), 5.71 (brs, 0.5H), 3.98 (dd, 2H), 3.40 (t, 2H), 2.68 (q, 2H), 2.73-2.60 (m, 2H), 2.45-2.34 (m, 2H), 2.29-2.19 (m, 1H), 2.17 (s, 1.5H), 2.13 (s, 1.5H), 1.74-1.56 (m, 3H), 1.43 (t, 2H), 1.39-1.23 (m, 2H), 1.26 (t, 3H). |
| A-43 | 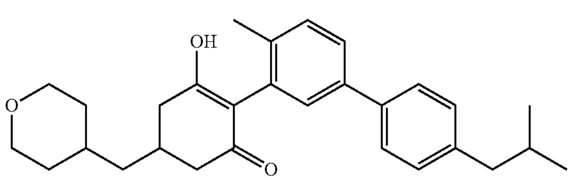 [SMILES: Cc1ccc(-c2ccc(CC(C)C)cc2)cc1C1=C(O)CC(CC2CCOCC2)CC1=O] | δ$_H$ 7.52 (td, 1H), 7.46 (d, 2H), 7.36 (dd, 1H), 7.28 (d, 1H), 7.18 (d, 2H), 5.79 (brs, 0.5H), 5.73 (brs, 0.5H), 3.98 (dd, 2H), 3.40 (t, 2H), 2.72-2.60 (m, 2H), 2.50 (d, 2H), 2.45-2.34 (m, 2H), 2.30-2.20 (m, 1H), 2.16 (s, 1.5H), 2.14 (s, 1.5H), 1.88 (quintet, 1H), 1.78-1.59 (m, 3H), 1.43 (t, 2H), 1.39-1.26 (m, 2H), 0.92 (d, 6H). |

| Compound Number | Structure | ¹H NMR (CDCl₃ unless stated), or other physical data |
|---|---|---|
| A-44 | 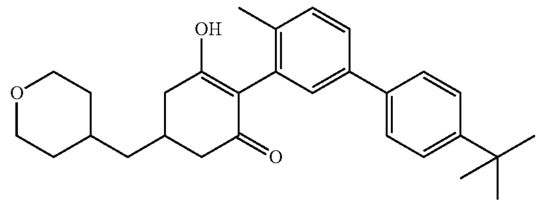 [SMILES: Cc1ccc(-c2ccc(C(C)(C)C)cc2)cc1C1=C(O)CC(CC2CCOCC2)CC1=O] | δ$_H$ 7.53 (t, 1H), 7.49 (d, 2H), 7.43 (d, 2H), 7.37 (dd, 1H), 7.30-7.27 (m, 1H), 5.75 (s, 0.5H), 5.69 (s, 0.5H), 3.98 (dd, 2H), 3.40 (t, 2H), 2.71-2.60 (m, 2H), 2.44-2.34 (m, 2H), 2.29-2.20 (m, 1H), 2.17 (s, 1.5H), 2.15 (s, 1.5H), 1.69-1.56 (m, 3H), 1.43 (t, 2H), 1.35 (s, 9H), 1.38-1.27 (m, 2H). |
| A-45 | 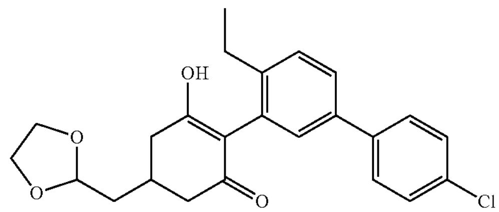 [SMILES: CCc1ccc(-c2ccc(Cl)cc2)cc1C1=C(O)CC(CC2OCCO2)CC1=O] | δ$_H$ 7.33 (m, 1H), 7.33-7.55 (m, 6H), 5.63 (m, 1H), 4.99 (m, 1H), 4.02 (m, 2H), 3.90 (m, 2H), 2.27-2.84 (m, 7H), 1.85 (m, 2H), 1.15 (m, 3H). |
| A-46 | 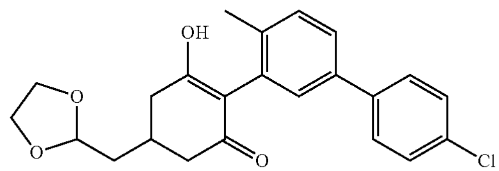 [SMILES: Cc1ccc(-c2ccc(Cl)cc2)cc1C1=C(O)CC(CC2OCCO2)CC1=O] | δ$_H$ 7.48 (m, 3H), 7.38 (m, 3H), 7.25 (m, 1H), 5.63-5.69 (m, 1H), 4.98 (m, 1H), 4.01 (m, 2H), 3.88 (m, 2H), 2.23-2.85 (m, 5H), 2.13-2.18 (m, 3H), 1.85 (m, 2H). |
| A-47 | 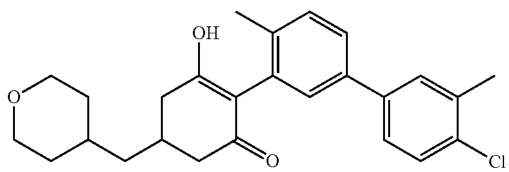 [SMILES: Cc1cc(-c2ccc(C)c(C3=C(O)CC(CC4CCOCC4)CC3=O)c2)ccc1Cl] | δ$_H$ 7.49 (dt, 1H), 7.42-7.39 (m, 1H), 7.37 (d, 2H), 7.30 (dd, 1H), 7.25-7.22 (m, 1H), 5.80-5.16 (brs, 1H), 4.03 (dd, 2H), 3.44 (t, 2H), 2.70 (d, 2H), 2.42 (s, 3H,), 2.47-2.31 (m, 3H), 2.16 (s, 1.5H), 2.13 (s, 1.5H), 1.71-1.61 (m, 3H), 1.49-1.41 (m, 2H), 1.40-1.28 (m, 2H). |
| A-48 | 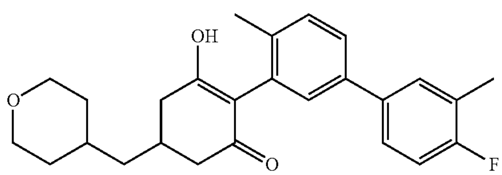 [SMILES: Cc1cc(-c2ccc(C)c(C3=C(O)CC(CC4CCOCC4)CC3=O)c2)ccc1F] | δ$_H$ 7.50-7.44 (m, 1H), 7.39-7.29 (m, 3H), 7.24-7.21 (m, 1H), 7.06-7.00 (m, 1H), 5.86-5.59 (m, 1H), 4.03-3.96 (m, 2H), 3.41 (t, 2H), 2.72-2.61 (m, 2H), 2.45-2.36 (m, 2H), 2.32 (s, 3H), 2.30-2.21 (m, 1H), 2.17 (s, 1.5H), 2.13 (s, 1.5H), 1.70-1.60 (m, 3H), 1.47-1.40 (m, 2H), 1.39-1.29 (m, 2H). |
| A-49 | 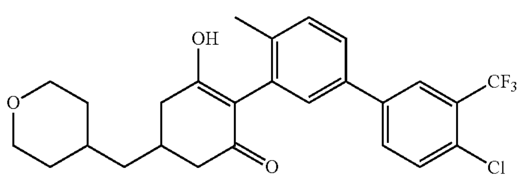 [SMILES: Cc1ccc(-c2ccc(Cl)c(C(F)(F)F)c2)cc1C1=C(O)CC(CC2CCOCC2)CC1=O] | δ$_H$ 7.67-7.22 (m, 6H), 6.02-5.57 (s, 1H), 4.07-3.98 (m, 2H), 3.44 (t, 2H), 2.70 (d, 2H), 2.49-2.20 (m, 3H), 2.19 (s, 1.5H), 2.16 (s, 1.5H), 1.75-1.60 (m, 3H), 1.49-1.41 (m, 2H), 1.41-1.27 (m, 2H). |
| A-50 | 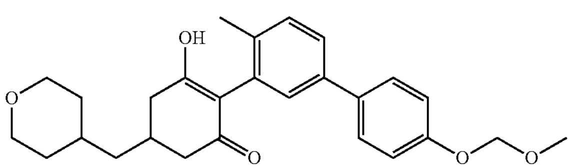 [SMILES: COCOc1ccc(-c2ccc(C)c(C3=C(O)CC(CC4CCOCC4)CC3=O)c2)cc1] | δ$_H$ 7.51-7.45 (m, 3H), 7.38-7.33 (m, 1H), 7.25-7.21 (m, 1H), 7.08 (dd, 2H), 5.83-5.64 (m, 1H), 5.21 (s, 2H), 3.99 (dd, 2H), 3.50 (s, 3H), 3.41 (t, 2H), 2.72-2.61 (m, 2H), 2.45-2.34 (m, 2H), 2.29-2.19 (m, 1H), 2.16 (s, 1.5H), 2.13 (s, 1.5H), 1.70-1.60 (m, 3H), 1.46-1.40 (m, 2H), 1.38-1.29 (m, 2H). |
| A-51 | 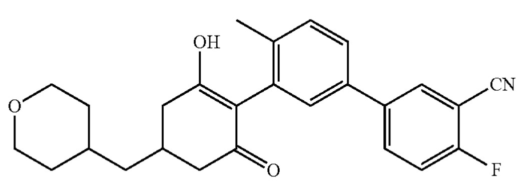 [SMILES: Cc1ccc(-c2ccc(F)c(C#N)c2)cc1C1=C(O)CC(CC2CCOCC2)CC1=O] | δ$_H$ 7.82-7.73 (m, 2H), 7.48-7.37 (m, 2H), 7.31-7.18 (m, 2H), 5.70-5.25 (s, 1H), 4.07-3.96 (m, 2H), 3.43 (t, 2H), 2.76-2.62 (m, 2H), 2.49-2.25 (m, 3H), 2.17 (s, 1.5H), 2.15 (s, 1.5H), 1.75-1.59 (m, 3H), 1.50-1.40 (m, 2H), 1.39-1.29 (m, 2H). |

TABLE 100-continued

| Compound Number | Structure | ¹H NMR (CDCl₃ unless stated), or other physical data |
|---|---|---|
| A-52 | 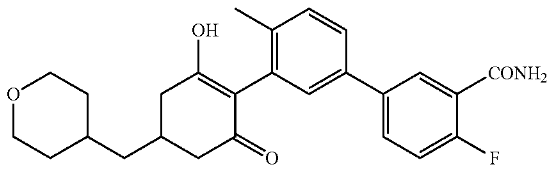 [SMILES: Cc1ccc(-c2ccc(F)c(C(N)=O)c2)cc1C1=C(O)CC(CC2CCOCC2)CC1=O] | δ$_H$ 8.30-8.21 (m, 1H), 7.74-7.65 (m, 1H), 7.35 (d, 1H), 7.48 (dt, 1H), 7.31-7.27 (m, 1H), 7.20-7.15 (m, 1H), 6.87 (brd, 1H), 6.73 (brs, 1H), 5.66-5.04 (brs, 1H), 3.97 (dt, 2H), 3.39 (t, 2H), 2.67 (dd, 2H), 2.49-2.24 (m, 3H), 2.17 (s, 1.5H), 2.14 (s, 1.5H), 1.74-1.59 (m, 3H), 1.50-1.42 (t, 2H), 1.38-1.28 (m, 2H). |
| A-53 | 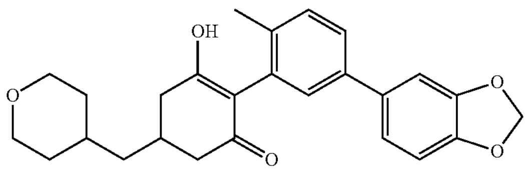 [SMILES: Cc1ccc(-c2ccc3c(c2)OCO3)cc1C1=C(O)CC(CC2CCOCC2)CC1=O] | δ$_H$ 7.44 (d, 1H), 7.34 (d, 1H), 7.22-7.08 (m, 2H), 7.04-6.98 (m, 1H), 6.85 (d, 1H), 5.99 (s, 2H), 5.06-4.60 (brs, 1H), 4.05-3.91 (m, 2H), 3.47-3.30 (m, 2H), 2.72-2.53 (m, 2H), 2.52-2.26 (m, 3H), 2.19 (s, 3H), 1.73-1.50 (m, 3H), 1.50-1.39 (m, 2H), 1.32-1.18 (m, 2H). |
| A-54 | 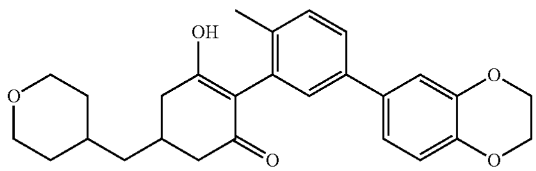 [SMILES: Cc1ccc(-c2ccc3c(c2)OCCO3)cc1C1=C(O)CC(CC2CCOCC2)CC1=O] | δ$_H$ 7.26-7.19 (m, 2H), 7.09-7.01 (m, 2H), 6.90-6.80 (m, 3H), 4.27 (d, 4H), 3.98 (dd, 2H), 3.40 (t, 2H), 2.70-2.58 (m, 2H), 2.42-2.17 (m, 3H), 2.09 (s, 1.5H), 2.05 (s, 1.5H), 1.72-1.57 (m, 3H), 1.46-1.38 (m, 2H), 1.37-1.23 (m, 2H). |
| A-55 | 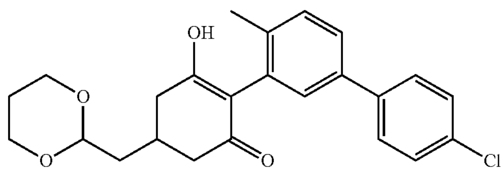 [SMILES: Cc1ccc(-c2ccc(Cl)cc2)cc1C1=C(O)CC(CC2OCCCO2)CC1=O] | δ$_H$ 7.50 (m, 3H), 7.39 (m, 3H), 7.25 (m, 1H) 5.70 (br, 1H), 4.68 (m, 1H), 4.13 (m, 2H), 3.80 (m, 2H), 2.20-2.80 (m, 5H), 2.13-2.16 (m, 3H), 2.10 (m, 1H), 1.77 (m, 2H), 1.36 (m, 1H). |
| A-56 | 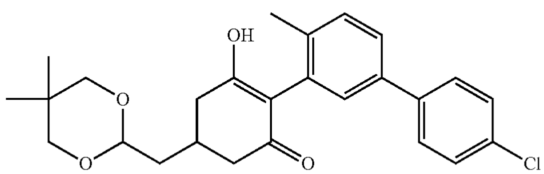 [SMILES: Cc1ccc(-c2ccc(Cl)cc2)cc1C1=C(O)CC(CC2OCC(C)(C)CO2)CC1=O] | δ$_H$ 7.48 (m, 3H), 7.37 (m, 3H), 7.24 (m, 1H), 5.62 (br, 1H), 4.58 (m, 1H), 3.60 (m, 2H), 3.44 (m, 2H), 2.20-2.81 (m, 5H), 2.13-2.18 (m, 3H), 1.82 (m, 2H), 1.21 (s, 3H), 0.75 (s, 3H). |
| A-57 | 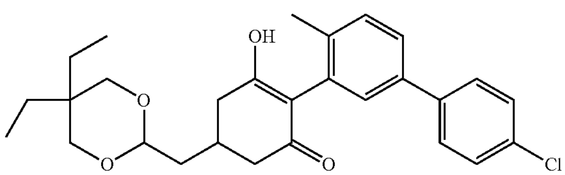 [SMILES: CCC1(CC)COC(CC2CC(=O)C(c3cc(-c4ccc(Cl)cc4)ccc3C)=C(O)C2)OC1] | δ$_H$ 7.48 (m, 3H), 7.38 (m, 3H), 7.23 (m, 1H), 5.62 (br, 1H), 4.55 (m, 1H), 2.82 (m, 2H), 2.40 (m, 2H), 2.20-2.80 (m, 5H), 2.14-2.19 (m, 3H), 1.80 (m, 2H), 1.73 (m, 2H), 1.10 (m, 2H), 0.88 (m, 3H), 0.80 (m, 3H). |
| A-58 | 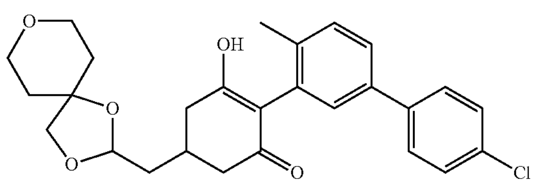 [SMILES: Cc1ccc(-c2ccc(Cl)cc2)cc1C1=C(O)CC(CC2OCC3(CCOCC3)O2)CC1=O] | δ$_H$ 7.48 (m, 3H), 7.39 (m, 3H), 7.24 (m, 1H), 5.72 (br, 1H), 5.14 (m, 1H), 3.60-3.90 (m, 6H), 2.23-2.85 (m, 5H), 2.16-2.20 (m, 3H), 1.87 (m, 2H), 1.73 (m, 4H), 1.10 (m, 2H). |
| A-59 | 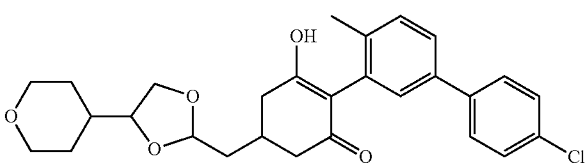 [SMILES: Cc1ccc(-c2ccc(Cl)cc2)cc1C1=C(O)CC(CC2OCC(C3CCOCC3)O2)CC1=O] | δ$_H$ 7.49 (m, 3H), 7.37 (m, 3H), 7.25 (m, 1H), 5.68 (br, 1H), 5.02-5.09 (m, 1H), 3.40-4.00 (m, 7H) 2.22-2.84 (m, 5H), 2.13-2.19 (m, 3H), 1.42-1.90 (m, 7H). |

TABLE 100-continued

| Compound Number | Structure | $^1$H NMR (CDCl$_3$ unless stated), or other physical data |
|---|---|---|
| A-60 | 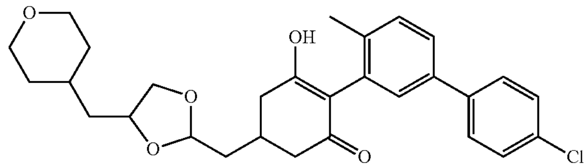 [SMILES: Cc1ccc(-c2ccc(Cl)cc2)cc1C1=C(O)CC(CC2OCC(CC3CCOCC3)O2)CC1=O] | $\delta_H$ 7.48 (m, 3H), 7.35 (m, 3H), 7.22 (m, 1H), 5.70 (br, 1H), 5.01-5.14 (m, 1H), 3.35-4.18 (m, 7H), 2.20-2.85 (m, 5H), 2.13-2.18 (m, 3H), 1.25-1.90 (m, 9H). |
| A-61 | 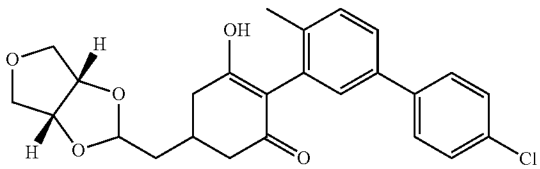 [SMILES: Cc1ccc(-c2ccc(Cl)cc2)cc1C1=C(O)CC(CC2O[C@H]3COC[C@H]3O2)CC1=O] | $\delta_H$ 7.48 (m, 3H), 7.36 (m, 3H), 7.23 (m, 1H), 5.72 (br, 1H), 5.00 (m, 1H), 3.42-4.10 (m, 6H), 2.23-2.88 (m, 5H), 2.14-2.19 (m, 3H), 1.90 (m, 2H). |
| A-62 | 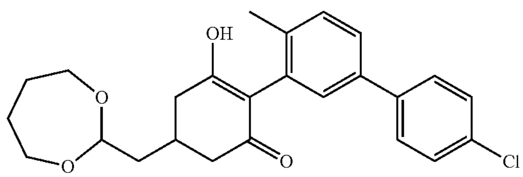 [SMILES: Cc1ccc(-c2ccc(Cl)cc2)cc1C1=C(O)CC(CC2OCCCCO2)CC1=O] | $\delta_H$ 7.46 (m, 3H), 7.35 (m, 3H), 7.23 (m, 1H), 5.70 (br, 1H), 4.84 (m, 1H), 3.91 (m, 2H), 3.65 (m, 2H), 2.20-2.80 (m, 5H), 2.15-2.19 (m, 3H), 1.73 (m, 6H). |
| A-63 | 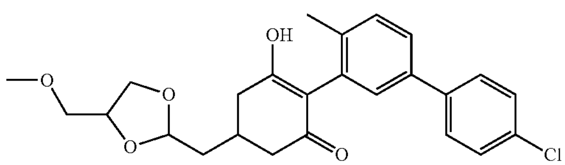 [SMILES: COCC1COC(CC2CC(=O)C(c3cc(-c4ccc(Cl)cc4)ccc3C)=C(O)C2)O1] | $\delta_H$ 7.48 (m, 3H), 7.38 (m, 3H), 7.24 (m, 1H), 5.75 (br, 1H), 5.02-5.12 (m, 1H), 3.42 (s, 3H), 3.42-4.35 (m, 5H), 2.24-2.83 (m, 5H), 2.14-2.19 (m, 3H), 1.86 (m, 2H). |
| A-64 | 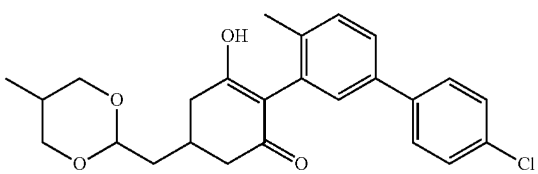 [SMILES: Cc1ccc(-c2ccc(Cl)cc2)cc1C1=C(O)CC(CC2OCC(C)CO2)CC1=O] | $\delta_H$ 7.48 (m, 3H), 7.36 (m, 3H), 7.23 (m, 1H), 5.74 (br, 1H), 4.09-4.66 (m, 1H), 3.25-4.06 (m, 4H), 2.20-2.80 (m, 5H), 2.13-2.18 (m, 3H), 2.10 (m, 1H), 1.79 (m, 2H). 1.30-0.72 (2xd, 3H). |
| A-65 | 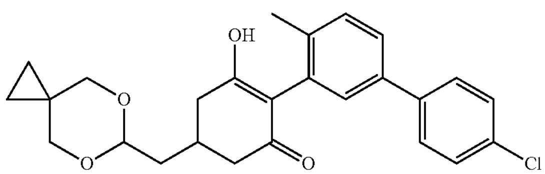 [SMILES: Cc1ccc(-c2ccc(Cl)cc2)cc1C1=C(O)CC(CC2OCC3(CC3)CO2)CC1=O] | $\delta_H$ 7.47 (m, 3H), 7.36 (m, 3H), 7.23 (m, 1H), 5.73 (br, 1H), 4.74 (m, 1H), 4.12 (m, 2H), 3.25 (m, 2H), 2.21-2.80 (m, 5H), 2.13-2.19 (m, 3H), 1.85 (m, 2H), 0.71 (m, 2H), 0.35 (m, 2H). |

Example 6

Preparation of 2,2-dimethylpropionic acid 3-oxo-5-(tetrahydrofuran-3-ylmethyl)-2-(2,4,6-trimethylphenyl)cyclohex-1-enyl Ester

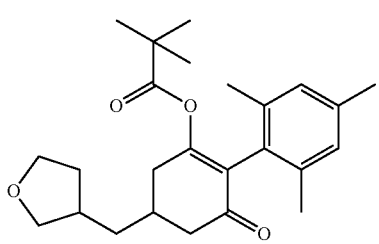 [SMILES: Cc1cc(C)c(C2=C(OC(=O)C(C)(C)C)CC(CC3CCOC3)CC2=O)c(C)c1]

A solution of trimethylacetyl chloride (55 mg, 0.457 mmol) in dichloromethane (2 ml) is added dropwise to a solution of 2-(2,4,6-trimethylphenyl)-5-(tetrahydrofuran-3-ylmethyl)-cyclohexane-1,3-dione (120 mg, 0.38 mmol) in dichloromethane (2 ml) and the mixture is cooled in an ice bath and stirred at 0° C. for 2 minutes. A solution of triethylamine (46 mgs, 0.457 mmol) in dichloromethane (1 ml) is added, and once the addition is complete the cooling bath is removed and the reaction mixture is stirred at room temperature for 2 hours. The mixture is diluted with dichloromethane (20 ml) and washed with saturated aqueous sodium bicarbonate solution (3×20 ml). The organic phase is dried over anhydrous magnesium sulfate, filtered and the filtrate is concentrated in vacuo. The residue is purified by column chromatography on silica gel to give 2,2-dimethylpropionic acid 3-oxo-5-(tetrahydrofuran-3-ylmethyl)-2-(2,4,6-trimethylphenyl)cyclohex-1-enyl ester as a white solid, m.p. 108-110° C.

$^1$H NMR (CDCl$_3$, ppm) 66.81 (s, 2H), 3.94 (q, 1H), 3.88 (m, 1H), 3.77 (m, 1H), 3.35 (m, 1H), 2.77-2.66 (m, 2H), 2.62-2.52 (m, 1H), 2.40-2.29 (m, 3H), 2.22 (s, 3H), 2.15-2.05 (m, 1H), 2.03 (s, 3H), 1.99 (s, 3H), 1.61-1.53 (m, 3H), 0.88 (s, 9H)

Experimental procedures to key intermediates.

Example 1A

Preparation of 5-(4-chlorophenyl)-2-methylphenylboronic Acid

Step 1

4-Chlorophenylboronic acid (20.2 g, 0.13 mol) and tetrakis(triphenylphosphine)palladium (0) (3.7 g, 0.003 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 5-(4-chlorophenyl)-2-methylaniline (21.0 g).

Step 2

Hydrobromic acid (48% wt. in water, 120 ml) is added dropwise to a suspension of 5-(4-chlorophenyl)-2-methylaniline (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-methyl-1-bromobenzene (15.0 g).

Step 3

5-(4-chlorophenyl)-2-methyl-1-bromobenzene (5.0 g, 0.02 mol) is dissolved in THF (125 ml), and the temperature temperature is brought to −78° C. n-Butyllithium (1.33 molar solution in hexanes, 17.3 ml,) is added dropwise over 30 minutes, maintaining the temperature at around −78° C. The reaction mixture is stirred for one and half hours at −78° C., then trimethylborate (2.58 g, 0.024 mol) is added dropwise and the reaction mixture stirred for three and half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 5-(4-chlorophenyl)-2-methylphenylboronic acid (2.5 g).

Example 1B

Preparation of 5-(4-chlorophenyl)-2-ethylphenylboronic Acid

Step 1

Ammonium nitrate (39.6 g, 0.49 mol) is added portionwise to a chilled (ice-bath) solution of 4-ethylaniline (20 g, 0.16 mol) in concentrated sulfuric acid (100 ml, maintaining the temperature −10° to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and the extracted with ethyl acetate. The organic extracts are combined, dried over anhydrous sodium sulfate, filtered and the filtrate evaporated in vacuo to give 4-ethyl-3-nitroaniline (20 g).

Step 2

Hydrobromic acid (48% wt. in water, 240 ml) is added dropwise to a suspension of 4-ethyl-3-nitroaniline (20 g, 0.12 mol) in water (80 ml), and the mixture stirred until the solid is dissolved. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate concentrated in vacuo. The residue is further purified by column chromatography on silica gel, eluting with hexane to give 4-bromo-1-ethyl-2-nitrobenzene (18 g)

Step 3

A solution of ammonium chloride (12.5 g, 0.2 mol) in water (30 ml) is added to a mixture of zinc dust (35.7 g, 0.5 mol) and 4-bromo-1-ethyl-2-nitrobenzene (18 g, 0.07 mol) in methanol (720 ml) and water (180 ml). The reaction mixture is refluxed for one hour, then cooled to room temperature and filtered through a plug of diatomaceous earth. The filtrate is concentrated in vacuo, then diluted with water and extracted with ethyl acetate. The combined organic extracts are washed with water and brine, dried over anhydrous sodium sulfate, filtered and the filtrate concentrated in vacuo to yield 5-bromo-2-ethylaniline (14 g), used without further purification in the next step.

Step 4

4-Chlorophenylboronic acid (13.2 g, 0.08 mol) and tetrakis(triphenylphosphine) palladium (0) (2.4 g, 0.002 mol) are added to a solution of 5-bromo-2-ethylaniline (14.1 g, 0.07 mol) in 1,2-dimethoxyethane (140 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water and extracted using ethyl acetate. The combined organic extracts are dried over anhydrous sodium sulfate, filtered and the filtrate evaporated in vacuo. The residue is further purified by column chromatography on silica gel, eluting with 5% ethyl acetate in hexane to give 5-(4-chlorophenyl)-2-ethylaniline (14.3 g).

Step 5

Hydrobromic acid (48% wt. in water, 85 ml) is added dropwise to a suspension of 5-(4-chlorophenyl)-2-ethylaniline (14.3 g, 0.05 mol) in water (57 ml), and the mixture stirred. The mixture is cooled to −5° C. and a solution of sodium nitrite (5.07 g, 0.072 mol) in water (25 ml) is added dropwise, maintaining the temperature at 0-5° C. The reaction mixture is stirred for 1 hour, then added to a pre-cooled solution of cuprous bromide (9 g, 0.062 mol) in hydrobromic acid (48% wt. in water, 64 ml) at 0° C. The reaction mixture is stirred and allowed to warm to room temperature overnight. The mixture is diluted with water, extracted with diethyl ether, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-ethyl-1-bromobenzene (10 g).

Step 6

5-(4-chlorophenyl)-2-ethyl-1-bromobenzene (10 g, 0.03 mol) is dissolved in THF (250 ml), and the temperature is brought to −78° C. n-Butyllithium (1.33 molar solution in hexanes, 34.6 ml,) is added dropwise over 30 minutes, maintaining the temperature at around −78° C. The reaction mixture is stirred for one and half hours, then trimethylborate (4.9 g, 0.05 mol) is added dropwise and the reaction mixture stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate evaporated in vacuo. The residue is further purified by flash column chromatography on silica gel, eluting with 7% ethyl acetate in hexane to give 5-(4-chloro-phenyl)-2-methylphenylboronic acid (5.4 g).

Specific examples of the compounds of the invention include those compounds detailed in Table 1 to Table 81.

Table 1 covers 232 compounds of the following type

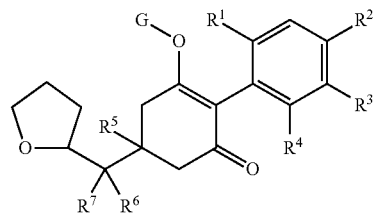

where G, $R^5$, $R^6$ and $R^7$ are all hydrogen, and $R^1$, $R^2$, $R^3$ and $R^4$ are as described in Table 1 below:

| Compound Number | $R^1$ | $R^2$ | $R^3$ | $R^4$ |
|---|---|---|---|---|
| 1.001 | $CH_3$ | H | H | H |
| 1.002 | $CH_3$ | $CH_3$ | H | H |
| 1.003 | $CH_3$ | H | $CH_3$ | H |
| 1.004 | $CH_3$ | H | H | $CH_3$ |
| 1.005 | $CH_3$ | $CH_3$ | $CH_3$ | H |
| 1.006 | $CH_3$ | $CH_3$ | H | $CH_3$ |
| 1.007 | $CH_3$ | $CH_3$ | $CH_3$ | $CH_3$ |
| 1.007 | $CH_3$ | Cl | H | H |
| 1.008 | $CH_3$ | Cl | H | $CH_3$ |
| 1.009 | $CH_3$ | Cl | H | $OCH_3$ |
| 1.010 | $CH_3$ | H | Cl | H |
| 1.011 | $CH_3$ | H | H | Cl |
| 1.012 | $CH_3$ | $CH_3$ | Cl | H |
| 1.013 | $CH_3$ | $CH_3$ | H | Cl |
| 1.014 | $CH_3$ | H | Cl | $CH_3$ |
| 1.015 | $CH_3$ | $CH_3$ | Cl | $CH_3$ |
| 1.016 | $CH_3$ | Br | H | H |
| 1.017 | $CH_3$ | Br | H | $CH_3$ |
| 1.018 | $CH_3$ | Br | H | $OCH_3$ |
| 1.019 | $CH_3$ | H | Br | H |
| 1.020 | $CH_3$ | H | H | Br |
| 1.021 | $CH_3$ | $CH_3$ | Br | H |
| 1.022 | $CH_3$ | $CH_3$ | H | Br |
| 1.023 | $CH_3$ | H | Br | $CH_3$ |
| 1.024 | $CH_3$ | $CH_3$ | Br | $CH_3$ |
| 1.025 | $CH_3$ | $CH_3O$ | H | H |
| 1.026 | $CH_3$ | $CH_3O$ | H | $CH_3$ |
| 1.027 | $CH_3$ | $CH_3O$ | H | Cl |
| 1.028 | $CH_3$ | $CH_3O$ | H | Br |
| 1.029 | $CH_3$ | $CH_3CH_2O$ | H | H |
| 1.030 | $CH_3$ | $CH_3CH_2O$ | H | $CH_3$ |
| 1.031 | $CH_3$ | $CH_3CH_2O$ | H | Cl |
| 1.032 | $CH_3$ | $CH_3CH_2O$ | H | Br |
| 1.033 | $CH_3$ | H | $CH_3O$ | H |
| 1.034 | $CH_3$ | H | H | $CH_3O$ |
| 1.035 | $CH_3$ | $CH_3$ | $CH_3O$ | H |

-continued

| Compound Number | R$^1$ | R$^2$ | R$^3$ | R$^4$ |
|---|---|---|---|---|
| 1.036 | CH$_3$ | CH$_3$ | H | CH$_3$O |
| 1.037 | CH$_3$ | H | CH$_3$O | CH$_3$ |
| 1.038 | CH$_3$ | CH$_3$ | CH$_3$O | CH$_3$ |
| 1.039 | CH$_3$ | —CH=CH$_2$ | H | CH$_3$ |
| 1.040 | CH$_3$ | CH$_3$ | H | —CH=CH$_2$ |
| 1.041 | CH$_3$ | —C•CH | H | CH$_3$ |
| 1.042 | CH$_3$ | CH$_3$ | H | —C•CH |
| 1.043 | CH$_3$ | —CH=CH$_2$ | H | —CH=CH$_2$ |
| 1.044 | CH$_3$ | CH$_2$CH$_3$ | H | CH$_3$ |
| 1.045 | CH$_3$ | phenyl | H | CH$_3$ |
| 1.046 | CH$_3$ | 2-fluorophenyl | H | CH$_3$ |
| 1.047 | CH$_3$ | 2-chlorophenyl | H | CH$_3$ |
| 1.048 | CH$_3$ | 2-trifluoromethylphenyl | H | CH$_3$ |
| 1.049 | CH$_3$ | 2-nitrophenyl | H | CH$_3$ |
| 1.050 | CH$_3$ | 2-methylphenyl | H | CH$_3$ |
| 1051 | CH$_3$ | 2-methanesulfonylphenyl | H | CH$_3$ |
| 1.052 | CH$_3$ | 2-cyanophenyl | H | CH$_3$ |
| 1.053 | CH$_3$ | 3-fluorophenyl | H | CH$_3$ |
| 1.054 | CH$_3$ | 3-chlorophenyl | H | CH$_3$ |
| 1.055 | CH$_3$ | 3-trifluoromethylphenyl | H | CH$_3$ |
| 1.056 | CH$_3$ | 3-nitrophenyl | H | CH$_3$ |
| 1.057 | CH$_3$ | 3-methylphenyl | H | CH$_3$ |
| 1.058 | CH$_3$ | 3-methanesulfonylphenyl | H | CH$_3$ |
| 1.059 | CH$_3$ | 3-cyanophenyl | H | CH$_3$ |
| 1.060 | CH$_3$ | 4-fluorophenyl | H | CH$_3$ |
| 1.061 | CH$_3$ | 4-chlorophenyl | H | CH$_3$ |
| 1.062 | CH$_3$ | 4-trifluoromethylphenyl | H | CH$_3$ |
| 1.063 | CH$_3$ | 4-nitrophenyl | H | CH$_3$ |
| 1.064 | CH$_3$ | 4-methylphenyl | H | CH$_3$ |
| 1.065 | CH$_3$ | 4-methanesulfonylphenyl | H | CH$_3$ |
| 1.066 | CH$_3$ | 4-cyanophenyl | H | CH$_3$ |
| 1.067 | CH$_3$ | H | phenyl | H |
| 1.068 | CH$_3$ | H | 2-fluorophenyl | H |
| 1.069 | CH$_3$ | H | 2-chlorophenyl | H |
| 1.070 | CH$_3$ | H | 2-trifluoromethylphenyl | H |
| 1.071 | CH$_3$ | H | 2-nitrophenyl | H |
| 1.072 | CH$_3$ | H | 2-methylphenyl | H |
| 1.073 | CH$_3$ | H | 2-methylsulfonylphenyl | H |
| 1.074 | CH$_3$ | H | 2-cyanophenyl | H |
| 1.075 | CH$_3$ | H | 3-fluorophenyl | H |
| 1.076 | CH$_3$ | H | 3-chlorophenyl | H |
| 1.077 | CH$_3$ | H | 3-trifluoromethylphenyl | H |
| 1.078 | CH$_3$ | H | 3-nitrophenyl | H |
| 1.080 | CH$_3$ | H | 3-methylphenyl | H |
| 1.081 | CH$_3$ | H | 3-methylsulfonylphenyl | H |
| 1.082 | CH$_3$ | H | 3-cyanophenyl | H |
| 1.083 | CH$_3$ | H | 4-fluorophenyl | H |
| 1.084 | CH$_3$ | H | 4-chlorophenyl | H |
| 1.085 | CH$_3$ | H | 4-trifluoromethylphenyl | H |
| 1.086 | CH$_3$ | H | 4-nitrophenyl | H |
| 1.087 | CH$_3$ | H | 4-methylphenyl | H |
| 1.088 | CH$_3$ | H | 4-methylsulfonylphenyl | H |
| 1.089 | CH$_3$ | H | 4-cyanophenyl | H |
| 1.090 | CH$_2$CH$_3$ | H | H | H |
| 1.091 | CH$_2$CH$_3$ | CH$_3$ | H | H |
| 1.092 | CH$_2$CH$_3$ | H | CH$_3$ | H |
| 1.093 | CH$_2$CH$_3$ | H | H | CH$_3$ |
| 1.094 | CH$_2$CH$_3$ | CH$_3$ | CH$_3$ | H |
| 1.095 | CH$_2$CH$_3$ | CH$_3$ | H | CH$_3$ |
| 1.096 | CH$_2$CH$_3$ | CH$_3$ | CH$_3$ | CH$_3$ |
| 1.097 | CH$_2$CH$_3$ | Cl | H | H |
| 1.098 | CH$_2$CH$_3$ | Cl | H | CH$_3$ |
| 1.099 | CH$_2$CH$_3$ | Cl | H | OCH$_3$ |
| 1.100 | CH$_2$CH$_3$ | H | Cl | H |
| 1.101 | CH$_2$CH$_3$ | H | H | Cl |
| 1.102 | CH$_2$CH$_3$ | CH$_3$ | Cl | H |
| 1.103 | CH$_2$CH$_3$ | CH$_3$ | H | Cl |
| 1.104 | CH$_2$CH$_3$ | H | Cl | CH$_3$ |
| 1.105 | CH$_2$CH$_3$ | CH$_3$ | Cl | CH$_3$ |
| 1.106 | CH$_2$CH$_3$ | Br | H | H |
| 1.107 | CH$_2$CH$_3$ | Br | H | CH$_3$ |
| 1.108 | CH$_2$CH$_3$ | Br | H | OCH$_3$ |
| 1.109 | CH$_2$CH$_3$ | H | Br | H |
| 1.110 | CH$_2$CH$_3$ | H | H | Br |
| 1.111 | CH$_2$CH$_3$ | CH$_3$ | Br | H |
| 1.112 | CH$_2$CH$_3$ | CH$_3$ | H | Br |
| 1.113 | CH$_2$CH$_3$ | H | Br | CH$_3$ |

-continued

| Compound Number | R$^1$ | R$^2$ | R$^3$ | R$^4$ |
|---|---|---|---|---|
| 1.114 | CH$_2$CH$_3$ | CH$_3$ | Br | CH$_3$ |
| 1.115 | CH$_2$CH$_3$ | CH$_3$O | H | H |
| 1.116 | CH$_2$CH$_3$ | CH$_3$O | H | CH$_3$ |
| 1.117 | CH$_2$CH$_3$ | CH$_3$O | H | Cl |
| 1.118 | CH$_2$CH$_3$ | CH$_3$O | H | Br |
| 1.119 | CH$_2$CH$_3$ | CH$_3$CH$_2$O | H | H |
| 1.120 | CH$_2$CH$_3$ | CH$_3$CH$_2$O | H | CH$_3$ |
| 1.121 | CH$_2$CH$_3$ | CH$_3$CH$_2$O | H | Cl |
| 1.122 | CH$_2$CH$_3$ | CH$_3$CH$_2$O | H | Br |
| 1.123 | CH$_2$CH$_3$ | H | CH$_3$O | H |
| 1.124 | CH$_2$CH$_3$ | H | H | CH$_3$O |
| 1.125 | CH$_2$CH$_3$ | CH$_3$ | CH$_3$O | H |
| 1.126 | CH$_2$CH$_3$ | CH$_3$ | H | CH$_3$O |
| 1.127 | CH$_2$CH$_3$ | H | CH$_3$O | CH$_3$ |
| 1.128 | CH$_2$CH$_3$ | CH$_3$ | CH$_3$O | CH$_3$ |
| 1.129 | CH$_2$CH$_3$ | —CH=CH$_2$ | H | CH$_3$ |
| 1.130 | CH$_2$CH$_3$ | CH$_3$ | H | —CH=CH$_2$ |
| 1.131 | CH$_2$CH$_3$ | —C•CH | H | CH$_3$ |
| 1.132 | CH$_2$CH$_3$ | CH$_3$ | H | —C•CH |
| 1.133 | CH$_2$CH$_3$ | —CH=CH$_2$ | H | —CH=CH$_2$ |
| 1.134 | CH$_2$CH$_3$ | CH$_2$CH$_3$ | H | CH$_3$ |
| 1.135 | CH$_2$CH$_3$ | phenyl | H | CH$_3$ |
| 1.136 | CH$_2$CH$_3$ | 2-fluorophenyl | H | CH$_3$ |
| 1.137 | CH$_2$CH$_3$ | 2-chlorophenyl | H | CH$_3$ |
| 1.138 | CH$_2$CH$_3$ | 2-trifluoromethylphenyl | H | CH$_3$ |
| 1.139 | CH$_2$CH$_3$ | 2-nitrophenyl | H | CH$_3$ |
| 1.140 | CH$_2$CH$_3$ | 2-methylphenyl | H | CH$_3$ |
| 1.141 | CH$_2$CH$_3$ | 2-methylsulfonylphenyl | H | CH$_3$ |
| 1.142 | CH$_2$CH$_3$ | 2-cyanophenyl | H | CH$_3$ |
| 1.143 | CH$_2$CH$_3$ | 3-fluorophenyl | H | CH$_3$ |
| 1.144 | CH$_2$CH$_3$ | 3-chlorophenyl | H | CH$_3$ |
| 1.145 | CH$_2$CH$_3$ | 3-trifluoromethylphenyl | H | CH$_3$ |
| 1.146 | CH$_2$CH$_3$ | 3-nitrophenyl | H | CH$_3$ |
| 1.147 | CH$_2$CH$_3$ | 3-methylphenyl | H | CH$_3$ |
| 1.148 | CH$_2$CH$_3$ | 3-methylsulfonylphenyl | H | CH$_3$ |
| 1.149 | CH$_2$CH$_3$ | 3-cyanophenyl | H | CH$_3$ |
| 1.150 | CH$_2$CH$_3$ | 4-fluorophenyl | H | CH$_3$ |
| 1.151 | CH$_2$CH$_3$ | 4-chlorophenyl | H | CH$_3$ |
| 1.152 | CH$_2$CH$_3$ | 4-trifluoromethylphenyl | H | CH$_3$ |
| 1.153 | CH$_2$CH$_3$ | 4-nitrophenyl | H | CH$_3$ |
| 1.154 | CH$_2$CH$_3$ | 4-methylphenyl | H | CH$_3$ |
| 1.155 | CH$_2$CH$_3$ | 4-methylsulfonylphenyl | H | CH$_3$ |
| 1.156 | CH$_2$CH$_3$ | 4-cyanophenyl | H | CH$_3$ |
| 1.157 | CH$_2$CH$_3$ | H | phenyl | H |
| 1.158 | CH$_2$CH$_3$ | H | 2-fluorophenyl | H |
| 1.159 | CH$_2$CH$_3$ | H | 2-chlorophenyl | H |
| 1.160 | CH$_2$CH$_3$ | H | 2-trifluoromethylphenyl | H |
| 1.161 | CH$_2$CH$_3$ | H | 2-nitrophenyl | H |
| 1.162 | CH$_2$CH$_3$ | H | 2-methylphenyl | H |
| 1.163 | CH$_2$CH$_3$ | H | 2-methylsulfonylphenyl | H |
| 1.164 | CH$_2$CH$_3$ | H | 2-cyanophenyl | H |
| 1.165 | CH$_2$CH$_3$ | H | 3-fluorophenyl | H |
| 1.166 | CH$_2$CH$_3$ | H | 3-chlorophenyl | H |
| 1.167 | CH$_2$CH$_3$ | H | 3-trifluoromethylphenyl | H |
| 1.168 | CH$_2$CH$_3$ | H | 3-nitrophenyl | H |
| 1.169 | CH$_2$CH$_3$ | H | 3-methylphenyl | H |
| 1.170 | CH$_2$CH$_3$ | H | 3-methylsulfonylphenyl | H |
| 1.1.71 | CH$_2$CH$_3$ | H | 3-cyanophenyl | H |
| 1.172 | CH$_2$CH$_3$ | H | 4-fluorophenyl | H |
| 1.173 | CH$_2$CH$_3$ | H | 4-chlorophenyl | H |
| 1.174 | CH$_2$CH$_3$ | H | 4-trifluoromethylphenyl | H |
| 1.175 | CH$_2$CH$_3$ | H | 4-nitrophenyl | H |
| 1.176 | CH$_2$CH$_3$ | H | 4-methylphenyl | H |
| 1.177 | CH$_2$CH$_3$ | H | 4-methylsulfonylphenyl | H |
| 1.178 | CH$_2$CH$_3$ | H | 4-cyanophenyl | H |
| 1.179 | CH$_2$CH$_3$ | CH$_3$ | H | CH$_2$CH$_3$ |
| 1.180 | CH$_2$CH$_3$ | CH$_2$CH$_3$ | H | CH$_2$CH$_3$ |
| 1.181 | CH$_2$CH$_3$ | Cl | H | CH$_2$CH$_3$ |
| 1.182 | CH$_2$CH$_3$ | Br | H | CH$_2$CH$_3$ |
| 1.183 | CH$_2$CH$_3$ | NO$_2$ | H | CH$_2$CH$_3$ |
| 1.184 | CH$_2$CH$_3$ | CH$_3$O | H | CH$_2$CH$_3$ |
| 1.185 | CH$_2$CH$_3$ | CH$_3$S | H | CH$_2$CH$_3$ |
| 1.186 | CH$_2$CH$_3$ | CH$_3$SO$_2$ | H | CH$_2$CH$_3$ |
| 1.187 | CH$_2$CH$_3$ | CH$_2$=CH | H | CH$_2$CH$_3$ |
| 1.188 | CH$_2$CH$_3$ | —C•CH | H | CH$_2$CH$_3$ |
| 1.189 | CH$_2$CH$_3$ | phenyl | H | CH$_2$CH$_3$ |
| 1.190 | CH$_2$CH$_3$ | 2-fluorophenyl | H | CH$_2$CH$_3$ |

-continued

| Compound Number | $R^1$ | $R^2$ | $R^3$ | $R^4$ |
|---|---|---|---|---|
| 1.191 | $CH_2CH_3$ | 2-chlorophenyl | H | $CH_2CH_3$ |
| 1.192 | $CH_2CH_3$ | 2-trifluoromethylphenyl | H | $CH_2CH_3$ |
| 1.193 | $CH_2CH_3$ | 2-nitrophenyl | H | $CH_2CH_3$ |
| 1.194 | $CH_2CH_3$ | 2-methylphenyl | H | $CH_2CH_3$ |
| 1.195 | $CH_2CH_3$ | 2-methylsulfonylphenyl | H | $CH_2CH_3$ |
| 1.196 | $CH_2CH_3$ | 2-cyanophenyl | H | $CH_2CH_3$ |
| 1.197 | $CH_2CH_3$ | 3-fluorophenyl | H | $CH_2CH_3$ |
| 1.198 | $CH_2CH_3$ | 3-chlorophenyl | H | $CH_2CH_3$ |
| 1.199 | $CH_2CH_3$ | 3-trifluoromethylphenyl | H | $CH_2CH_3$ |
| 1.200 | $CH_2CH_3$ | 3-nitrophenyl | H | $CH_2CH_3$ |
| 1.201 | $CH_2CH_3$ | 3-methylphenyl | H | $CH_2CH_3$ |
| 1.202 | $CH_2CH_3$ | 3-methylsulfonylphenyl | H | $CH_2CH_3$ |
| 1.203 | $CH_2CH_3$ | 3-cyanophenyl | H | $CH_2CH_3$ |
| 1.204 | $CH_2CH_3$ | 4-fluorophenyl | H | $CH_2CH_3$ |
| 1.205 | $CH_2CH_3$ | 4-chlorophenyl | H | $CH_2CH_3$ |
| 1.206 | $CH_2CH_3$ | 4-trifluoromethylphenyl | H | $CH_2CH_3$ |
| 1.207 | $CH_2CH_3$ | 4-nitrophenyl | H | $CH_2CH_3$ |
| 1.208 | $CH_2CH_3$ | 4-methylphenyl | H | $CH_2CH_3$ |
| 1.209 | $CH_2CH_3$ | 4-methylsulfonylphenyl | H | $CH_2CH_3$ |
| 1.210 | $CH_2CH_3$ | 4-cyanophenyl | H | $CH_2CH_3$ |
| 1.211 | $OCH_3$ | H | phenyl | H |
| 1.212 | $OCH_3$ | H | 2-fluorophenyl | H |
| 1.213 | $OCH_3$ | H | 2-chlorophenyl | H |
| 1.214 | $OCH_3$ | H | 2-trifluoromethylphenyl | H |
| 1.215 | $OCH_3$ | H | 2-nitrophenyl | H |
| 1.216 | $OCH_3$ | H | 2-methylphenyl | H |
| 1.217 | $OCH_3$ | H | 2-methylsulfonylphenyl | H |
| 1.218 | $OCH_3$ | H | 2-cyanophenyl | H |
| 1.219 | $OCH_3$ | H | 3-fluorophenyl | H |
| 1.220 | $OCH_3$ | H | 3-chlorophenyl | H |
| 1.221 | $OCH_3$ | H | 3-trifluoromethylphenyl | H |
| 1.222 | $OCH_3$ | H | 3-nitrophenyl | H |
| 1.223 | $OCH_3$ | H | 3-methylphenyl | H |
| 1.224 | $OCH_3$ | H | 3-methylsulfonylphenyl | H |
| 1.225 | $OCH_3$ | H | 3-cyanophenyl | H |
| 1.226 | $OCH_3$ | H | 4-fluorophenyl | H |
| 1.227 | $OCH_3$ | H | 4-chlorophenyl | H |
| 1.228 | $OCH_3$ | H | 4-trifluoromethylphenyl | H |
| 1.229 | $OCH_3$ | H | 4-nitrophenyl | H |
| 1.230 | $OCH_3$ | H | 4-methylphenyl | H |
| 1.231 | $OCH_3$ | H | 4-methylsulfonylphenyl | H |
| 1.232 | $OCH_3$ | H | 4-cyanophenyl | H |

Table 2 covers 232 compounds of the following type

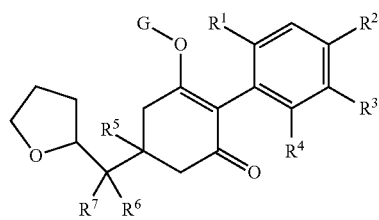

where G, $R^5$ and $R^6$ are hydrogen, $R^7$ is methyl and $R^1$, $R^2$, $R^3$ and $R^4$ are as described in Table 1.

Table 3 covers 232 compounds of the following type

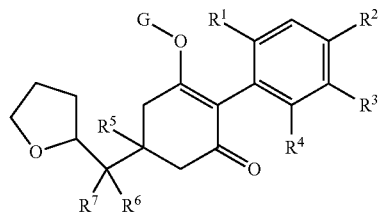

where G and $R^5$ are hydrogen, $R^6$ and $R^7$ are methyl and $R^1$, $R^2$, $R^3$ and $R^4$ are as described in Table 1.

Table 4 covers 232 compounds of the following type

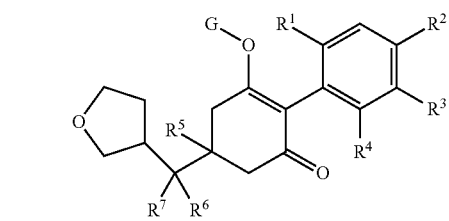

where G, $R^5$, $R^6$ and $R^7$ are all hydrogen, and $R^1$, $R^2$, $R^3$ and $R^4$ are as described in Table 1.

Table 5 covers 232 compounds of the following type

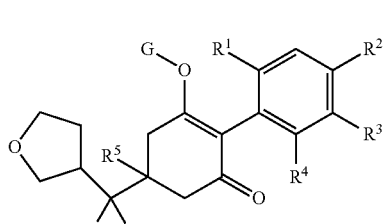

where G, R⁵ and R⁶ are hydrogen, R⁷ is methyl and R¹, R², R³ and R⁴ are as described in Table 1.

Table 6 covers 232 compounds of the following type

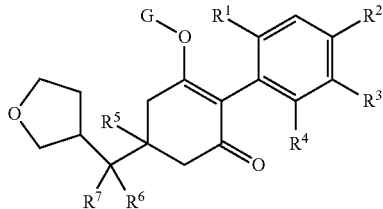

where G and R⁵ are hydrogen, R⁶ and R⁷ are methyl and R¹, R², R³ and R⁴ are as described in Table 1.

Table 7 covers 232 compounds of the following type

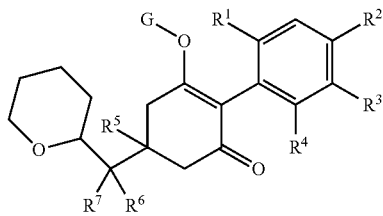

where G, R⁵ R⁶ and R⁷ are all hydrogen, and R¹, R², R³ and R⁴ are as described in Table 1.

Table 8 covers 232 compounds of the following type

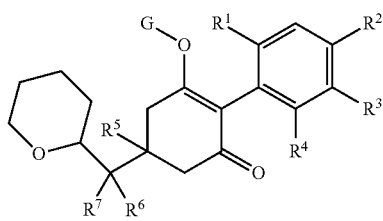

where G, R⁵ and R⁶ are hydrogen, R⁷ is methyl and R¹, R², R³ and R⁴ are as described in Table 1.

Table 9 covers 232 compounds of the following type

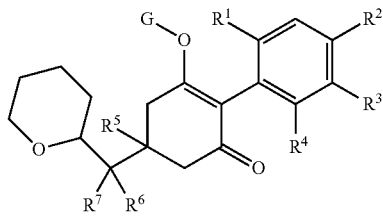

where G and R⁵ are hydrogen, R⁶ and R⁷ are methyl and R¹, R², R³ and R⁴ are as described in Table 1

Table 10 covers 232 compounds of the following type

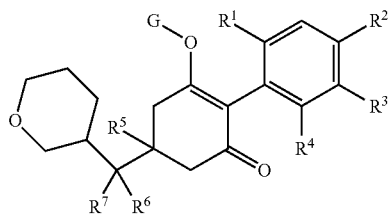

where G, R⁵, R⁶ and R⁷ are all hydrogen, and R¹, R², R³ and R⁴ are as described in Table 1.

Table 11 covers 232 compounds of the following type

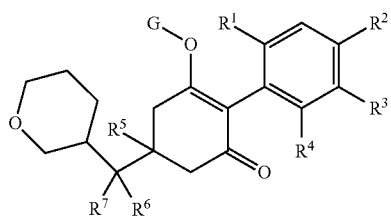

where G, R⁵ and R⁶ are hydrogen, R⁷ is methyl and R¹, R², R³ and R⁴ are as described in Table 1.

Table 12 covers 232 compounds of the following type

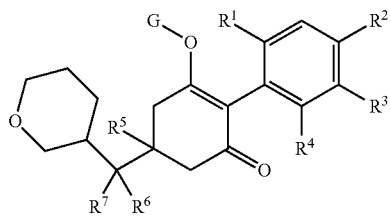

where G and R⁵ are hydrogen, R⁶ and R⁷ are methyl and R¹, R², R³ and R⁴ are as described in Table 1.

Table 13 covers 232 compounds of the following type

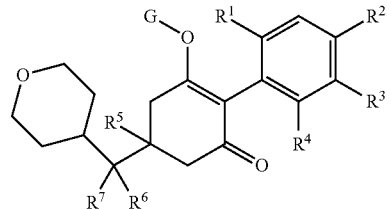

where G, R⁵, R⁶ and R⁷ are all hydrogen, and R¹, R², R³ and R⁴ are as described in Table 1.

Table 14 covers 232 compounds of the following type

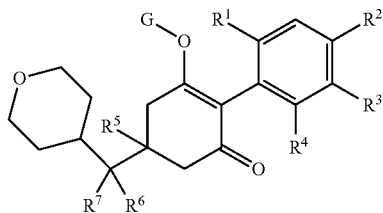

where G, R⁵ and R⁶ are hydrogen, R⁷ is methyl and R¹, R², R³ and R⁴ are as described in Table 1.

Table 15 covers 232 compounds of the following type

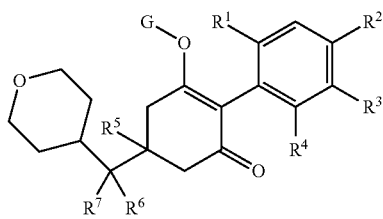

where G and R⁵ are hydrogen, R⁶ and R⁷ are methyl and R¹, R², R³ and R⁴ are as described in Table 1.

Table 16 covers 232 compounds of the following type

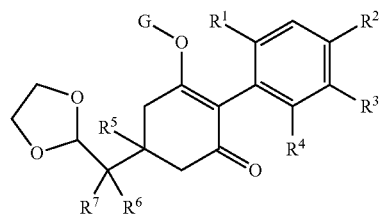

where G, R⁵, R⁶ and R⁷ are all hydrogen, and R¹, R², R³ and R⁴ are as described in Table 1.

Table 17 covers 232 compounds of the following type

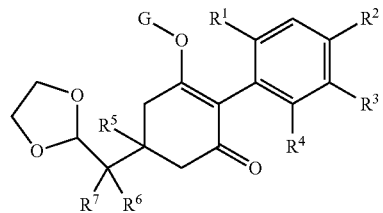

where G, R⁵ and R⁶ are hydrogen, R⁷ is methyl and R¹, R², R³ and R⁴ are as described in Table 1.

Table 18 covers 232 compounds of the following type

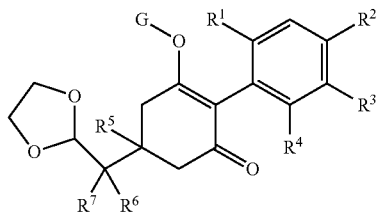

where G and R⁵ are hydrogen, R⁶ and R⁷ are methyl and R¹, R², R³ and R⁴ are as described in Table 1

Table 19 covers 232 compounds of the following type

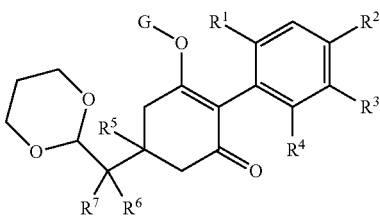

where G, R⁵, R⁶ and R⁷ are all hydrogen, and R¹, R², R³ and R⁴ are as described in Table 1.

Table 20 covers 232 compounds of the following type

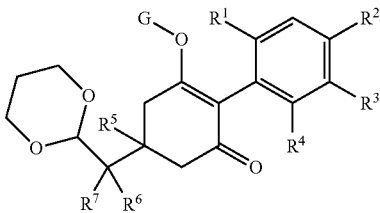

where G, R⁵ and R⁶ are hydrogen, R⁷ is methyl and R¹, R², R³ and R⁴ are as described in Table 1.

Table 21 covers 232 compounds of the following type

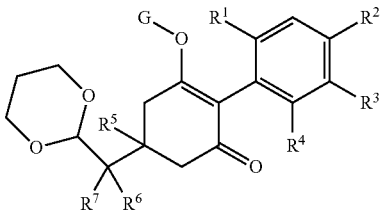

where G and R⁵ are hydrogen, R⁶ and R⁷ are methyl and R¹, R², R³ and R⁴ are as described in Table 1.

Table 22 covers 232 compounds of the following type

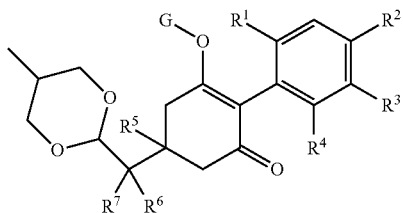

where G, R⁵, R⁶ and R⁷ are all hydrogen, and R¹, R², R³ and R⁴ are as described in Table 1.

Table 23 covers 232 compounds of the following type

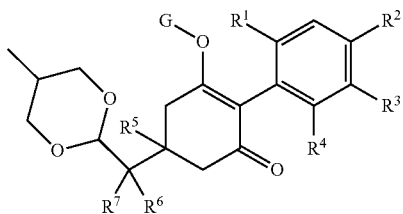

where G, R⁵ and R⁶ are hydrogen, R⁷ is methyl and R¹, R², R³ and R⁴ are as described in Table 1

Table 24 covers 232 compounds of the following type

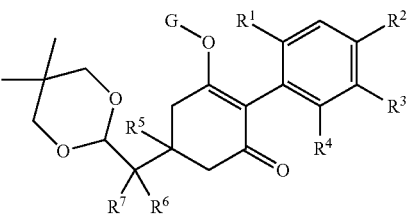

where G, R⁵, R⁶ and R⁷ are all hydrogen, and R¹, R², R³ and R⁴ are as described in Table 1.

Table 25 covers 232 compounds of the following type

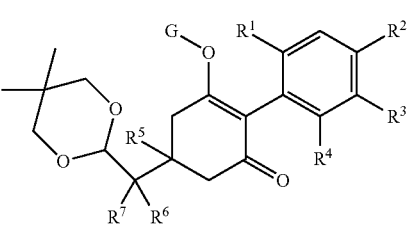

where G, R⁵ and R⁶ are hydrogen, R⁷ is methyl and R¹, R², R³ and R⁴ are as described in Table 1.

Table 26 covers 232 compounds of the following type

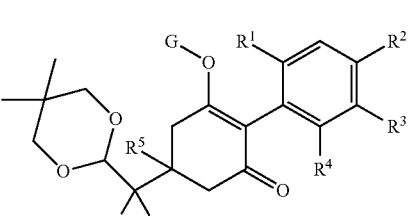

where G, R⁵, R⁶ and R⁷ are all hydrogen, and R¹, R², R³ and R⁴ are as described in Table 1.

Table 27 covers 232 compounds of the following type

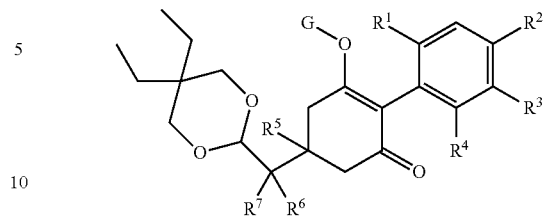

where G, R⁵ and R⁶ are hydrogen, R⁷ is methyl and R¹, R², R³ and R⁴ are as described in Table 1.

Table 28 covers 232 compounds of the following type

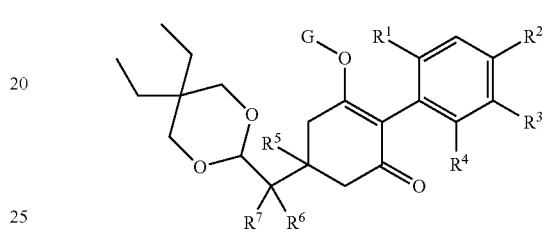

where G and R⁵ are hydrogen, R⁶ and R⁷ are methyl and R¹, R², R³ and R⁴ are as described in Table 1.

Table 29 covers 232 compounds of the following type

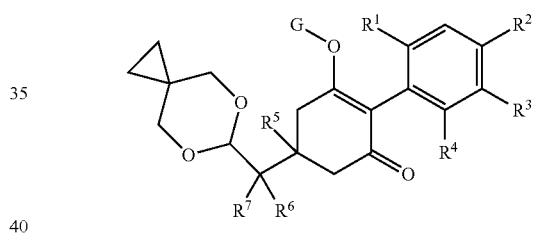

where G, R⁵, R⁶ and R⁷ are all hydrogen, and R¹, R², R³ and R⁴ are as described in Table 1.

Table 30 covers 232 compounds of the following type

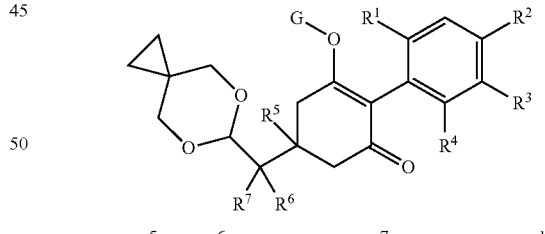

where G, R⁵ and R⁶ are hydrogen, R⁷ is methyl and R¹, R², R³ and R⁴ are as described in Table 1.

Table 31 covers 232 compounds of the following type

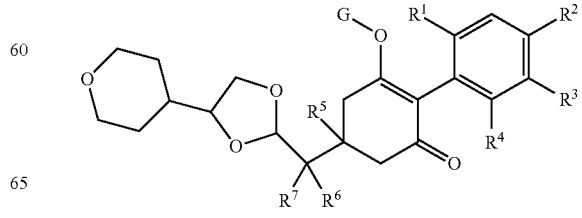

where G, $R^5$, $R^6$ and $R^7$ are all hydrogen, and $R^1$, $R^2$, $R^3$ and $R^4$ are as described in Table 1.

Table 32 covers 232 compounds of the following type

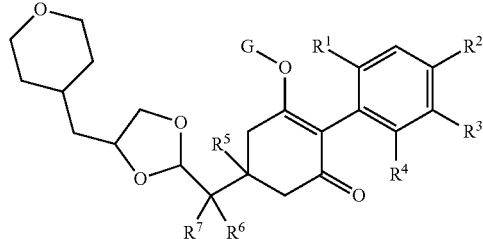

where G, $R^5$, $R^6$ and $R^7$ are all hydrogen, and $R^1$, $R^2$, $R^3$ and $R^4$ are as described in Table 1.

Table 33 covers 232 compounds of the following type

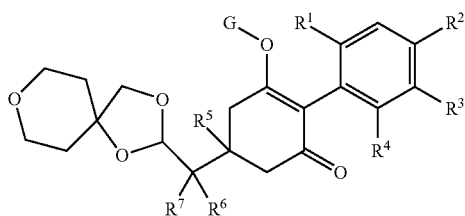

where G, $R^5$, $R^6$ and $R^7$ are all hydrogen, and $R^1$, $R^2$, $R^3$ and $R^4$ are as described in Table 1.

Table 34 covers 232 compounds of the following type

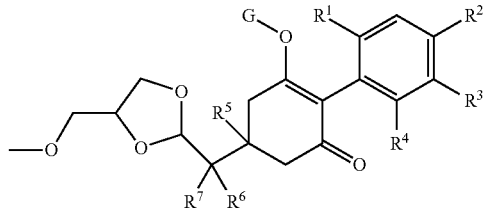

where G, $R^5$, $R^6$ and $R^7$ are all hydrogen, and $R^1$, $R^2$, $R^3$ and $R^4$ are as described in Table 1.

Table 35 covers 232 compounds of the following type

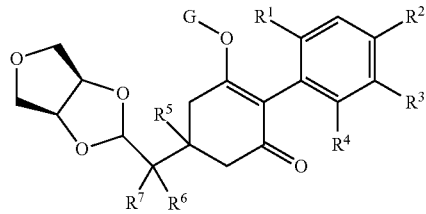

where G, $R^5$, $R^6$ and $R^7$ are all hydrogen, and $R^1$, $R^2$, $R^3$ and $R^4$ are as described in Table 1.

Table 36 covers 232 compounds of the following type

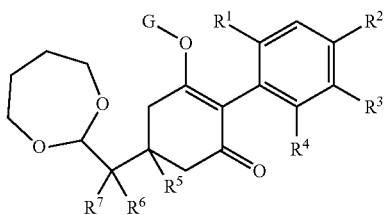

where G, $R^5$, $R^6$ and $R^7$ are all hydrogen, and $R^1$, $R^2$, $R^3$ and $R^4$ are as described in Table 1.

Table 37 covers 232 compounds of the following type

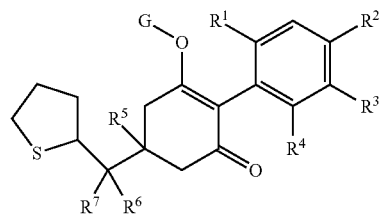

where G, $R^5$, $R^6$ and $R^7$ are all hydrogen, and $R^1$, $R^2$, $R^3$ and $R^4$ are as described in Table 1.

Table 38 covers 232 compounds of the following type

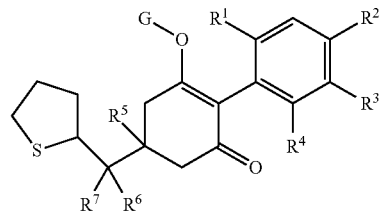

where G, $R^5$ and $R^6$ are hydrogen, $R^7$ is methyl and $R^1$, $R^2$, $R^3$ and $R^4$ are as described in Table 1.

Table 39 covers 232 compounds of the following type

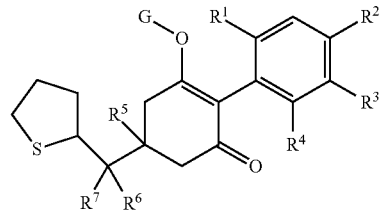

where G and $R^5$ are hydrogen, $R^6$ and $R^7$ are methyl and $R^1$, $R^2$, $R^3$ and $R^4$ are as described in Table 1.

Table 40 covers 232 compounds of the following type

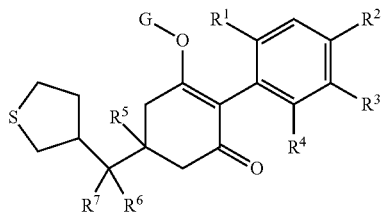

where G, $R^5$, $R^6$ and $R^7$ are all hydrogen, and $R^1$, $R^2$, $R^3$ and $R^4$ are as described in Table 1.

Table 41 covers 232 compounds of the following type

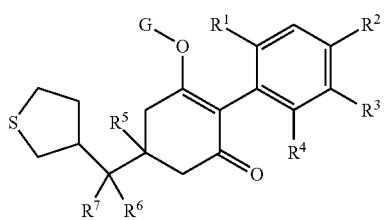

where G, $R^5$ and $R^6$ are hydrogen, $R^7$ is methyl and $R^1$, $R^2$, $R^3$ and $R^4$ are as described in Table 1.

Table 42 covers 232 compounds of the following type

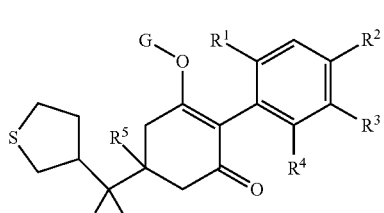

where G and $R^5$ are hydrogen, $R^6$ and $R^7$ are methyl and $R^1$, $R^2$, $R^3$ and $R^4$ are as described in Table 1.

Table 43 covers 232 compounds of the following type

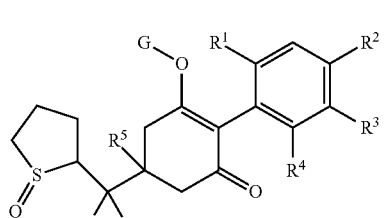

where G, $R^5$, $R^6$ and $R^7$ are all hydrogen, and $R^1$, $R^2$, $R^3$ and $R^4$ are as described in Table 1.

Table 44 covers 232 compounds of the following type

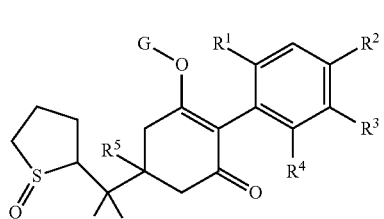

where G, $R^5$ and $R^6$ are hydrogen, $R^7$ is methyl and $R^1$, $R^2$, $R^3$ and $R^4$ are as described in Table 1.

Table 45 covers 232 compounds of the following type

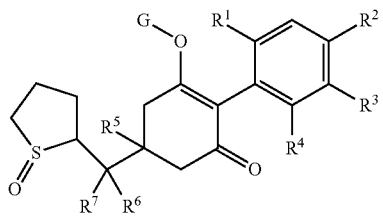

where G and $R^5$ are hydrogen, $R^6$ and $R^7$ are methyl and $R^1$, $R^2$, $R^3$ and $R^4$ are as described in Table 1.

Table 46 covers 232 compounds of the following type

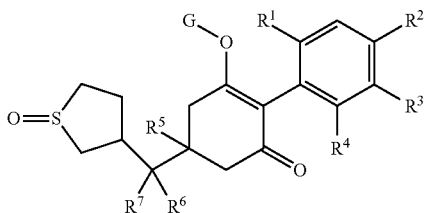

where G, $R^5$, $R^6$ and $R^7$ are all hydrogen, and $R^1$, $R^2$, $R^3$ and $R^4$ are as described in Table 1.

Table 47 covers 232 compounds of the following type

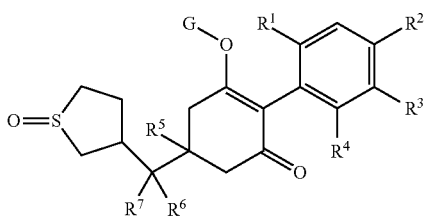

where G, $R^5$ and $R^6$ are hydrogen, $R^7$ is methyl and $R^1$, $R^2$, $R^3$ and $R^4$ are as described in Table 1.

Table 48 covers 232 compounds of the following type

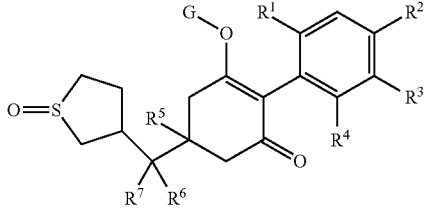

where G and $R^5$ are hydrogen, $R^6$ and $R^7$ are methyl and $R^1$, $R^2$, $R^3$ and $R^4$ are as described in Table 1.

Table 49 covers 232 compounds of the following type

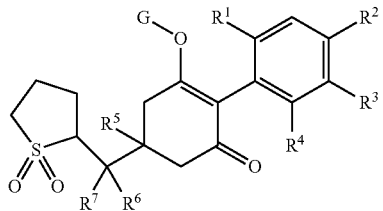

where G, R⁵, R⁶ and R⁷ are all hydrogen, and R¹, R², R³ and R⁴ are as described in Table 1.

Table 50 covers 232 compounds of the following type

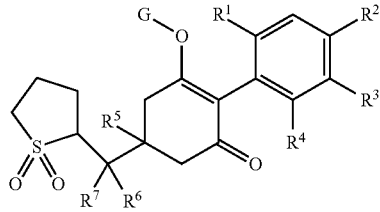

where G, R⁵ and R⁶ are hydrogen, R⁷ is methyl and R¹, R², R³ and R⁴ are as described in Table 1.

Table 51 covers 232 compounds of the following type

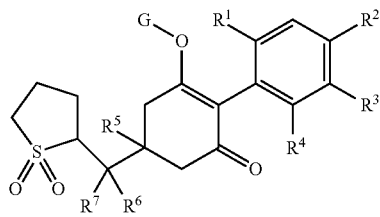

where G and R⁵ are hydrogen, R⁶ and R⁷ are methyl and R¹, R², R³ and R⁴ are as described in Table 1.

Table 52 covers 232 compounds of the following type

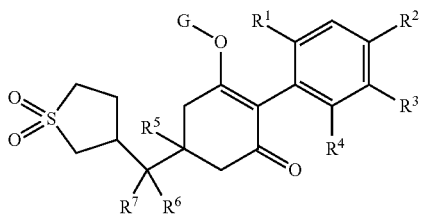

where G, R⁵, R⁶ and R⁷ are all hydrogen, and R¹, R², R³ and R⁴ are as described in Table 1.

Table 53 covers 232 compounds of the following type

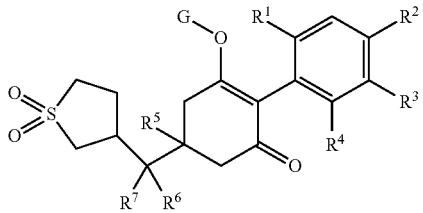

where G, R⁵ and R⁶ are hydrogen, R⁷ is methyl and R¹, R², R³ and R⁴ are as described in Table 1.

Table 54 covers 232 compounds of the following type

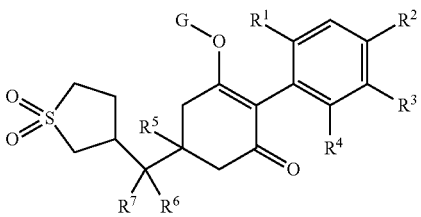

where G and R⁵ are hydrogen, R⁶ and R⁷ are methyl and R¹, R², R³ and R⁴ are as described in Table 1.

Table 55 covers 232 compounds of the following type

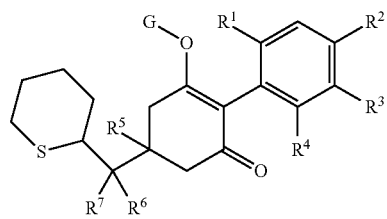

where G, R⁵, R⁶ and R⁷ are all hydrogen, and R¹, R², R³ and R⁴ are as described in Table 1.

Table 56 covers 232 compounds of the following type

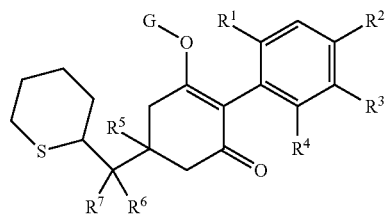

where G, R⁵ and R⁶ are hydrogen, R⁷ is methyl and R¹, R², R³ and R⁴ are as described in Table 1.

Table 57 covers 232 compounds of the following type

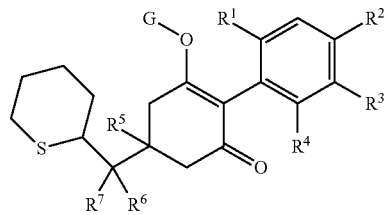

where G and R⁵ are hydrogen, R⁶ and R⁷ are methyl and R¹, R², R³ and R⁴ are as described in Table 1.

Table 58 covers 232 compounds of the following type

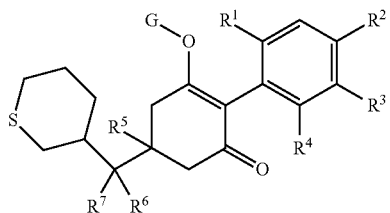

where G, $R^5$, $R^6$ and $R^7$ are all hydrogen, and $R^1$, $R^2$, $R^3$ and $R^4$ are as described in Table 1.

Table 59 covers 232 compounds of the following type

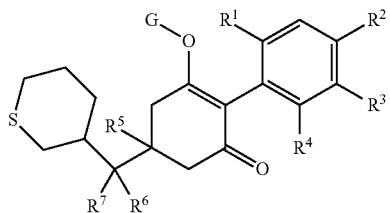

where G, $R^5$ and $R^6$ are hydrogen, $R^7$ is methyl and $R^1$, $R^2$, $R^3$ and $R^4$ are as described in Table 1.

Table 60 covers 232 compounds of the following type

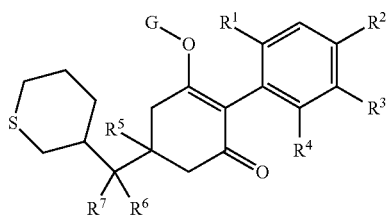

where G and $R^5$ are hydrogen, $R^6$ and $R^7$ are methyl and $R^1$, $R^2$, $R^3$ and $R^4$ are as described in Table 1.

Table 61 covers 232 compounds of the following type

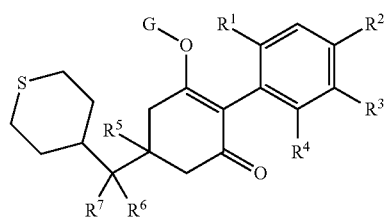

where G, $R^5$, $R^6$ and $R^7$ are all hydrogen, and $R^1$, $R^2$, $R^3$ and $R^4$ are as described in Table 1.

Table 62 covers 232 compounds of the following type

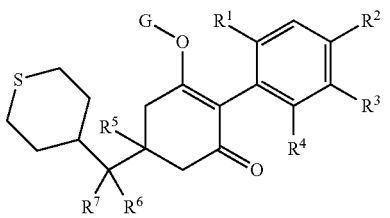

where G, $R^5$ and $R^6$ are hydrogen, $R^7$ is methyl and $R^1$, $R^2$, $R^3$ and $R^4$ are as described in Table 1.

Table 63 covers 232 compounds of the following type

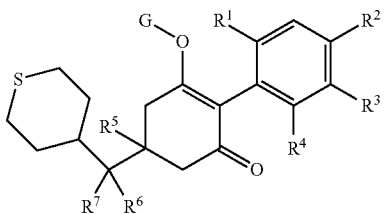

where G and $R^5$ are hydrogen, $R^6$ and $R^7$ are methyl and $R^1$, $R^2$, $R^3$ and $R^4$ are as described in Table 1.

Table 64 covers 232 compounds of the following type

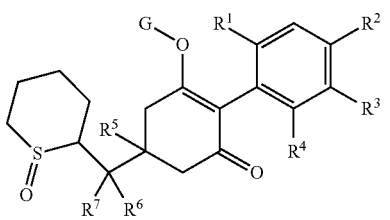

where G, $R^5$, $R^6$ and $R^7$ are all hydrogen, and $R^1$, $R^2$, $R^3$ and $R^4$ are as described in Table 1.

Table 65 covers 232 compounds of the following type

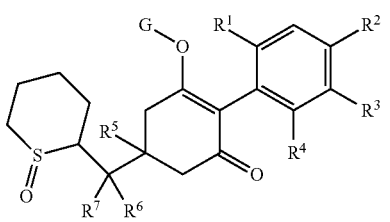

where G, $R^5$ and $R^6$ are hydrogen, $R^7$ is methyl and $R^1$, $R^2$, $R^3$ and $R^4$ are as described in Table 1.

Table 66 covers 232 compounds of the following type

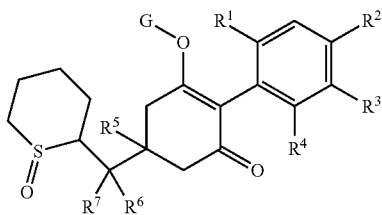

where G and R⁵ are hydrogen, R⁶ and R⁷ are methyl and $R^1$, $R^2$, $R^3$ and $R^4$ are as described in Table 1.

Table 67 covers 232 compounds of the following type

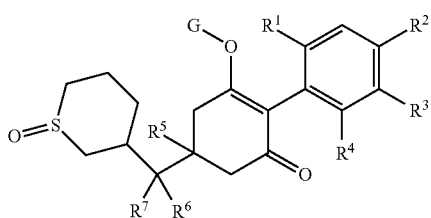

where G, $R^5$, $R^6$ and $R^7$ are all hydrogen, and $R^1$, $R^2$, $R^3$ and $R^4$ are as described in Table 1.

Table 68 covers 232 compounds of the following type

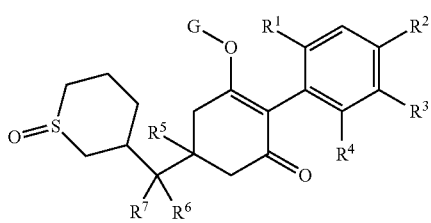

where G, $R^5$ and $R^6$ are hydrogen, $R^7$ is methyl and $R^1$, $R^2$, $R^3$ and $R^4$ are as described in Table 1.

Table 69 covers 232 compounds of the following type

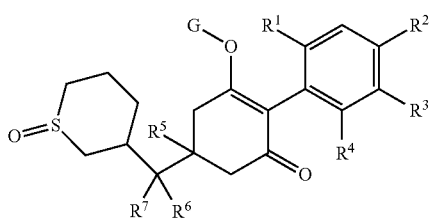

where G and $R^5$ are hydrogen, $R^6$ and $R^7$ are methyl and $R^1$, $R^2$, $R^3$ and $R^4$ are as described in Table 1.

Table 70 covers 232 compounds of the following type

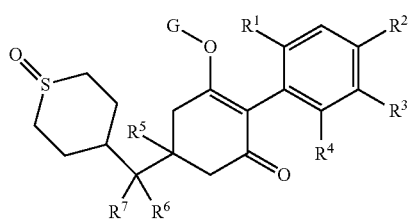

where G, $R^5$, $R^6$ and $R^7$ are all hydrogen, and $R^1$, $R^2$, $R^3$ and $R^4$ are as described in Table 1.

Table 71 covers 232 compounds of the following type

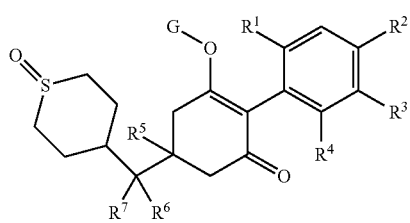

where G, $R^5$ and $R^6$ are hydrogen, $R^7$ is methyl and $R^1$, $R^2$, $R^3$ and $R^4$ are as described in Table 1.

Table 72 covers 232 compounds of the following type

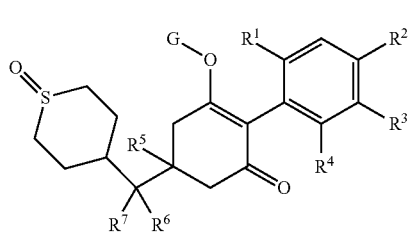

where G and $R^5$ are hydrogen, $R^6$ and $R^7$ are methyl and $R^1$, $R^2$, $R^3$ and $R^4$ are as described in Table 1.

Table 73 covers 232 compounds of the following type

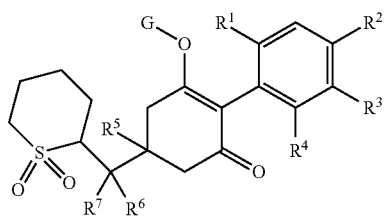

where G, $R^5$, $R^6$ and $R^7$ are all hydrogen, and $R^1$, $R^2$, $R^3$ and $R^4$ are as described in Table 1.

Table 74 covers 232 compounds of the following type

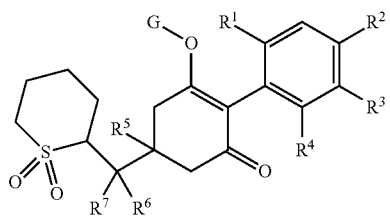

where G, R$^5$ and R$^6$ are hydrogen, R$^7$ is methyl and R$^1$, R$^2$, R$^3$ and R$^4$ are as described in Table 1.

Table 75 covers 232 compounds of the following type

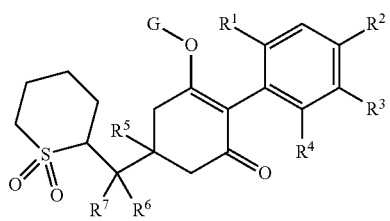

where G and R$^5$ are hydrogen, R$^6$ and R$^7$ are methyl and R$^1$, R$^2$, R$^3$ and R$^4$ are as described in Table 1.

Table 76 covers 232 compounds of the following type

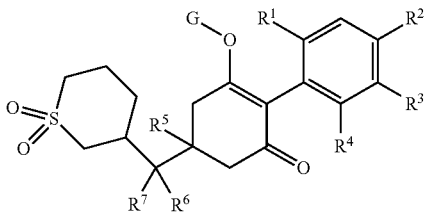

where G, R$^5$, R$^6$ and R$^7$ are all hydrogen, and R$^1$, R$^2$, R$^3$ and R$^4$ are as described in Table 1.

Table 77 covers 232 compounds of the following type

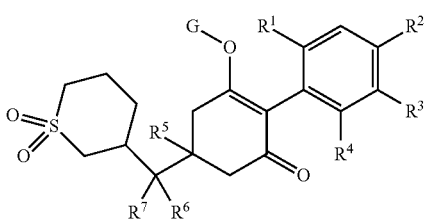

where G, R$^5$ and R$^6$ are hydrogen, R$^7$ is methyl and R$^1$, R$^2$, R$^3$ and R$^4$ are as described in Table 1.

Table 78 covers 232 compounds of the following type

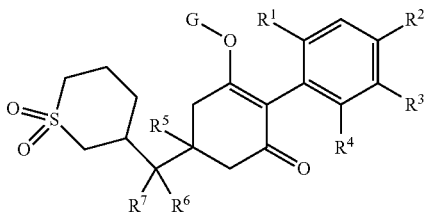

where G and R$^5$ are hydrogen, R$^6$ and R$^7$ are methyl and R$^1$, R$^2$, R$^3$ and R$^4$ are as described in Table 1.

Table 79 covers 232 compounds of the following type

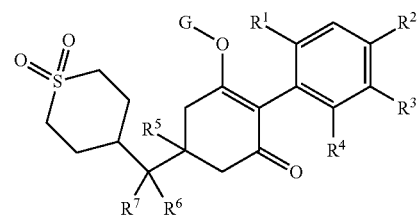

where G, R$^5$, R$^6$ and R$^7$ are all hydrogen, and R$^1$, R$^2$, R$^3$ and R$^4$ are as described in Table 1.

Table 80 covers 232 compounds of the following type

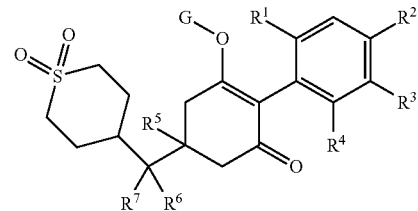

where G, R$^5$ and R$^6$ are hydrogen, R$^7$ is methyl and R$^1$, R$^2$, R$^3$ and R$^4$ are as described in Table 1.

Table 81 covers 232 compounds of the following type

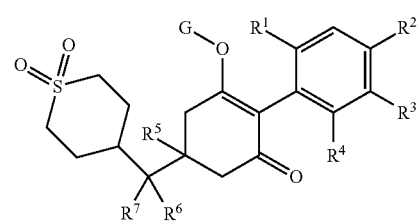

where G and R$^5$ are hydrogen, R$^6$ and R$^7$ are methyl and R$^1$, R$^2$, R$^3$ and R$^4$ are as described in Table 1.

Biological Examples

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

Pre-Emergence Activity

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

| Compound Number | Rate g/ha | ALOMY | AVEFA | LOLPE | SETFA | DIGSA | ECHCG |
|---|---|---|---|---|---|---|---|
| A-1 | 500 | 70 | 40 | 80 | 90 | 100 | 50 |
| A-2 | 500 | 20 | 40 | 10 | 60 | 50 | 100 |
| A-3 | 500 | 80 | 90 | 100 | 100 | 100 | 100 |
| A-4 | 500 | 60 | 40 | 30 | 80 | 70 | 100 |
| A-5 | 500 | 100 | 100 | 100 | 100 | 100 | 100 |
| A-6 | 500 | 90 | 60 | 70 | 80 | 100 | 100 |
| A-7 | 500 | 100 | 100 | 100 | 80 | 100 | 100 |
| A-8 | 500 | 100 | 50 | 100 | 70 | 100 | 70 |
| A-9 | 500 | 100 | 60 | 100 | 90 | 100 | 70 |
| A-10 | 500 | 50 | 50 | 70 | 60 | 60 | 80 |
| A-11 | 500 | 100 | 100 | 100 | — | — | 70 |
| A-12 | 500 | — | 40 | 100 | 60 | 70 | 70 |
| A-13 | 500 | 30 | 20 | 10 | 30 | 30 | 30 |
| A-14 | 500 | 80 | 70 | 90 | 100 | 100 | 80 |
| A-15 | 500 | 10 | 40 | 0 | 20 | 20 | 10 |
| A-16 | 500 | 100 | 90 | 100 | — | 100 | 100 |
| A-17 | 500 | 100 | 100 | 100 | 100 | 100 | 100 |
| A-18 | 500 | 90 | 100 | 100 | 100 | 100 | 100 |
| A-19 | 500 | 100 | 60 | 100 | 100 | 100 | 100 |
| A-20 | 500 | 50 | 10 | 40 | 70 | 40 | 100 |
| A-31 | 500 | 60 | 50 | 40 | 100 | 100 | 70 |
| B-1 | 500 | 90 | 50 | 90 | 80 | 100 | 100 |

Post Emergency Activity

| Compound Number | Rate g/ha | ALOMY | AVEFA | LOLPE | SETFA | DIGSA | ECHCG |
|---|---|---|---|---|---|---|---|
| A-1 | 500 | 70 | 80 | 70 | 100 | 100 | 90 |
| A-2 | 500 | 70 | 40 | 50 | 90 | 90 | 100 |
| A-3 | 500 | 80 | 80 | 80 | 80 | 100 | 100 |
| A-4 | 500 | 80 | 70 | 70 | 100 | 100 | 100 |
| A-5 | 500 | 90 | 90 | 90 | 100 | 90 | 100 |
| A-6 | 500 | 80 | 100 | 80 | 80 | 90 | 100 |
| A-7 | 500 | 90 | 100 | 90 | 80 | 80 | 100 |
| A-8 | 500 | 60 | 50 | 80 | 70 | 70 | 100 |
| A-9 | 500 | 80 | 70 | 80 | 80 | 70 | 90 |
| A-10 | 500 | 80 | 80 | 60 | 50 | 70 | 50 |
| A-11 | 500 | 100 | 90 | 90 | 80 | 90 | 100 |
| A-12 | 500 | 80 | 80 | 80 | 70 | 70 | 80 |
| A-13 | 500 | 80 | 30 | 70 | 50 | 90 | 100 |
| A-14 | 500 | 100 | 100 | 90 | 100 | 70 | 100 |
| A-15 | 500 | 60 | 30 | 30 | 30 | 70 | 50 |
| A-16 | 500 | 60 | 90 | 90 | 80 | 100 | 70 |
| A-17 | 125 | 90 | 100 | 90 | 50 | 80 | 100 |
| A-18 | 125 | 100 | 90 | 100 | 50 | 80 | 100 |
| A-19 | 125 | 70 | 20 | 70 | 60 | 60 | 70 |
| A-20 | 125 | 40 | 60 | 40 | 80 | 100 | 100 |
| A-31 | 125 | 60 | 60 | 60 | 40 | 30 | 50 |
| B-1 | 500 | 50 | 0 | 60 | 80 | 90 | 70 |

Test Plants:

Alopecurus myosuroides (ALOMY), Avena fatua (AVEFA), Setaria faberi (SETFA), Echinochloa crus-galli (ECHCG), Solanum nigrum (SOLNI) and Amaranthus retroflexus (AMARE)

Pre-Emergence Activity

| Compound Number | Rate g/ha | SOLNI | AMARE | SETFA | ALOMY | ECHCG | AVEFA |
|---|---|---|---|---|---|---|---|
| A-27 | 1000 | 0 | 0 | 0 | 0 | 0 | 0 |
| A-29 | 1000 | 30 | 50 | 0 | 20 | 20 | 0 |
| A-31 | 1000 | 0 | 0 | 100 | 100 | 100 | 40 |
| A-33 | 1000 | 0 | 0 | 100 | 50 | 90 | 60 |
| A-34 | 1000 | 0 | 0 | 90 | 50 | 100 | 60 |
| A-36 | 1000 | 0 | 0 | 100 | 60 | 90 | 40 |
| A-37 | 1000 | 20 | 20 | 100 | 80 | 100 | 90 |
| A-38 | 1000 | 0 | 0 | 100 | 30 | 100 | 20 |
| A-39 | 1000 | 0 | 0 | 0 | 0 | 0 | 0 |
| A-40 | 1000 | 0 | 0 | 0 | 0 | 30 | 0 |
| A-41 | 1000 | 0 | 0 | 100 | 90 | 100 | 80 |
| A-45 | 1000 | 100 | 0 | 90 | 60 | 100 | 70 |
| A-46 | 1000 | 0 | 0 | 90 | 20 | 40 | 40 |
| A-48 | 1000 | 0 | 0 | 20 | 0 | 20 | 0 |
| A-53 | 1000 | 0 | 0 | 0 | 0 | 0 | 0 |
| A-54 | 1000 | 0 | 0 | 0 | 60 | 0 | 10 |
| A-55 | 1000 | 0 | 0 | 60 | 0 | 60 | 20 |
| A-56 | 1000 | 0 | 0 | 70 | 20 | 0 | 0 |
| A-57 | 1000 | 0 | 0 | 90 | 40 | 0 | 0 |
| A-58 | 1000 | 0 | 0 | 30 | 20 | 60 | 0 |
| A-59 | 1000 | 0 | 0 | 60 | 20 | 0 | 0 |
| A-60 | 1000 | 0 | 0 | 30 | 0 | 30 | 0 |
| A-61 | 1000 | 0 | 0 | 30 | 0 | 20 | 0 |
| A-62 | 1000 | 0 | 0 | 60 | 20 | 50 | 0 |
| A-63 | 1000 | 0 | 20 | 70 | 0 | 20 | 0 |
| A-64 | 1000 | 0 | 0 | 50 | 0 | 50 | 0 |
| A-65 | 1000 | 20 | 30 | 60 | 20 | 70 | 0 |

Post-Emergence Activity

| Compound Number | Rate g/ha | SOLNI | AMARE | SETFA | ALOMY | ECHCG | AVEFA |
|---|---|---|---|---|---|---|---|
| A-27 | 1000 | 0 | 0 | 60 | 10 | 30 | 0 |
| A-29 | 1000 | 20 | 70 | 60 | 10 | 60 | 0 |
| A-31 | 1000 | 0 | 0 | 100 | 100 | 100 | 90 |
| A-33 | 1000 | 70 | 60 | 80 | 30 | 100 | 70 |
| A-34 | 1000 | 0 | 20 | 90 | 50 | 100 | 100 |
| A-36 | 1000 | 50 | 0 | 100 | 70 | 100 | 70 |
| A-37 | 1000 | 70 | 40 | 100 | 90 | 100 | 100 |
| A-38 | 1000 | 20 | 0 | 100 | 30 | 90 | 40 |
| A-39 | 1000 | 0 | 0 | 90 | 60 | 80 | 80 |
| A-40 | 1000 | 0 | 30 | 90 | 70 | 100 | 70 |
| A-41 | 1000 | 40 | 40 | 100 | 90 | 100 | 70 |
| A-45 | 1000 | 10 | 0 | 100 | 100 | 100 | 100 |
| A-46 | 1000 | 20 | 20 | 90 | 90 | 100 | 80 |
| A-48 | 1000 | 0 | 10 | 80 | 60 | 80 | 60 |
| A-53 | 1000 | 0 | 0 | 60 | 50 | 70 | 50 |
| A-54 | 1000 | 0 | 0 | 0 | 0 | 70 | 0 |
| A-55 | 1000 | 0 | 0 | 100 | 90 | 100 | 90 |
| A-56 | 1000 | 0 | 0 | 90 | 80 | 100 | 0 |
| A-57 | 1000 | 0 | 0 | 90 | 70 | 90 | 20 |
| A-58 | 1000 | 0 | 0 | 90 | 60 | 90 | 40 |
| A-59 | 1000 | 0 | 0 | 90 | 70 | 90 | 20 |
| A-60 | 1000 | 0 | 0 | 90 | 60 | 90 | 10 |
| A-61 | 1000 | 0 | 0 | 100 | 90 | 100 | 80 |
| A-62 | 1000 | 0 | 0 | 100 | 90 | 100 | 80 |
| A-63 | 1000 | 0 | 0 | 100 | 90 | 100 | 90 |
| A-64 | 1000 | 0 | 0 | 100 | 80 | 100 | 80 |
| A-65 | 1000 | 60 | 90 | 70 | 40 | 70 | 20 |

What is claimed is:
1. A compound of formula I

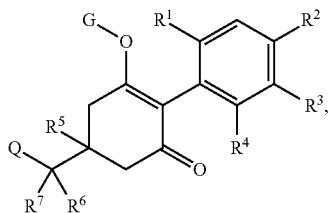

(I)

wherein $R^1$ is methyl, ethyl, n-propyl, isopropyl, cyclopropyl, halomethyl, haloethyl, halogen, vinyl, ethynyl, methoxy, ethoxy, halomethoxy or haloethoxy;

$R^2$ and $R^3$ are, independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro; phenyl, phenyl substituted by $C_1$-$C_4$alkyl, $C_1$-$C_3$haloalkyl, $C_1$-$C_3$alkoxy, $C_1$-$C_3$alkoxy-$C_1$-$C_3$alkoxy, $C_1$-$C_3$haloalkoxy, aminocarbonyl, cyano, nitro, halogen, $C_1$-$C_3$alkylthio, $C_1$-$C_3$alkylsulfinyl or $C_1$-$C_3$alkylsulfonyl; or phenyl wherein 2 adjacent carbon atoms are bridged by a —O—$CH_2$—O— or —O—$CH_2$—$CH_2$—O— group; or heteroaryl or heteroaryl substituted by $C_1$-$C_4$alkyl, $C_1$-$C_3$haloalkyl, $C_1$-$C_3$alkoxy, cyclopropyl-$C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;

$R^4$ is hydrogen, methyl, ethyl, n-propyl, isopropyl, halomethyl, haloethyl, halogen, vinyl, ethynyl, methoxy, ethoxy, halomethoxy or haloethoxy;

$R^5$ is hydrogen or methyl;

$R^6$ and $R^7$ are independently hydrogen, methyl, ethyl, $C_3$-$C_6$cycloalkyl, halogen, halomethyl, haloethyl, halogen, methoxy, halomethoxy, haloethoxy, or together $R^6$ and $R^7$ are joined to form together with the carbon atom to which they are attached a 3-7 membered ring or a 3-7 membered ring substituted by one or two methyl groups; and Q is a 3- to 8-membered saturated or mono-unsaturated heterocycle containing at least one heteroatom selected from O, N and $S(O)_p$;

or Q is a 3- to 8-membered saturated or mono-unsaturated heterocycle containing at least one heteroatom selected from O, N and $S(O)_p$, which is substituted by =O, $C_1$-$C_4$alkyl, $C_1$-$C_4$haloalkyl, $C_1$-$C_4$alkoxy-$C_1$-$C_2$alkyl, $C_3$-$C_6$cycloalkyl or $C_3$-$C_6$cycloalkyl-$C_1$-$C_3$alkyl, or is substituted by a 3- to 6-membered heterocyclyl containing at least one heteroatom selected from O and N, or is substituted by a 3- to 6-membered heterocyclyl-$C_1$-$C_3$alkyl containing at least one heteroatom selected from O and N, or is substituted by a spiro-$C_3$-$C_6$cycloalkyl or a spiro-3- to 8-membered saturated heterocycle containing at least one heteroatom selected from O, N and $S(O)_p$, or is bridged by a —O—$CH_2$— group;

or Q is a 6- to 10-membered bicyclic heterocycle containing at least one heteroatom selected from O, N and $S(O)_p$; and p is 0, 1 or 2; and G is hydrogen, $C_3$alkenyl, $C_3$alkynyl, an alkali metal, alkaline earth metal, a sulfonium, an ammonium or a latentiating group;

wherein, when G is a latentiating group, then G is selected from the groups —$C(X^1)$—$R^6$, —$C(X^2)$—$X^3$—$R^7$, —$C(X^4)$—$NR^8R^9$, —$SO_2R^{10}$, $P(X^5)R^{11}R^{12}$ and $CH_2$—$X^6$—$R^{13}$;

wherein $X^1$, $X^2$, $X^3$, $X^4$, $X^5$ and $X^6$ are independently of each other oxygen or sulfur;

$R^6$, $R^7$, $R^8$ and $R^9$ are each independently of each other hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$aminoalkyl$C_1$-$C_5$alkyl, $C_2$-$C_8$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminooxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl, heteroaryl$C_1$-$C_5$alkyl, $C_2$-$C_5$alkenyl, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

$R^{10}$, $R^{11}$, $R^{12}$ are hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$aminoalkyl$C_1$-$C_5$alkyl, $C_2$-$C_8$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminooxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$aminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl, heteroaryl$C_1$-$C_5$alkyl, $C_2$-$C_5$alkenyl, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino, $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^{13}$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$aminoalkyl$C_1$-$C_5$alkyl, $C_2$-$C_8$dialkylamino$C_1$-$C_5$alkyl, $C_3$-$C_7$cycloalkyl$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_1$-$C_{10}$alkylthioalkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminooxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, $C_1$-$C_5$aminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl, heteroaryl$C_1$-$C_5$alkyl, phenoxy$C_1$-$C_5$alkyl, heteroaryloxy$C_1$-$C_5$alkyl, $C_2$-$C_5$alkenyl, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di$C_3$-$C_7$cycloalkylamino, $C_3$-$C_7$cycloalkoxy or $C_1$-$C_{10}$alkylcarbonyl;

and wherein "heteroaryl" means thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl or thiadiazolyl, or, where appropriate, an N-oxide or a salt thereof.

2. A compound according to claim 1, wherein $R^1$ is methyl, ethyl, cyclopropyl or methoxy.

3. A compound according to claim 1, wherein $R^2$ and $R^3$ are independently hydrogen, halogen, $C_1$-$C_6$alkyl, $C_1$-$C_6$alkoxy, $C_2$-$C_6$alkenyl, $C_2$-$C_6$alkynyl, phenyl or phenyl substituted by $C_1$-$C_4$alkyl, $C_1$-$C_3$haloalkyl, cyano, nitro, halogen or $C_1$-$C_3$alkylsulfonyl.

4. A compound according to claim 1, wherein $R^4$ is hydrogen, methyl, ethyl, chlorine, bromine, vinyl, ethynyl or methoxy.

5. A compound according to claim 1, wherein $R^5$ is hydrogen.

6. A compound according to claim 1, wherein one of $R^6$ and $R^7$ is hydrogen or both of $R^6$ and $R^7$ are hydrogen.

7. A compound according to claim 1, wherein G is hydrogen, an alkali metal or alkaline earth metal.

8. A compound according to claim 1, wherein Q is a group of the formula

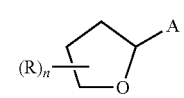
$Q_1$

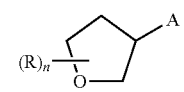
$Q_2$

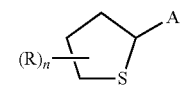
$Q_3$

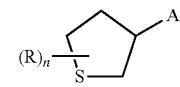
$Q_4$

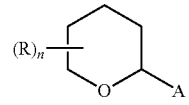
$Q_5$

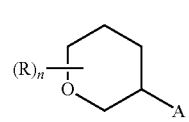
$Q_6$

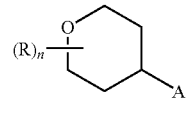
$Q_7$

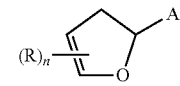
$Q_8$

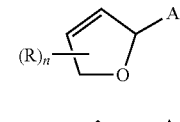
$Q_9$

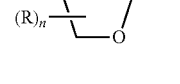
$Q_{10}$

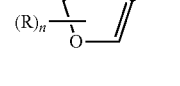
$Q_{11}$

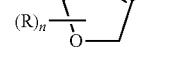
$Q_{12}$

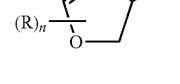
$Q_{13}$

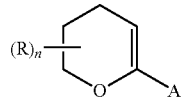
$Q_{14}$

109
-continued
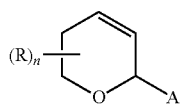 Q15
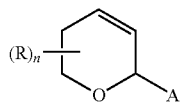 Q16
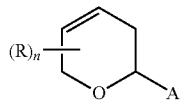 Q17
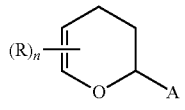 Q18
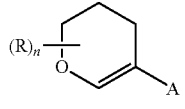 Q19
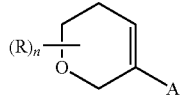 Q20
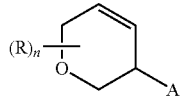 Q21
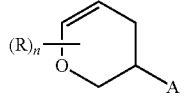 Q22
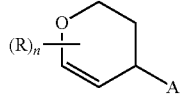 Q23
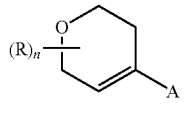 Q24
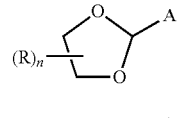 Q25
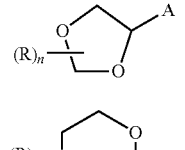 Q26
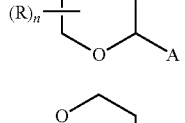 Q27
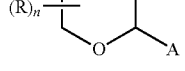 Q28
110
-continued
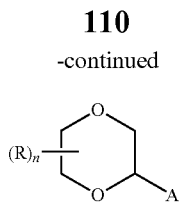 Q29
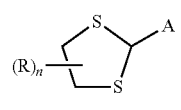 Q30
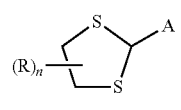 Q31
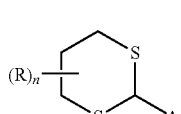 Q32
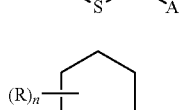 Q33
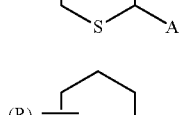 Q34
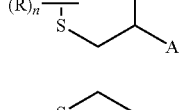 Q35
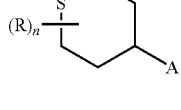 Q36
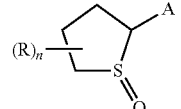 Q37
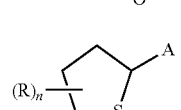 Q38
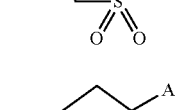 Q39
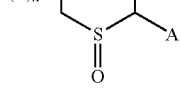 Q40

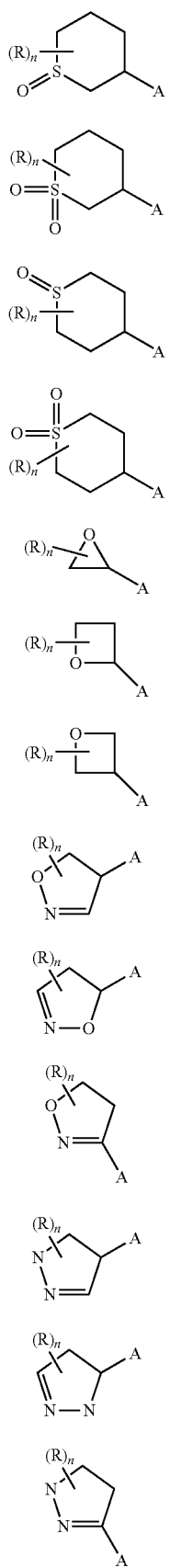
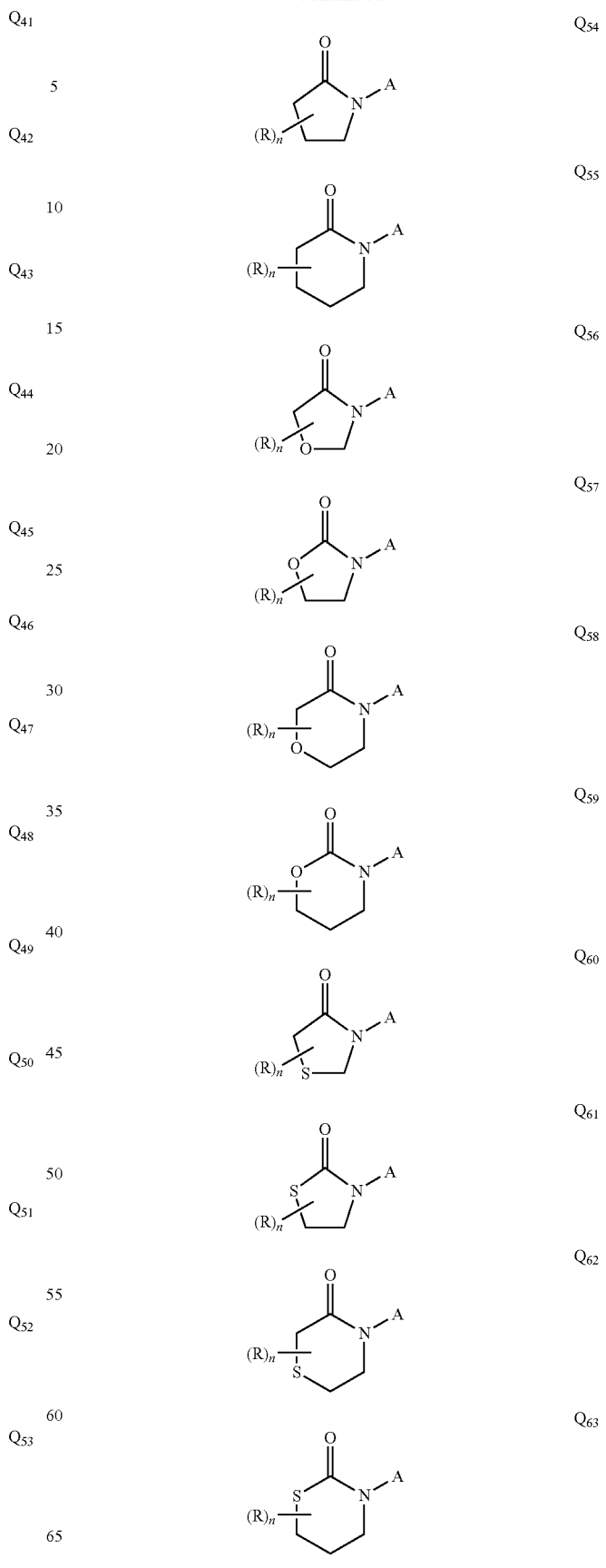

113
-continued

Q64 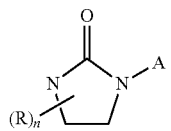

Q65 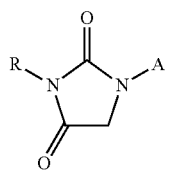

Q66 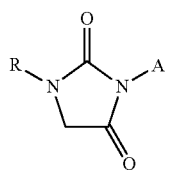

Q67 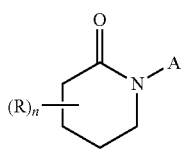

Q68 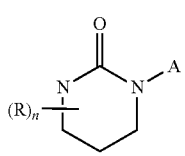

Q69 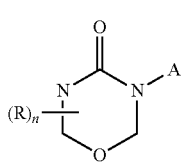

Q70 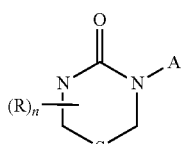

Q74 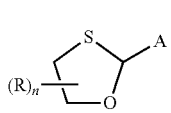

Q75 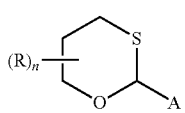

Q76 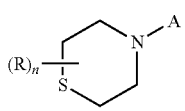

Q77 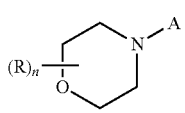

114
-continued

Q78 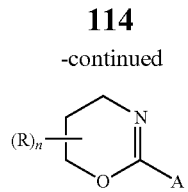

Q79 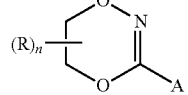

Q80 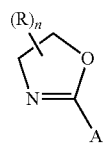

Q81 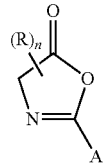

Q82 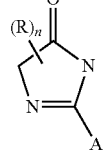

Q83 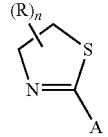

Q84 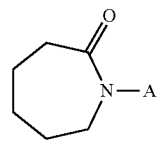

Q85 or 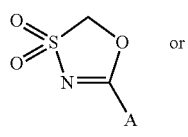

Q86 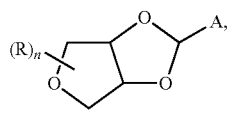

wherein R is $C_{1-4}$ alkyl, $C_{1-4}$ haloalkyl, $C_{1-4}$ alkoxy$C_{1-2}$ alkyl or $C_{3-6}$ cycloalkyl, n is 0 to 4, and -A denotes the position of attachment to the methylene moiety —$CR^5R^6$—.

9. A compound according to claim 8, wherein Q is a group $Q_1, Q_2, Q_5, Q_6, Q_7, Q_{25}, Q_{26}, Q_{27}, Q_{28}, Q_{29}, Q_{34}, Q_{42}$ or $Q_{43}$.

10. A compound according to claim 8, wherein R is methyl or ethyl.

11. A compound according to claim 8, wherein n is 0, 1 or 2.

12. A compound according to claim 1, wherein
$R^1$ is methyl, ethyl or methoxy,
$R^2$ and $R^3$ are independently hydrogen, halogen, $C_1$-$C_6$alkyl, phenyl, phenyl substituted by $C_1$-$C_4$alkyl, $C_1$-$C_3$haloalkyl, $C_1$-$C_3$alkoxy, $C_1$-$C_3$alkoxy-$C_1$-$C_3$alkoxy, $C_1$-$C_3$haloalkoxy, aminocarbonyl, cyano or halogen, or phenyl wherein 2 adjacent carbon atoms are bridged by a —O—$CH_2$—O— or —O—$CH_2$—$CH_2$—O— group, or heteroaryl or heteroaryl substituted by $C_1$-$C_3$alkoxy or cyclopropyl-$C_1$-$C_3$alkoxy,
$R^4$ is hydrogen, methyl or ethyl,
$R^5$ is hydrogen,
$R^6$ and $R^7$ are independently hydrogen or methyl, and
Q is a 5- to 7-membered saturated heterocycle containing at least one heteroatom selected from O and $S(O)_p$,
or Q is a 5- to 7-membered saturated or mono-unsaturated heterocycle containing at least one heteroatom selected from O and $S(O)_p$, which is substituted by $C_1$-$C_4$alkyl or $C_1$-$C_4$alkoxy-$C_1$-$C_2$alkyl, or is substituted by a 5- to 6-membered heterocycyl containing at least one O atom, or is substituted by a 5- to 6-membered heterocyclyl-$C_1$-$C_3$alkyl containing at least one O atom, or is substituted by a spiro-$C_3$-$C_6$cycloalkyl or a spiro-5- to 6-membered saturated heterocycle containing at least one O atom,
or Q is a 8- to 10-membered bicyclic heterocycle containing at least one O atom, and
p is 0, 1 or 2, and
G is hydrogen.

13. A process for the preparation of a compound of formula I according to claim 1, wherein G is hydrogen, which comprises reacting an iodonium ylide of Formula (AG),

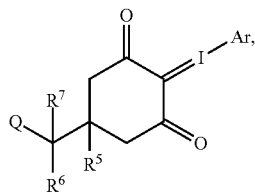

(AG)

wherein Ar is an optionally substituted phenyl group and $R^5$, $R^6$ and $R^7$ are as defined in claim 1, and an aryl boronic acid of Formula (AH)

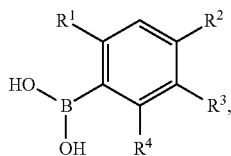

(AH)

wherein $R^1$ to $R^4$ are as defined in claim 1, in the presence of a palladium catalyst, a base and in a solvent.

14. A process for the preparation of a compound of formula I according to claim 1, wherein G is hydrogen, which comprises reacting a compound of formula (Q)

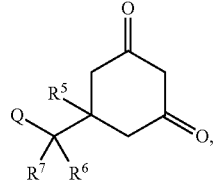

(Q)

wherein $R^5$ to $R^7$ are as defined in claim 1, with a compound of formula (AR)

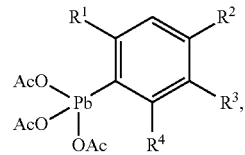

(AR)

wherein $R^1$ to $R^4$ are as defined in claim 1, in the presence of a ligand and in a solvent.

15. A method of controlling grasses and weeds in crops of useful plants, which comprises applying a herbicidally effective amount of a compound of formula I as defined in claim 1, or of a composition comprising such a compound, to the plants or to the locus thereof.

16. A herbicidal composition, which comprises a herbicidally effective amount of a compound of formula I as defined in claim 1, and optionally a further herbicide as mixing partner or a safener or both.

17. A compound according to claim 3, wherein $R^2$ and $R^3$ are independently hydrogen, chlorine, bromine, methyl, methoxy, ethyl, ethoxy, ethenyl, ethynyl, phenyl or phenyl substituted by methyl, trifluoromethyl, cyano, nitro, fluorine, chlorine or methylsulfonyl.

18. A compound according to claim 1, wherein, when G is a latentiating group, then G is a group —$C(X^1)$—$R^6$ or —$C(X^2)$—$X^3$—$R^7$, and the meanings of $X^1$, $R^6$, $X^2$, $X^3$ and $R^7$ are as defined in claim 1.

* * * * *